(12) United States Patent
Wang et al.

(10) Patent No.: US 6,825,201 B2
(45) Date of Patent: Nov. 30, 2004

(54) INDOLE, AZAINDOLE AND RELATED HETEROCYCLIC AMIDOPIPERAZINE DERIVATIVES

(75) Inventors: Tao Wang, Middletown, CT (US); Owen B. Wallace, Zionsville, IN (US); Nicholas A. Meanwell, East Hampton, CT (US); Zhongxing Zhang, Madison, CT (US); John A. Bender, Middletown, CT (US); John F. Kadow, Wallingford, CT (US); Kap-Sun Yeung, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/127,256

(22) Filed: Apr. 22, 2002

(65) Prior Publication Data

US 2003/0096825 A1 May 22, 2003

Related U.S. Application Data

(60) Provisional application No. 60/286,347, filed on Apr. 25, 2001.

(51) Int. Cl.$^7$ .................... A61K 31/496; C07D 403/06; C07D 403/10
(52) U.S. Cl. ........................... 514/254.06; 514/254.09; 514/253.04; 514/254.11; 514/252.13; 544/362; 544/371; 544/373; 544/376
(58) Field of Search ................................ 544/371, 373; 514/254.06, 254.09

(56) References Cited

U.S. PATENT DOCUMENTS

| | | | |
|---|---|---|---|
| 4,791,104 A | 12/1988 | Picciola et al. | |
| 5,023,265 A | 6/1991 | Scherlock et al. | |
| 5,124,327 A | 6/1992 | Greenlee et al. | |
| 5,424,329 A | 6/1995 | Boschelli et al. | |
| 6,172,085 B1 | 1/2001 | Ohkawa et al. | |
| 6,469,006 B1 * | 10/2002 | Blair et al. ............ | 514/253.09 |
| 6,573,262 B2 * | 6/2003 | Wallace et al. .......... | 514/235.2 |

FOREIGN PATENT DOCUMENTS

| | | |
|---|---|---|
| EP | 0530907 A1 | 3/1993 |
| WO | WO 93/01181 | 1/1993 |
| WO | WO 95/04742 | 2/1995 |
| WO | WO 96/11929 | 4/1996 |
| WO | WO 00/51984 | 9/2000 |

OTHER PUBLICATIONS

Drug Evaluations by American Medical Association (6th Ed.), pp. 1615–1627 (1986).*
Nicolau, K.C., et al, "A Novel Strategy for the Solid–Phase Synthesis of Substituted Indolines," J. Am. Chem. Soc., 122(12), pp. 2966–2967, 2000.

(List continued on next page.)

*Primary Examiner*—Emily Bernhardt
(74) *Attorney, Agent, or Firm*—Samuel J. DuBoff

(57) ABSTRACT

The invention comprises substituted indole, azaindole and related heterocyclic amidopiperazine derivatives of general Formula I wherein:
Q is —may represent a bond;
A is selected from the group consisting of $C_{1-6}$alkoxy, $C_{1-6}$alkyl, $C_{3-7}$cycloalkyl, phenyl, and heteroaryl; wherein said heteroaryl may be monocyclic or bicyclic and may be comprised of three to eleven atoms selected from the group consisting of C, N, $NR^9$, O, and S, and wherein each ring of said phenyl and heteroaryl is optionally substituted with one to five same or different substituents selected from the group consisting of $R^{19}$–$R^{23}$;
T is U is $NR^7$, O, or S;
V is $C(H)_kR^1$, O or $N(R^7)_k$;
W is $CR^3$ or $NR^{10}$;
X is $CR^4$ or $NR^{10}$;
Y is $CR^5$ or $NR^{10}$;
Z is $CR^6$ or $NR^{10}$;
k is 0 or 1;
and m, n, and p are each independently 0, 1, or 2 provided that the sum of m, n, and p must equal 1 or 2;
compositions thereof and their use as antiviral agents, particularly for treating HIV infection.

6 Claims, No Drawings

OTHER PUBLICATIONS

M. Font, et al, "Indoles and Pyridazino[4,5-*b*]Indoles as Nonnucleoside Analog Inhibitors of HIV–1 Reverse Transcriptase," Eur. J. Med. Chem., 30, pp. 963–971, 1995.

D. L. Romero, et al, J. Med. Chem., 36, pp. 1505–1508, 1993.

S. D. Young, et al, "2–Heterocyclic Indole–3–Sulfones as Inhibitors of HIV–1 Reverse Transcriptase," Bioorganic & Medicinal Chemistry Letters, 5(5), pp. 491–496, 1995.

M. J. Genin, et al, "Synthesis and Bioactivity of Novel Bis(Heteroaryl)Piperazine (BHAP) Reverse Transcriptase Inhibitors: Structure–Activity Relationships and Increased Metabolic Stability of Novel Substituted Pyridine Analogs," J. Med. Chem., 39, pp. 5267–5275, 1996.

R. Silvestri, et al, Antiviral Chemistry & Chemotherapy, 9, pp. 139–148, 1998.

A. Fredenhagen, et al, "Semicochliodinol A and B: Inhibitors of HIV–1 Protease and EGF–R Protein Tyrosine Kinase Related to Asterriquinones Produced by the Fungus *Chrysosporium Merdarium*," Journal of Antibiotics, 50(5), pp. 395–401, 1997.

M. Kato, et al, "New 5–HT$_3$ (Serotonin–3) Receptor Antagonists. IV. Synthesis and Structure–Activity Relationships of Azabicycloalkaneacetamide Derivatives," Chem. Pharm. Bull., 43(8), pp. 1351–1357, 1995.

V. Levacher, et al, "Broadening in the Scope of NADH Models by Using Chiral and Non–Chiral Pyrrolo [2,3–b] Pyridine Derivatives," TETRAHEDRON, 47(3), pp. 429–440, 1991.

* cited by examiner

INDOLE, AZAINDOLE AND RELATED HETEROCYCLIC AMIDOPIPERAZINE DERIVATIVES

REFERENCE TO RELATED APPLICATIONS

This application claims the benefit of U.S. Provisional Application Ser. No. 60/286,347 filed Apr. 25, 2001.

FIELD OF THE INVENTION

This invention provides compounds having drug and bio-affecting properties, their pharmaceutical compositions and method of use. In particular, the invention is concerned with new heterocyclic amidopiperazine derivatives that possess unique antiviral activity. More particularly, the present invention relates to compounds useful for the treatment of HIV and AIDS.

BACKGROUND ART

HIV-1 (human immunodeficiency virus-1) infection remains a major medical problem, with an estimated 33.6 million people infected worldwide. The number of cases of HIV and AIDS (acquired immunodeficiency syndrome) has risen rapidly. In 1999, 5.6 million new infections were reported, and 2.6 million people died from AIDS. Currently available drugs for the treatment of HIV include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz), and six peptidomimetic protease inhibitors (saquinavir, indinavir, ritonavir, nelfinavir, amprenavir and lopinavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when suboptimal drug concentrations are present (Larder and Kemp; Gulick; Kuritzkes; Morris-Jones et al; Schinazi et al; Vacca and Condra; Flexner; Berkhout and Ren et al; (Ref. 6–14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15). A recent overview of non-nucleoside reverse transcriptase inhibitors: perspectives on novel therapeutic compounds and strategies for the treatment of HIV infection. has appeared (Buckheit, Robert W., Jr. Expert Opinion on Investigational Drugs 2001, 10(8), 1423–1442). A review covering both NRTI and NNRTIs has appeared (Balzarini, J.; De Clercq, E. Antiretroviral Therapy 2001, 31–62.). An overview of the current state of the HIV drugs has been published (E. De clercq Journal of Clinical Virology, 2001, 22, 73–89).

Several indole derivatives including indole-3-sulfones, piperazino indoles, pyrazino indoles, and 5H-indolo[3,2-b][1,5]benzothiazepine derivatives have been reported as HIV-1 reverse transcriptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref. 4). Finally, 3-substituted indole natural products (Semicochliodinol A and B, didemethylasterriquinone and isocochliodinol) were disclosed as inhibitors of HIV-1 protease (Fredenhagen et al, Ref. 22).

Structurally related aza-indole amide derivatives have been disclosed previously (Kato et al, Ref. 23; Levacher et al, Ref. 24; Dompe Spa, WO-09504742, Ref. 5(a); SmithKline Beecham PLC, WO-09611929, Ref. 5(b); Schering Corp., U.S. Pat. No. 5,232,65, Ref. 5(c)). However, these structures differ from those claimed herein in that they are aza-indole mono-amide rather than unsymmetrical aza-indole piperazine diamide derivatives, and there is no mention of the use of these compounds for treating viral infections, particularly HIV. Nothing in these references can be construed to disclose or suggest the novel compounds of this invention and their use to inhibit HIV infection.

REFERENCES CITED

Patent Documents
1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.
3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications
6. Larder, B. A.; Kemp, S. D. Multiple mutations in the HIV-1 reverse transcriptase confer high-level resistance to zidovudine (AZT). *Science*, 1989, 246, 1155–1158.
7. Gulick, R. M. Current antiretroviral therapy: An overview. *Quality of Life Research*, 1997, 6, 471–474.

8. Kuritzkes, D. R. HIV resistance to current therapies. *Antiviral Therapy*, 1997, 2 (Supplement 3), 61–67.
9. Morris-Jones, S.; Moyle, G.; Easterbrook, P. J. Antiretroviral therapies in HIV-1 infection. *Expert Opinion on Investigational Drugs*, 1997, 6(8), 1049–1061.
10. Schinazi, R. F.; Larder, B. A.; Mellors, J. W. Mutations in retroviral genes associated with drug resistance. *International Antiviral News*, 1997, 5, 129–142,.
11. Vacca, J. P.; Condra, J. H. Clinically effective HIV-1 protease inhibitors. *Drug Discovery Today*, 1997, 2, 261–272.
12. Flexner, D. HIV-protease inhibitors. *Drug Therapy*, 1998, 338, 1281–1292.
13. Berkhout, B. HIV-1 evolution under pressure of protease inhibitors: Climbing the stairs of viral fitness. *J. Biomed. Sci.*, 1999, 6, 298–305.
14. Ren, S.; Lien, E. J. Development of HIV protease inhibitors: A survey. *Prog. Drug Res.*, 1998, 51, 1–31.
15. Pedersen, O. S.; Pedersen, E. B. Non-nucleoside reverse transcriptase inhibitors: the NNRTI boom. *Antiviral Chem. Chemother*. 1999, 10, 285–314.
16. (a) De Clercq, E. The role of non-nucleoside reverse transcriptase inhibitors (NNRTIs) in the therapy of HIV-1 infection. *Antiviral Research*, 1998, 38, 153–179. (b) De Clercq, E. Perspectives of non-nucleoside reverse transcriptase inhibitors (NNRTIs) in the therapy of HIV infection. I L. *Farmaco*, 1999, 54, 26–45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino[4,5-b]indoles as nonnucleoside analog inhibitors of HIV-1 reverse transcriptase. *Eur. J. Med. Chem.*, 1995, 30, 963–971.
18. Romero, D. L.; Morge, R. A.; Genin, M. J.; Biles, C.; Busso, M,; Resnick, L.; Althaus, I. W.; Reusser, F.; Thomas, R. C and Tarpley, W. G. Bis(heteroaryl) piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.*, 1993, 36, 1505–1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.*, 1995, 5, 491–496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.*, 1996, 39, 5267–5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139–148.
22. Fredenhagen, A.; Petersen, F.; Tintelnot-Blomley, M.; Rosel, J.; Mett, H and Hug, P. J. Semicochliodinol A and B: Inhibitors of HIV-1 protease and EGF-R protein Tyrosine Kinase related to Asterriquinones produced by the fungus Chrysosporium nerdarium. *Antibiotics*, 1997, 50, 395–401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.*, 1995, 43, 1351–1357.
24. Levacher, V.; Benoit, R.; Duflos, J; Dupas, G.; Bourguignon, J.; Queguiner, G. Broadening the scope of NADH models by using chiral and non chiral pyrrolo [2,3-b]pyridine derivatives. *Tetrahedron*, 1991, 47, 429–440.
25. Shadrina, L. P.; Dormidontov, Yu. P.; Ponomarev, V, G.; Lapkin, I. I. Reactions of organomagnesium derivatives of 7-aza- and benzoindoles with diethyl oxalate and the reactivity of ethoxalylindoles. *Khim. Geterotsikl. Soedin.*, 1987, 1206–1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100–106.
27. (a) Desai, M.; Watthey, J. W. H.; Zuckerman, M. A convenient preparation of 1-aroylpiperazines. *Org. Prep. Proced. Int.*, 1976, 8, 85–86. (b) Adamczyk, M.; Fino, J. R. Synthesis of procainamide metabolites. N-acetyl desethylprocainamide and desethylprocainamide. *Org. Prep. Proced. Int*. 1996, 28, 470–474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (d) Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662.
28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.*, 1999, 1, 91–93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.*, 1997, 45, 134–137.
30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.*, 1980, 45, 4045–4048.
31. Shiotani, S.; Tanigochi, K. Furopyridines. XXII [1]. Elaboration of the C-substituents alpha to the heteronitrogen atom of furo[2,3-b]-, -[3.2-b]-, -[2.3-c]- and -[3,2-c]pyridine. *J. Het. Chem.*, 1997, 34, 901–907.
32. Minakata, S.; Komatsu, M.; Ohshiro, Y. Regioselective functionalization of 1H-pyrrolo[2,3-b]pyridine via its N-oxide. *Synthesis*, 1992, 661–663.
33. Klemm, L. H.; Hartling, R. Chemistry of thienopyridines. XXIV. Two transformations of thieno[2,3-b] pyridine 7-oxide (1). *J. Het. Chem.*, 1976, 13, 1197–1200.
34. Antonini, I.; Claudi, F.; Cristalli, G.; Franchetti, P.; Crifantini, M.; Martelli, S. Synthesis of 4-amino-1-□-D-ribofuranosyl-1H-pyrrolo[2,3-b]pyridine (1-Deazatubercidin) as a potential antitumor agent. *J. Med. Chem.*, 1982, 25, 1258–1261.
35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069–1077. (b) Miura, Y.; Yoshida, M.; Hamana, M. Synthesis of 2,3-fused quinolines from 3-substituted quinoline 1-oxides. Part II, *Heterocycles*, 1993, 36, 1005–1016. (c) Profft, V. E.; Rolle, W. Uber 4-merkaptoverbindungendes 2-methlpyridins. *J. Prakt. Chem.*, 1960, 283 (11), 22–34.
36. Nesi, R.; Giomi, D.; Turchi, S.; Tedeschi, P., Ponticelli, F. A new one step synthetic approach to the isoxazolo[4,5-b]pyridine system. *Synth. Comm.*, 1992, 22, 2349–2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378–1381. (b) Barker, G.; Ellis, G. P. Benzopyrone. Part I. 6-Amino- and 6-hydroxy-2-subtituted chromones. *J. Chem. Soc.*, 1970, 2230–2233.
38. Ayyangar, N. R.; Lahoti, R J.; Daniel, T. An alternate synthesis of 3,4-diaminobenzophenone and mebendazole. *Org. Prep. Proced. Int.*, 1991, 23, 627–631.
39. Mahadevan, I.; Rasmussen, M. Ambident heterocyclic reactivity: The alkylation of pyrrolopyridines (azaindoles, diazaindenes). *Tetrahedron*, 1993, 49, 7337–7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654–660.
41. Bodanszky, M.; Bodanszky, A. *"The Practice of Peptide Synthesis"* $2^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.*, 1998 28, 2761 and references cited therein; (b) Bernasconi, S. et al. *Synthesis*, 1980, 385.
45. (a) Jaszay Z. M. et al. *Synthesis*, 1989, 745 and references cited therein; (b) Nicolaou, K. C. et al. *Angew. Chem. Int. Ed.* 1999, 38, 1669.
46. Ooi, T. et al. *Synlett*. 1999, 729.
47. Ford, R. E. et al. *J. Med. Chem.* 1986, 29, 538.
48. (a) Yeung, K.-S. et al. Bristol-Myers Squibb Unpublished Results. (b) Wang, W. et al. *Tetrahedron Lett.* 1999, 40, 2501.
49. Brook, M. A. et al. *Synthesis*, 1983, 201.
50. Yamazaki, N. et al. *Tetrahedron Lett.* 1972, 5047.
51. Barry A. Bunin "The Combinatorial Index" 1998 Academic Press, San Diego/London pages 78–82.
52. Richard C. Larock Comprehensive Organic Transormations 2nd Ed. 1999, John Wiley and Sons New York.
53. M. D. Mullican et. al. *J. Med. Chem.* 1991, 34, 2186–2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968
56. Paquette, Leo A. Principles of modem heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed.Oxford (Oxfordshire); New York: Pergamon Press, 1984.8 v.
58. Katritzky, Alan RHandbook of heterocyclic 1st edOxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987–c1992. Chemistry of heterocyclic compounds; v.47.
61. Joule, J. A Mills, K., Smith, G. F. Heterocyclic Chemistry, 3rd ed London ;New York Chapman & Hall, 1995.
62. Katritzky, Alan R., Rees, Charles W., Scriven, Eric F. V. Comprehensive heterocyclic chemistry II: a review of the literature 1982–1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles: structure, reactions, syntheses, and applications Stuttgart; New York: G. Thieme, 1995.
65. Grimmett, M. R. Imidazole and benzimidazole Synthesis London; San Diego: Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex : Longman, 1997. 414 p.: ill.; 24 cm.
68. Farina, Vittorio; Roth, Gregory P. Recent advances in the Stille reaction; *Adv. Met.-Org. Chem.* 1996, 5, 1–53.
69. Farina, Vittorio; Krishnamurthy, Venkat; Scott, William J. The Stille reaction; *Org. React.* (N.Y.) (1997), 50, 1–652.
70. Stille, J. K. *Angew. Chem. Int. Ed. Engl.* 1986, 25, 508–524.
71. Norio Miyaura and Akiro Suzuki *Chem Rev.* 1995, 95, 2457.
72. Home, D. A. *Heterocycles* 1994, 39, 139.
73. Kamitori, Y. et. al. *Heterocycles*. 1994, 37(1), 153.
74. Shawali, *J. Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52–53.
81. *Ind J. Chem.* 1973,11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828–5832.
85. Bowden, K. et. al. *J. Chem. Soc.* 1946, 953.
86. Nitz, T. J. et. al. *J. Org. Chem.* 1994, 59, 5828–5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419–6422. (c) Jenneskens, L. W.; Mahy, J.; den Berg, E. M. M. de B.-v.; Van der Hoef, I.; Lugtenburg, J. *Recl. Trav. Chim. Pays-Bas* 1995, 114, 97.
89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661–7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470–474. (b) Wang, T.; Zhang, Z.; Meanwell, N. A. Regioselective mono-Benzoylation of Unsymmetrical Piperazines. *J. Org. Chem.*, in press.

91. Masuzawa, K.; Kitagawa, M.; Uchida, H. *Bull Chem. Soc. Jpn.* 1967, 40, 244–245.

92. Furber, M.; Cooper, M. E.; Donald, D. K. *Tetrahedron Lett.* 1993, 34, 1351–1354.

SUMMARY OF THE INVENTION

The present invention comprises compounds of Formula I, their pharmaceutical formulations, and their use in patients suffering from or susceptible to a virus such as HIV. The compounds of Formula I, which include nontoxic pharmaceutically acceptable salts and/or hydrates thereof, have the formula and meaning as described below. Each embodiment of a particular aspect of the invention depends from the preceding embodiment unless otherwise stated.

A first embodiment of a first aspect of the present invention are compounds of Formula I, including pharmaceutically acceptable salts thereof,

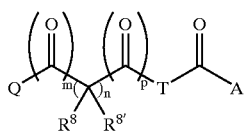

I wherein:

Q is

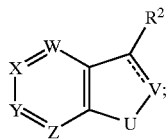

— may represent a bond;

A is selected from the group consisting of $C_{1-6}$alkoxy, $C_{1-6}$alkyl, $C_{3-7}$cycloalkyl, phenyl, and heteroaryl; wherein said heteroaryl may be monocyclic or bicyclic and may be comprised of three to eleven atoms selected from the group consisting of C, N, $NR^9$, O, and S, and wherein each ring of said phenyl and heteroaryl is optionally substituted with one to five same or different substituents selected from the group consisting of $R^{19}$–$R^{23}$;

T is

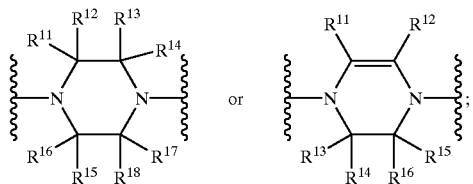

U is $NR^7$, O, or S;

V is $C(H)_kR^1$, O or $N(R^7)_k$;

W is $CR^3$ or $NR^{10}$;

X is $CR^4$ or $NR^{10}$;

Y is $CR^5$ or $NR^{10}$;

Z is $CR^6$ or $NR^{10}$;

k is 0 or 1;

$R^1$, $R^2$, $R^3$, $R^4$, $R^5$, and $R^6$ are each independently selected from the group consisting of a bond, hydrogen, halogen, cyano, nitro, $X'R^{24}$, $C_{1-6}$alkyl, $C_{3-7}$cycloalkyl, $C_{2-6}$alkenyl, $C_{4-7}$cycloalkenyl, $C_{2-6}$alkynyl, aryl, heteroaryl, heteroalicyclic, $C(O)NR^{28}R^{29}$, and $CO_2R^{25}$, wherein said $C_{1-6}$alkyl, $C_{3-7}$cycloalkyl, $C_{2-6}$alkenyl, $C_{4-7}$cycloalkenyl, $C_{2-6}$alkynyl, aryl, heteroaryl, and heteroalicyclic are optionally substituted with one to nine same or different halogens or from one to five same or different substituents selected from the substituents comprising group F;

$R^7$ and $R^{7'}$ are each independently selected from the group consisting of a bond and $(CH_2)_rH$, wherein r is 0–6;

m, n, and p are each independently 0, 1, or 2 provided that the sum of m, n, and p must equal 1 or 2;

F is selected from the group consisting of $C_{1-6}$alkyl, hydroxy, $C_{1-6}$alkoxy, cyano, halogen, benzyl, N-amido, $NR^{30}R^{31}$, $C_{1-6}$alkylC(O)NR$^{30}$R$^{31}$, C(O)NR$^{30}$R$^{31}$, COOR$^{32}$, and $C_{1-6}$alkylCOOR$^{32}$;

$R^8$ and $R^{8'}$ are each independently selected from the group consisting of hydrogen, hydroxy, $C_{1-6}$alkyl, $C_{1-6}$alkoxy, cyano, and fluoro, or $R^8$ and $R^{8'}$ taken together form =O, =S, =NOR$^9$, or =NH;

$R^9$ is hydrogen or $C_{1-6}$alkyl;

$R^{10}$ is $(O)_q$, wherein q is 0 or 1;

$R^{11}$, $R^{12}$, $R^{13}$, $R^{14}$, $R^{15}$, $R^{16}$, $R^{17}$, and $R^{18}$ are each independently selected from hydrogen or $C_{1-3}$alkyl;

X' is selected from the group consisting of $NR^9$, O, and S;

$R^{19}$, $R^{20}$, $R^{21}$, $R^{22}$, and $R^{23}$ are each independently selected from the group consisting of hydrogen, $C_{1-6}$alkyl, $C_{2-6}$alkenyl, $C_{2-6}$alkynyl, halogen, cyano, $X'R^{26}$, trifluoromethyl, and trifluoromethoxy, wherein each of said $C_{1-6}$alkyl, $C_{2-6}$alkenyl, and $C_{2-6}$alkynyl are optionally substituted with one to three same or different substituents selected from halogen and $C_{1-6}$alkyl;

$R^{24}$ is hydrogen or $C_{1-6}$alkyl;

$R^{25}$ is selected from the group consisting of hydrogen, $C_{1-6}$alkyl, and $C_{3-7}$cycloalkyl;

$R^{26}$ is selected from the group consisting of hydrogen, $C_{1-6}$alkyl, $C_{3-7}$cycloalkyl, trifluoromethyl and $C(O)R^{27}$;

$R^{27}$ is selected from the group consisting of $C_{1-6}$alkyl, $NH_2$ and —$NHC_{1-3}$alkyl;

$R^{28}$ and $R^{29}$ are independently selected from the group consisting of hydrogen, $C_{1-6}$alkyl, $C_{3-7}$cycloalkyl, aryl, heteroaryl, and heteroalicyclic wherein said $C_{1-6}$alkyl, $C_{3-7}$cycloalkyl, aryl, heteroaryl, and heteroalicyclic are optionally substituted with one to nine same or different halogens or $C_{1-6}$alkyl groups;

$R^{30}$ and $R^{31}$ are independently selected from the group consisting of hydrogen, $C_{1-6}$alkyl, $C_{3-7}$cycloalkyl, aryl, wherein said $C_{1-6}$alkyl, $C_{3-7}$cycloalkyl, and aryl are optionally substituted with one to nine same or different halogens;

$R^{32}$ is selected from the group consisting of hydrogen, $C_{1-6}$alkyl, and $C_{3-7}$cycloalkyl;

provided that if one of the members selected from the group consisting of W, X, Y, and Z is $NR^{10}$, then the remaining members selected from the group consisting of W, X, Y, and Z are not $NR^{10}$;

provided when U is O or S then V is $C(H)_kR^1$ or $N(R^7)_k$;

provided when U is NR$^7$; V is C(H)$_k$R$^1$; W is CR$^2$; X is CR$^3$; Y is CR$^4$; Z is CR$^5$; m is 1; n is 0; and p is 1 then R$^2$ is not a bond;

provided when U is NR$^7$; V is C(H)$_k$R$^1$; one of the variables selected from W, X, Y, and Z is NR$^{10}$; m is 1; n is 0; and p is 0 or 1 then R$^2$ is not a bond;

provided that when V is O then —— does not represent a bond;

provided that when —— represents a bond then k is 0; and provided that at any given time only one of the members selected from the group consisting of R$^1$, R$^2$, R$^3$, R$^4$, R$^5$, R$^6$, R$^7$ and R$^{7'}$ is a bond, and further provided that said bond is the point of attachment to the adjacent carbon atom in the compound of Formula I.

A second embodiment of the first aspect of the present invention are compounds of Formula I, including pharmaceutically acceptable salts thereof, wherein:

T is

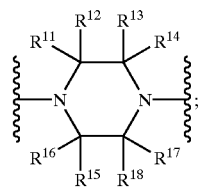

R$^{11}$, R$^{12}$, R$^{13}$, R$^{14}$, R$^{15}$, R$^{16}$, R$^{17}$, and R$^{18}$ are each independently hydrogen, methyl or ethyl; and —— represents a bond;

A is phenyl or heteroaryl.

A third embodiment of the first aspect of the present invention are compounds of Formula I, including pharmaceutically acceptable salts thereof, wherein:

U is NR$^7$; and

R$^8$ and R$^{8'}$ are each independently hydrogen, hydroxy or cyano, with the proviso that only one of R$^8$ and R$^{8'}$ is cyano.

A fourth embodiment of the first aspect of the present invention are compounds of Formula I, including pharmaceutically acceptable salts thereof, wherein:

m is 1; n is 0; and p is 1.

A fifth embodiment of the first aspect of the present invention, which depends from the second embodiment of the first aspect, are compounds of Formula I, including pharmaceutically acceptable salts thereof, wherein:

U is O or S;

V is CH or N; and

R$^8$ and R$^{8'}$ are each independently hydrogen, hydroxy or cyano, with the proviso that only one of R$^8$ and R$^{8'}$ is cyano.

A sixth embodiment of the first aspect of the present invention, which depends from the fifth embodiment of the first aspect, are compounds of Formula I, including pharmaceutically acceptable salts thereof, wherein:

m is 1; n is 0; and p is 1.

A seventh embodiment of the first aspect of the present invention, which depends from the third embodiment of the first aspect, are compounds of Formula I, including pharmaceutically acceptable salts thereof, wherein:

U is ——NR$^7$; and V is N.

Another embodiment of the seventh embodiment are compounds wherein U is NH, n is 0, and R$^2$ is the point of attachment to Q.

Another embodiment of the fourth embodiment are compounds wherein W,X,Y and Z are C.

Another embodiment of the third embodiment are compounds wherein m is 1; n is 0; and p is 0.

Another embodiment of the prior embodiment are compounds wherein R$^2$ is the point of attachment to Q and V is CH.

Another embodiment of the prior embodiment are compounds wherein W,X,Y and Z are C.

Another embodiment of the third embodiment are compounds wherein R$^2$ is the point of attachment to Q, V is CH, m is 0, and one of R$^8$ and R$^{8'}$ are hydrogen and the other is hydroxy.

Another embodiment of the prior embodiment are compounds wherein W,X,Y and Z are C.

Another embodiment of the third embodiment are compounds wherein R$^2$ is the point of attachment to Q, V is CH, m is 0, and R$^8$ and R$^{8'}$ are each hydrogen.

Another embodiment of the prior embodiment are compounds wherein W,X,Y and Z are C.

Another embodiment of the second embodiment are compounds wherein R$^2$ is the point of attachment to Q, V is CH, m is 0, and one of R$^8$ and R$^{8'}$ are hydrogen and the other is cyano.

Another embodiment of the prior embodiment are compounds wherein U is NR$^7$.

A first embodiment of the second aspect of the present invention is a pharmaceutical composition which comprises an antiviral effective amount of a compound of Formula I, including pharmaceutically acceptable salts thereof, as defined in any of the prior embodiments of the first aspect of the present invention, and one or more pharmaceutically acceptable carriers, excipients or diluents.

A second embodiment of the second aspect of the present invention is the pharmaceutical composition of the first embodiment of the second aspect, useful for treating infection by HIV, which additionally comprises an antiviral effective amount of an AIDS treatment agent selected from the group consisting of an AIDS antiviral agent; an anti-infective agent; an immunomodulator; and HIV entry inhibitors.

A first embodiment of a third aspect of the present invention is a method for treating a mammal infected with a virus, comprising administering to said mammal an antiviral effective amount of a compound of Formula I, including pharmaceutically accceptable salts thereof, as defined in any of the prior embodiments of the first aspect of the present invention, and one or more pharmaceutically acceptable carriers, excipients or diluents.

A second embodiment of a third aspect of the present invention is the method of the first embodiment of the third aspect, comprising administering to said mammal an antiviral effective amount of a compound of Formula I, in combination with an antiviral effective amount of an AIDS treatment agent selected from the group consisting of: an AIDS antiviral agent; an anti-infective agent; an immunomodulator; and an HIV entry inhibitor.

The third embodiment of a third aspect of the present invention is the method of either the first or second embodiment of the third aspect, wherein said virus is HIV.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

DEFINITIONS

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are furyl, thienyl, benzothienyl, thiazolyl, imidazolyl, oxazolyl, oxadiazolyl, thiadiazolyl, benzthiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, and pyrazinyl.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. For example, the term "$C_{1-6}$alkyl" as used herein and in the claims (unless specified otherwise) mean straight or branched chain alkyl groups such as methyl, ethyl, propyl, isopropyl, butyl, isobutyl, t-butyl, amyl, hexyl and the like.

A "cycloalkyl" group refers to a saturated all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclohexane, cycloheptane, and adamantane.

A "cycloalkenyl" group refers to an all-carbon monocyclic or fused ring (i.e., rings which share and adjacent pair of carbon atoms) group wherein one or more rings contains one or more carbon-carbon double bonds but does not have a completely conjugated pi-electron system. Examples, without limitation, of cycloalkenyl groups are cyclopentene, cyclohexadiene, and cycloheptatriene.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "O-carboxy" group refers to a R"C(O)O-group, with R" as defined herein.

An "amino" group refers to an —$NH_2$ group.

A "N-amido" group refers to a $R^xC(=O)NR^y$— group, with $R^x$ selected from the group consisting of alkyl, cycloalkyl, aryl, heteroaryl, and heteroalicyclic and $R^y$ selected from hydrogen or alkyl.

A "cyano" group refers to a —CN group.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (-)6-Chloro-4-(S)-cyclopropylethynyl-4(S)-trifluoro-methyl-1,4-dihydro- | DuPont Merck | HIV infection, AIDS, ARC (non-nucleoside RT inhibitor) |
| 2H-3,1-benzoxazin-2-one,STOCRINE EL10 | Elan Corp. PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |

ANTIVIRALS

| Drug Name | Manufacturer | Indication |
| --- | --- | --- |
| Zidovudine; AZT | Glaxo Wellcome | HIV infection, AIDS, ARC, Kaposi's sarcoma, in combination with other therapies |

IMMUNOMODULATORS

| Drug Name | Manufacturer | Indication |
| --- | --- | --- |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon | Hoffman-La Roche | Kaposi's sarcoma |
| Alfa 2a | | AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
| --- | --- | --- |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Pouleuc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in Drugs Of The Future 1999, 24(12), pp. 1355–1362; Cell, Vol. 9, pp. 243–246, Oct. 29, 1999; and Drug Discovery Today, Vol. 5, No. 5, May 2000, pp. 183–194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddl and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The preparative procedures and anti-HIV-1 activity of the novel heterocyclic amidopiperazine derivatives of Formula I are summarized below.

Abbreviations

The following abbreviations, most of which are conventional abbreviations well known to those skilled in the art, are used throughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
PMB=4-Methoxybenzyl
DDQ=2,3-Dichloro-5, 6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCC=1,3-dicyclohexyl-carbodiimide Chemistry The present invention comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Synthesis of Intermediates

It should be noted that in many cases reactions are depicted for only one position of an intermediate or compound of Formula I, such as the $R^6$ position, for example. It is to be understood that such reactions could be used at other positions, such as $R^1$–$R^4$ or $R^7$ of the various intermediates or compounds of Formula I. Reaction conditions and methods given in the specific examples are broadly applicable to compounds with other substitution and to other tranformations in this application.

Heterocyclic carboxylates of general formula QC(O)OR' or QC(O)$L^1$ (such as those of formula IIa in Scheme 1A or formula II in Scheme 1, herein) or suitable surrogates may be purchased from commercial sources or synthesized. R' is usually a simple alkyl, preferably methyl or alternatively ethyl. Simple $C_1$–$C_6$ alkyl esters or phenyl or substituted phenyl ethers also are suitable. $L^1$ represents a leaving group and may represent OR' herein. The heterocyclic carboxylates of formula IIa or II can be prepared by two basic strategies using numerous methods from the literature or the methods within this application. The first strategy involves the synthesis of an appropriate heterocycle containing a carboxylate ester group while the second strategy involves the synthesis of the parent heterocycle followed by installation of a carboxylate ester moiety onto the parent heterocycle. The following Schemes I-1 through I-17 represent various heterocyclic carboxylates which may serve as useful intermediates for the preparation of compounds of Formula I. The methods used to prepare compounds of Formula I from the heterocyclic carboxylates are those described for Schemes 1, 1A and 2.

Schemes I-1 through I-12 depict methods and conditions for the synthesis of azaindole and indole carboxylates according to the first strategy wherein an indole or azainole containing a carboxylate moiety is synthesized. Literature references follow the depicted Schemes.

Scheme I-1

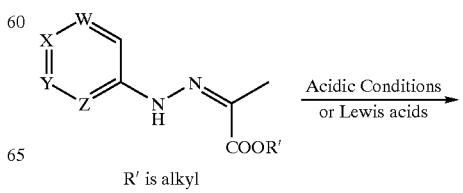

R' is alkyl

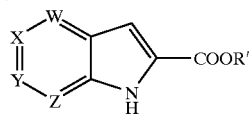

The preparation of of azaindole and indole carboxylates may be accomplished according to procedures which are known in the art. For example, the methods described in references such as Chikvaidze, I.; Megrelishvili, N.; Samsoniya, S. A.; Suvorov, N. N.; *Khim Geterotsikl Soedin* 1991, 11, 1508–1511; Murakami, Y.; Takahashi, H.; Nakazawa, Y.; Koshimizu, M.; et al.; *Tetrahedron Lett.* 1989, 30, 2099; Rydon, H. N.; Siddappa, S.; *J. Chem. Soc.* 1951, 2462; Justoni, R.; Pessina, R.; Farmaco, Ed. Sci. 1955, 10, 356; Ishii, H.; Murakami, Y.; Hosoya, K.; Takeda, H.; et al.; *Chem. Pharm. Bull.* 1973, 21, 1481; and Speicher, A.; Eicher, T.; Tevzadze, L. M.; Khoshtariya, T. E.; *J. Prakt Chem/Chem-Ztg* 1997, 339(7), 669–671 may be used to prepare either indole or azaindole (wherein one of W, X, Y, or Z is $NR^{10}$) carboxylates as shown in Scheme I-1, above.

Another method for the synthesis of indole-2-carboxylates or azaindole-2-carboxylates is shown below in Scheme I-2. The preparation of the indole-2-carboxylates, wherein W, X, Y, and Z are $CR^2$, $CR^3$, $CR^4$, and $CR^5$, respectively, can be carried out according to methods as described numerous literature references. These references incude Martin, P.; Winkler, T.; *Helv Chim Acta* 1994, 77(1), 111–120; Jones, G. B.; Moody, C. J.; *J. Chem. Soc., Perkin Trans.* 1 1989, 2455; Gaims, R. S.; Grant, R. D.; Moody, C. J.; Rees, C. W.; Tsoi, S. C.; *J. Chem. Soc., Perkin Trans.* 1 1986,483; Mackenzie, A. R.; Moody, C. J.; Rees, C. W.; *Tetrahedron* 1986, 42, 3259; Hemetsberger, H.; Knittel, D.; Weidmann, H.; *Monatsh Chem* 1970,101, 161; Kawase, M.; Sinhababu, A. K.; Borchardt, R. T.; *Chem. Pharm. Bull.* 1990, 38(11), 2939–2946; Watanabe, T; Takahashi, H.; Kamakura, H.; Sakaguchi, S.; Osaki, M.; Toyama, S.; Mizuma, Y.; Ueda, I.; Murakami, Y.; *Chem. Pharm. Bull.* 1991, 39(12), 3145–3152; Molina, P.; Tarraga, A.; Ferao, A.; Gaspar, C.; *Heterocycles* 1993, 35(1), 427–432; Bolton, R. E.; Moody, C. J.; Rees, C. W.; *J. Chem. Soc., Perkin Trans.* 1 1989,2136; Bolton, R. E.; Moody, C. J.; Rees, C. W.; Tojo, G. *J. Chem. Soc., Perkin Trans.* 1 1987, 931; Samanta, S. S.; Ghosh, S. C.; De, A.; *J. Chem. Soc., Perkin Trans.* 1 1997, 24, 3673–3677; Romero, A. G.; Leiby, J. A.; McCall, R. B.; Piercey, M. F.; Smith, M. W.; Han, F.; *J. Med. Chem.* 1993, 36(15), 2066–2074; and Boger, D. L.; Coleman, R. S.; Invergo, B. J.; *J. Org. Chem.* 1987, 52, 1521. Similar methodology can be extended to synthesize azaindole-2-carboxylates wherein one of W, X, Y, and Z is $NR^{10}$ as described in Molina, P.; Alajarin, M.; Sanchez-Andrada, P.; *Synthesis* 1993, 2, 225–228.

Scheme I-2

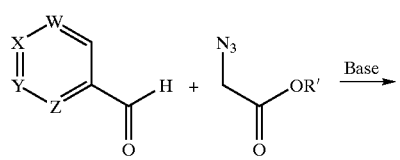

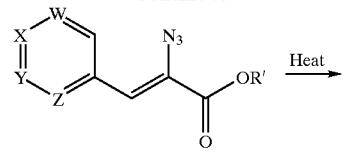

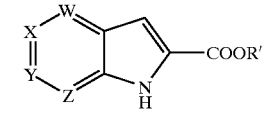

Another method for preparing indole-2-carboxylates or azaindole-2-carboxylates is shown below in Scheme I-3 wherein the nitro group is reductively cyclized with the alkenyl ester moiety shown to provide the indole-2-carboxylate carboxylates or azaindole-2-carboxylate as depicted. The preparation of the indole-2-carboxylates, wherein W, X, Y, and Z are $CR^3$, $CR^4$, $CR^5$, and $CR^6$, respectively, can be carried out according to the conditions shown and as further described in references such as Akazome, M.; Kondo, T.; Watanabe, Y.; *J. Org. Chem.* 1994, 59(12), 3375–3380; Kametani, T.; Nyu, K.; Yamanaka, T.; Yagi, H.; Ogasawara, K.; *Tetrahedron Lett.* 1969, 1027; Crotti, C.; Cenini, S.; et al.; *J. Chem. Soc., Chem. Commun.* 1986, 10, 784; and Mali, R. S.; Yadav, V. J.; *Synthesis* 1984, 10, 862. The same methodology can be extended to synthesize azaindole-2-carboxylates wherein one of W, X, Y, and Z is $NR^{10}$.

Scheme I-3

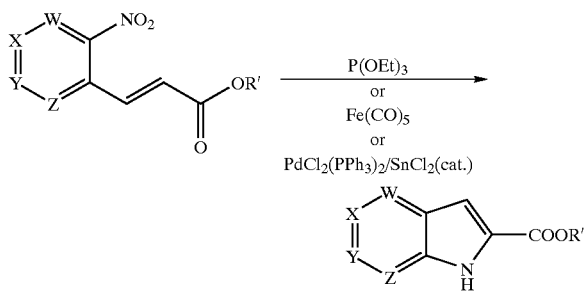

Another similar synthesis of either indole-2-carboxylates or azaindole-2-carboxylates is shown below in Scheme I-4 and may be carried out according to methods descibed in literature references such as Yakhontov, L. N.; Azimov, V. A.; Lapan, E. I.; *Tetrahedron Lett.* 1969, 1909; Scott, A. I.; Townsend, C. A.; Okada, K.; Kajiwara, M.; *J. Am. Chem. Soc.* 1974, 96, 8054; Frydman, B.; Baldain, G.; Repetto, J. C.; *J. Org. Chem.* 1973, 38, 1824 and Fisher, M. H.; Matzuk, A. R.; *J. Heterocycl. Chem.* 1969, 6, 775.

Scheme I-4

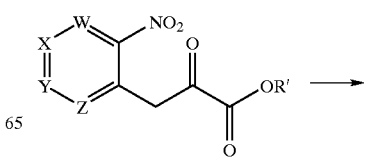

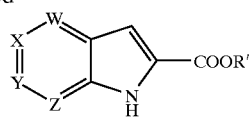

Scheme I-5

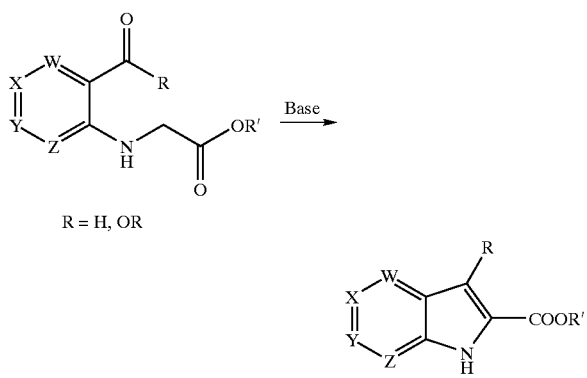

Scheme I-5, above, depicts the formation of indole-2-carboxylates where W, X, Y, and Z are $CR^3$, $CR^4$, $CR^5$, and $CR^6$, respectively, and which may be accomplished by the base induced cyclization of an ester intermediate according to methods such as those described in Boes, M.; Jenck, F.; Martin, J. R.; Moreau, J. L.; Mutel, V.; Sleight, A. J.; Widmer, U.; *Eur. J. Med. Chem.* 1997, 32(3), 253–261; Robertson, A.; *J. Chem. Soc.* 1927, 1937. The corresponding azaindole-2-carboxylates may be prepared according to the methods described in Willette, R. E.; *Adv. Heterocycl. Chem.* 1968, 9, 27.

The preparation of indole-2-carboxylates, wherein W, X, Y, and Z are $CR^3$, $CR^4$, $CR^5$, and $CR^6$, respectively, may also be accomplished by a palladium mediated cyclization reaction as shown below in Scheme I-6 and according to methods as described in Koerber-Ple, K.; Massiot, G.; *Synlett.* 1994, 9, 759–760; and Chen, C.; Lieberman, D. R.; Larsen, R. D.; Verhoeven, T. R.; Reider, P. J.; *J. Org. Chem.* 1997, 62(9), 2676–2677. The preparation of azaindole-2-carboxylates, wherein one of W, X, Y, and Z is $NR^{10}$, may be accomplished according to methods such as those described by Morris, J. J.; Hughes, L. R.; Glen, A. T.; Taylor, P. J.; *J. Med. Chem.* 1991, 34(1), 447–455; and Kutney, J. P.; Noda, M.; Lewis, N. G.; Monteiro, B.; et al.; *Heterocycles* 1981, 16, 1469.

Scheme I-6

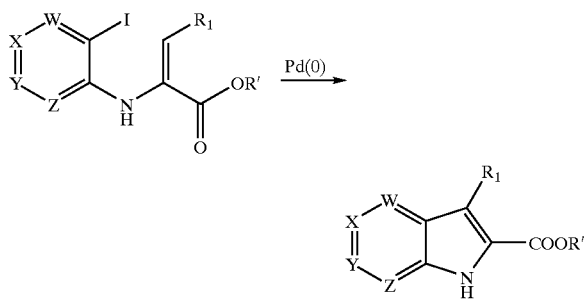

The following schemes depict the second strategy for the preparation of heterocyclic carboxylates such as indole carboxylates or azaindole carboxylates by using methods for adding carboxy ester groups to heterocycles such as indoles or aza indoles. Starting indole intermediates or precursors for carbomethoxylation are known or are readily prepared according to literature procedures, such as those described in Gribble, G. W., Recent developments in indole ring synthesis-methology and applications, *Contemp. Org. Synth.* 1994, 1, 145–72 and in Gribble, G.; *J. Chem Soc. Perkin Trans* 1, 2000, 1045–1075.

Indoles or aza indoles may be prepared via the well known Bartoli reaction in which vinyl magnesium bromide reacts with an aryl or heteroaryl nitro group, to form a five-membered nitrogen containing ring. Some references for the above transformation include: Bartoli et al. a) *Tetrahedron Lett.* 1989, 30, 2129 b) *J. Chem. Soc. Perkin Trans.* 1 1991, 2757 c) *J. Chem. Soc. Perkin Trans.* II 1991, 657; and d) *Synthesis* (1999), 1594. Other methods for indole synthesis are described in Pindur, U.; Adam, R.; *J. Heterocyclic Chem.* 1988, 25, 1; or the book by Richard A. Sundberg The Chemistry of Indoles 1970 Academic Press London. Additional methods for the preparation of indole intermediates include the Leimgruber-Batcho Indole synthesis (R. D. Clark et. al. *Heterocycles*, 1984, 22, 195); the Fisher Indole synthesis (references: D. Hughes; *Organic Preparations and Procedures* 1993, 609; Guy, A. et.al *Synthesis* 1980, 222; or the 2,3-rearrangement protocol developed by Gassman (Gassman, P. G.; Van Bergen, T. J.; Gilbert, D. P.; Cue, B. W., Jr; *J. Am. Chem. Soc.* 1974, 96(17), 5495–508; the annelation of pyrroles (Muratake et.al. *Heterocycles* 1990, 31, 683); tin mediated cyclizations (Fukuyama, T. et. al. *J. Am. Chem. Soc.* 1994, 116, 3127); and the Larock palladium mediated cyclization of 2-alkynyl anilines. A method for the preparation of 2-substituted indoles is described in Hamel, P.; Zajac, N.; Atkinson, J. G.; Girard, Y.; *J. Org. Chem.* 1994, 59(21), 6372–6377.

Indole syntheses and methodology for manipulating and preparing 3-piperazine containing derivatives have been disclosed in two PCT patent applications (Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives. PCT Int. Appl. (2000), 165 pp. WO 0076521 Al and Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. PCT Int. Appl. (2002), WO 0204440 Al)These published applications describe methodology for flnctionalizing indoles which is hereby incorporated as available and instructive to someone skilled in the art. 1H-Indole-4-carboxylic acid methyl ester is commercially available and more than 900 4 carboxy esters of indoles with various substitution are found in Scifinder showing that a chemist skilled in the art would be able to prepare such derivatives with varied substitution ind order to prepare compounds of claim 1. Similarly, 1H-Indole-5-carboxylic acid methyl ester is commercially available and more than 1600 5-carboxy esters of indoles with various substitution are found in Scifinder and 1H-Indole-6-carboxylic acid methyl ester is also commercially available and more than 1000 6-carboxy esters of indoles with various substitution are found by searching the same source. 1H-Indole-7-carboxylic acid methyl ester is commercially available and more than 400 7-carboxy esters of indoles with various substitution are found in Scifinder. 1H-Indole-2-carboxylic acid methyl ester is commercially available and more than 8000 2-carboxy esters of indoles with various substitution are found in Scifinder.

As mentioned above, azaindoles may be prepared via the Bartoli reaction in which vinyl magnesium bromide reacts with a pyridine containing a nitro group, to form the five-membered nitrogen containing ring of the azaindole. Substituted azaindoles may be prepared by methods described in the literature or may be available from commercial sources. Syntheses of aza indoles include those described in the following references (a–k below): a) Prokopov, A. A.; Yakhontov, L. N. *Khim.-Farm. Zh.* 1994, 28(7), 30–51; b) Lablache-Combier, A. Heteroaromatics. Photoinduced Electron Transfer 1988, Pt. C, 134–312; c) Saify, Zafar Said. *Pak. J. Pharmacol.* 1986, 2(2), 43–6; d) Bisagni, E. *Jerusalem Symp. Quantum Chem. Biochem.* 1972, 4,439–45; e) Yakhontov, L. N. *Usp. Khim.* 1968, 37(7), 1258–87; f) Willette, R. E. *Advan. Heterocycl. Chem.* 1968, 9, 27–105; g) Mahadevan, I.; Rasmussen, M. *Tetrahedron* 1993, 49(33), 7337–52; h) Mahadevan, I.; Rasmussen, M. *J. Heterocycl. Chem.* 1992, 29(2), 359–67; i) Spivey, A. C.; Fekner, T.; Spey, S. E.; Adams, H. *J. Org. Chem.* 1999, 64(26), 9430–9443; j) Spivey, A. C.; Fekner, T.; Adams, H. *Tetrahedron Lett.* 1998, 39(48), 8919–8922; k) Advances in Heterocyclic Chemistry (Academic press) 1991, Vol. 52, pg 235–236 and references therein. Palladium catalyzed methods can be utilized for the introduction of the carboxylate moiety onto the indole or azaindole according to methods such as those described in Kondo, Y.; Yoshida, A.; Sakamoto, T.; *J. Chem. Soc., Perkin Trans* 1 1996, 19, 2331–2332; [Carbon monoxide, MeOH, $PdCl_2$, LiCl, $CH_3C(O)ONa$ trihydrate, triethylamine, $R^1 =(CH_3)_2NCH_2$]; Tollari, S.; et al.; *J. Organomet. Chem.* 1997, 527(1–2), 93; [palladium catalyst, MeOH, CO gas, 4 equivalents triethylamine, $R^1=(CH_3)_2NCH_2$]; or using 1) $Li_2PdCl_4$, $CH_3C(O)ONa$, ethanol; 2) methanol, CO, triethylamine and as depicted in Scheme I-7.

Scheme I-7

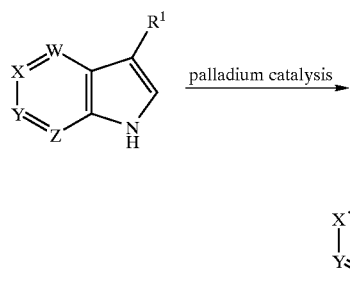

Azaindole syntheses and methods for preparing 3 position piperazine containing derivatives have been disclosed in a PCT patent application (Wang, Tao; Wallace, Owen B.; Zhang, Zhongxing; Meanwell, Nicholas A.; Bender, John A. Preparation of antiviral azaindole derivatives. PCT Int. Appl. (2001), WO 0162255 A1). This published application describes methodology for functionalizing azaindoles which is hereby incorporated as available and instructive to someone skilled in the art.

The synthesis of 1H-Pyrrolo[2,3-b]pyridine-2-carboxylic acid, methyl ester has been described in the literature by Davies et. al. PCT Patent Application (2002), WO 0208224 A1 and more than 34 2-carboxy esters of such azaindoles with various substitution are found in Scifinder.

The synthesis of 1H-Pyrrolo[2,3-b]pyridine-4-carboxylic acid, methyl ester has been described in the literature by Allegretti et. al. Synlett (2001), (5), 609–612.

The synthesis of 1H-Pyrrolo[3,2-c]pyridine-6-carboxylic acid, ethyl ester has been described in the literature by Biere et. al. Liebigs Ann. Chem. (1987), (6), 491–4.

1H-Pyrrolo[2,3-c]pyridine-5-carboxylic acid, methyl ester has been described by Dodd et. al. in PCT patent application (1992) WO 9221680 A1 and the similar esters with additional substituents have also been described in the literature and can be found with Scifinder.

The following references describe additional methodologies for converting indoles to indole carboxylate esters via formation of anions and subsequent trapping with either carbon dioxide or other ester precursors such as chloroformates or alkyl cyano formates. One such method is described in Sundberg, R. J.; Broome, R.; Walters, C. P.; Schnur, D.; *J. Heterocycl. Chem.* 1981, 18, 807 and is carried out as depicted below in Scheme I-8 for indole derivatives in which W, X, Y, and Z are $CR^3$, $CR^4$, $CR^5$, and $CR^6$, respectively. This chemistry can also be employed to prepare azaindole-2-carboxylates, wherein one of W, X, Y, and Z is $NR^{10}$, according to methods described in Desarbre, E.; Coudret, S.; Meheust, C.; Merour, J.-Y.; *Tetrahedron* 1997, 53(10), 3637–3648.

Scheme I-8

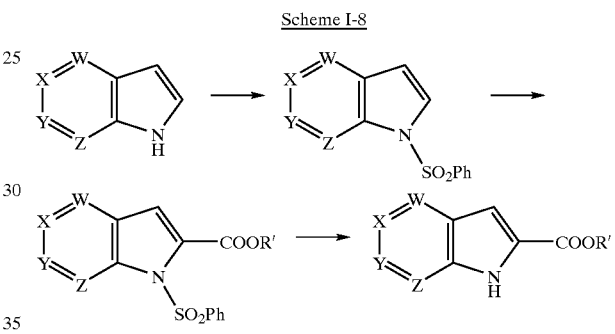

A method for installing a carbomethoxy group using a Grignard reagent, carbon dioxide, and diazomethane is shown below in Scheme I-9 and may be carried out according to procedures described in *J. Organomet. Chem.* 1997, 527(1–2), 93–102.

Scheme I-9

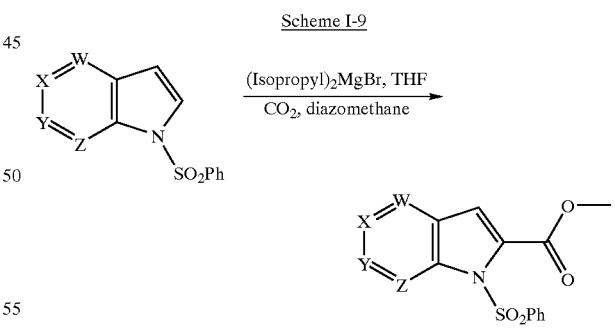

A method for the introduction of a carbomethoxy group at the 2 position of a 1-methoxyindole or 1-methoxyazaindole is shown below in Scheme I-10. The reaction may be accomplished by treating the 1-methoxyindole or 1-methoxyazaindole with a strong base, such as n-butyl lithium, in an aprotic solvent, such as tetrahydrofuran, and then reacting the anion thus generated with methyl carbonate. The conditions employed are as further described in *Heterocycles* 1991, 32(2), 221–227.

Scheme I-10

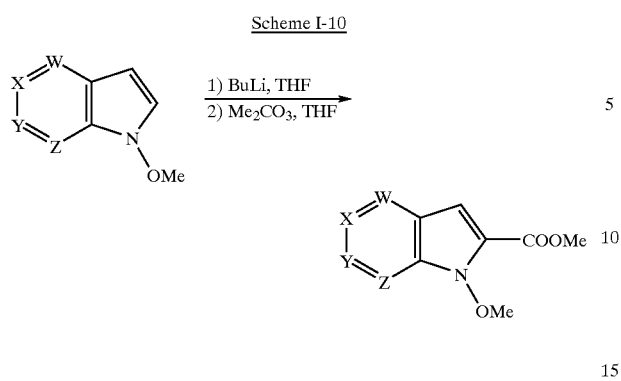

The preparation of 2-carboxymethyl-3-methyl(aza)indole derivatives is depicted in the Scheme I-11 below and may be accomplished according to the procedure as described in *Synth. Commun.* 1988, 18(10), 1151–65. Other references which utilize anion formation and trapping to generate indole and azaindole carboxylates include Kawasaki, T.; Kodama, A.; Nishida, T.; Shimizu, K.; Somei, M.; *Heterocycles* 1991, 32(2), 221–227; and Katritzky, A. R.; Akutagawa, K.; Jones, R. A.; *Synth. Commun.* 1988, 18(10), 1151–65.

Scheme I-11

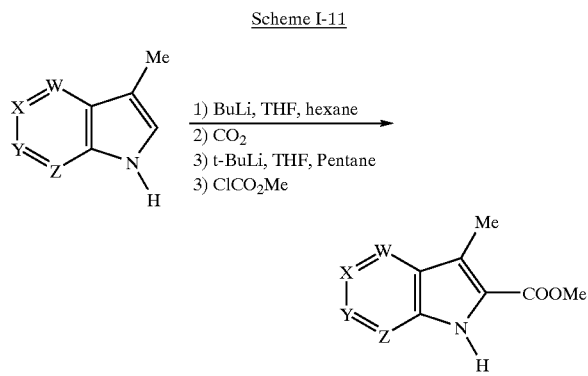

Fukuda, T.; Maeda, R.; Iwao, M.; *Tetrahedron* 1999, 55(30), 9151–9162 describes methodology for protecting the indole or azaindole nitrogen with a directing group, functionalizing the 7-position, and then subsequently removing the protecting group from the indole or azaindole nitrogen. This method can be used to install a carboxylate ester or acid derivative at C-7 as depicted in the Scheme I-12 below. These C-7 derivatives provide a handle which can then be converted to almost any functional group or can be reacted with an appropriate cyanomethyl piperazine derivative using methods described herein for Schemes 1, 1A and 2 to provide compounds of formula I.

Scheme I-12

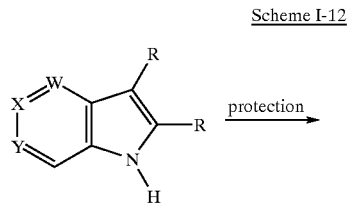

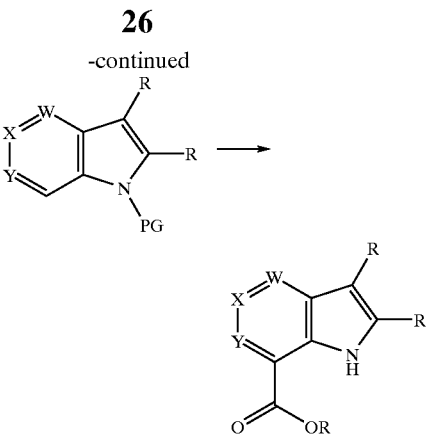

Schemes I-13, and I-14 depict the preparation of benzisoxazole or azabenzisoxazole carboxylates which can serve as useful intermediates for the synthesis of compounds of Formula I using the methods described herein for Schemes 1, 1A, and 2. Scheme I-13 depicts a general method for converting 2-hydroxybenzoic acid derivatives or the corresponding pyridine derivatives (where one of W, X, Y, and Z is N) to the corresponding benzisoxazole carboxylate. Step e of Scheme I-13 can be carried out by treating the acid with sulfuric acid in methanol as described in *Can. J. Chem.* 1988, 66(6), 1405–1409 to provide the methyl glyoxylate derivative. Alternatively, Step e may be accomplished by first treating the hydroxy acid derivative with thionyl chloride, then with sodium cyanide and tetrabutylammonium bromide, and then with hydrochloric acid and water to provide the glyoxylic acid which may then be esterified under standard conditions to provide the glyoxylate derivative. Step f of Scheme I-13 may be accomplished by treating the methyl glyoxylate derivative with hydroxylamine hydrochloride in an appropriate solvent such as ethanol. The oxime derivative thus obtained may then be converted to the corresponding (aza)benzisoxazole upon treatment with either tricloroacetylisocyanate or thionyl chloride as shown in Step g and as further described in *Heterocycles* 1987, 26(11), 2921.

Scheme I-13

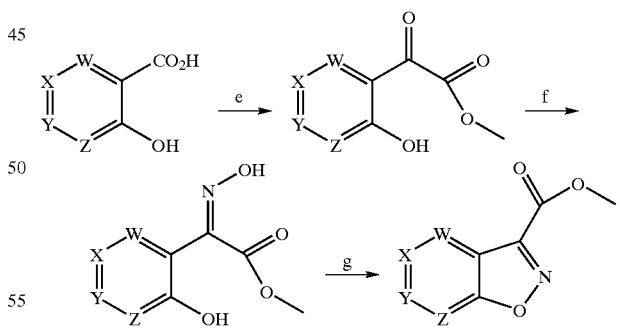

Scheme I-14 shows the synthesis of methyl-7-methoxy-4-azabenzisoxazole-3-carboxylate. Steps a–d of Scheme I-14 were accomplished as described by Shimano, M. et al. in *Tetrahedron* 1998, 54, 12745–12774 at page 12750. Step a of Scheme 1–14 was carried out by O-alkylation of 3-hydroxypyridine with methoxymethyl chloride in tetrahydrofuran-dimethylformamide in the presence of potassium tertiary-butoxide as base. The methoxymethyl ether was then brominated as shown in Step b by treatment with tertiary-butyllithium and 1,2-dibromotetrafluoroethane in diethyl ether at −78° C. The bromide was converted to the corresponding methoxy derivative as shown in Step c by treatment with sodium methoxide in methanol. The carboxylic acid was then prepared as shown in Step d by treatment with tertiary-butyllithium followed by dry ice (CO$_2$) in tetrahydrofuran at −78° C. and then quenching the reaction with aqueous hydrochloric acid. Steps e, f, and g were then carried out according to the same methods described for Steps e, f, and g of Scheme I-13.

Scheme I-14

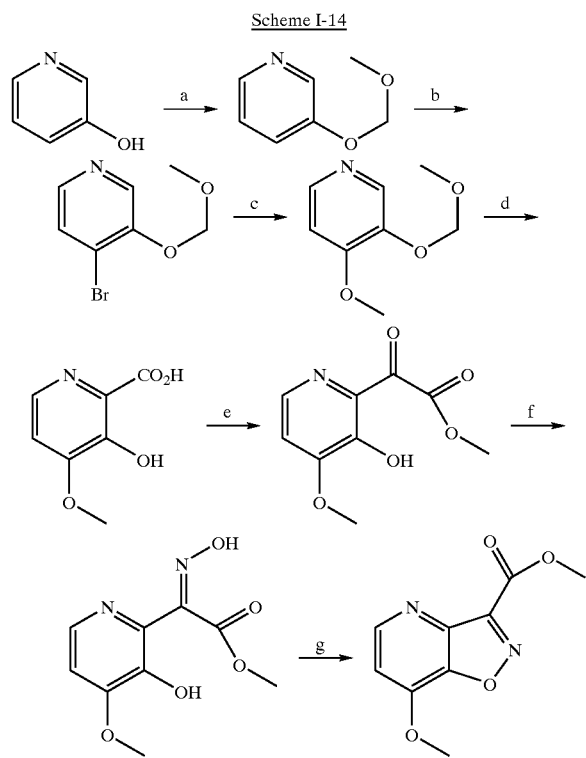

Alternative reaction schemes which may be used to prepare benzisoxazole intermediates useful for the preparation of compounds of Formula I are shown in Scheme I-14-2. The 3-hydroxypyridine may be iodinated in step a according to the method described in *J. Med. Chem.* 1974, 17, 1065. The iodo derivative may then be converted to the cyano derivative as shown in step b according to the method described in *Heterocycles* 1987, 26(11), 2921 followed by conversion to the acetyl derivative as depicted in step c according to the method described in *Chem. Pharm. Bull.* 1977, 25, 1150. The acetyl derivative may then be converted to the corresponding methyl oxalate derivative upon treatment with selenium dioxide and pyridine followed by treatment with diazomethane according to the method described in *Tetrahedron Lett.* 1994, 35(48), 8955–6. Steps f and g of Scheme I-14-2 can then be carried out as described previously for Scheme I-14.

Scheme I-14-2

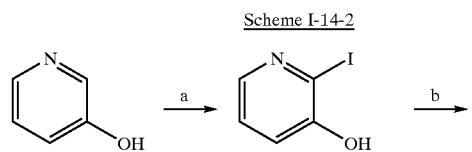

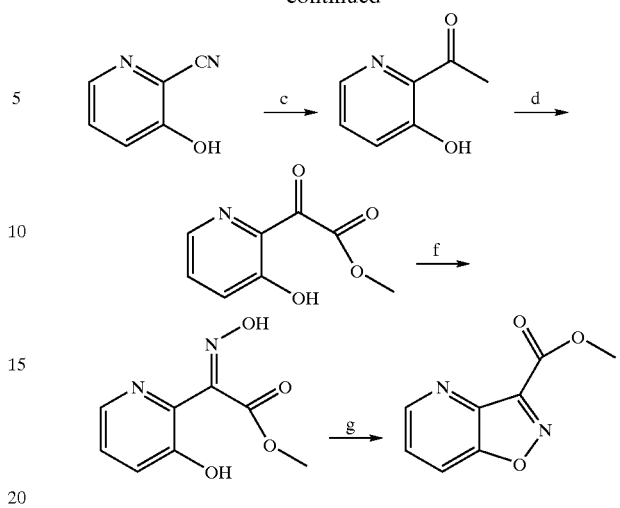

Scheme I-14-3 depicts an alternative method which may be used to prepare azabenzisoxazole derivatives such as 7-methoxy-4-azabenzisoxazole. 3-hydroxy-4-methoxypridine is iodinated as shown in step a according to the procedure described in *J. Med. Chem.* 1974, 1 7, 1065. The methyl oxalate side chain may then be introduced using the palladium catalyzed method as described in *J. Mol. Catal.* 1986, 34(3), 317–319 as shown in step b. The methyl oxalate can then be reacted with hydroxyl amine and subsequently cyclized as depicted and previously described for steps f and g in Schemes I-14 and I-14-2.

Scheme I-14-3

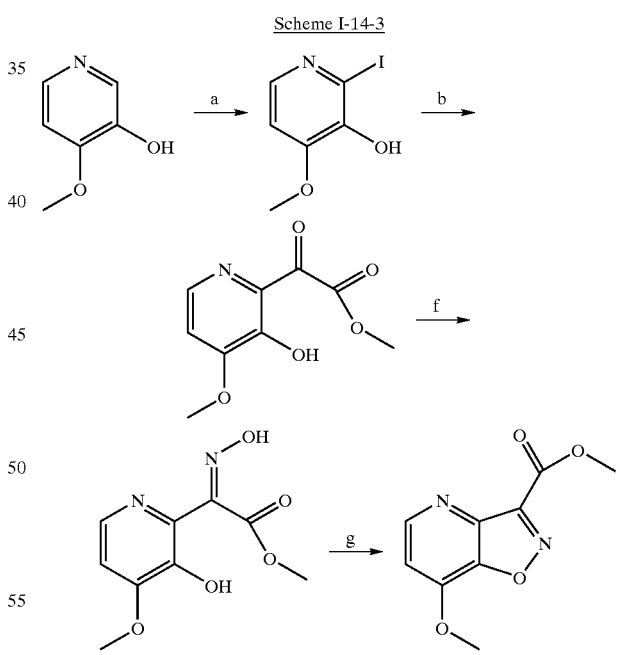

Heterocyclic carboxylates may also be prepared from a heterocycle which contains an exocyclic methyl group as shown in Scheme I-15. Step a of Scheme I-15 depicts the bromination of the exocyclic methyl group which may be carried out according to the method as described in *J. Med. Chem.* 1997, 40, 2706–2725 by heating a mixture of the compound of formula QCH$_3$ with N-bromosuccinimide and benzoyl peroxide in a suitable solvent such as carbon tetrachloride. The bromomethyl heterocycle of formula QCH₂Br can then be converted to the hydroxymethyl heterocycle of formula QCH₂OH by treatment with potassium superoxide as shown in Step b. The heterocyclic carboxylate of formula QCO₂CH₃ can then be prepared from the hydroxymethyl derivative by Swern oxidation of the hydroxymethyl derivative followed by treatment with silver nitrate in methanol and then treatment with diazomethane in a mixture of diethylether and tetrahydrofuran as depicted in Step c of Scheme I-15. Alternatively, the bromomethyl heterocycle can be converted directly to the heterocyclic carboxylate as shown in Step d of Scheme I-15 by treatment with 1.2 equivalents of pyridine N-oxide followed by treatment with silver nitrate in methanol and then treatment with diazomethane in a mixture of diethylether and tetrahydrofuran.

Scheme I-15

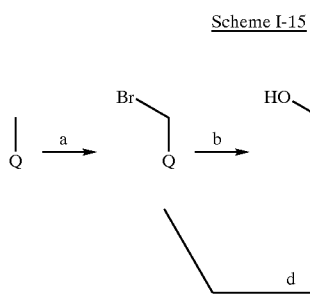

Scheme I-16 depicts the preparation of methyl (aza) benzisoxazole-3-carboxylates which were prepared according to the methods as previously described for the corresponding Steps a–d of Scheme I-15. The heterocyclic carboxylates prepared by the methodology described in Schemes I-15 and I-16 may then be used to prepare compounds of Formula I according to the methods as described herein in Schemes 1, 1A, and 2.

Scheme I-16

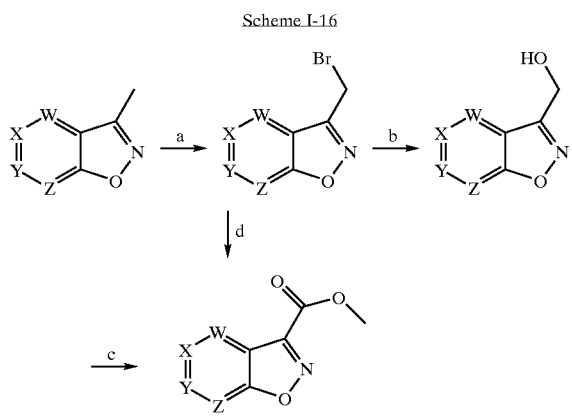

Scheme I-16-2 depicts the preparation of a 3-methyl-4-azabenzisoxazole ti derivative which may be used as starting material for Scheme I-16. Steps a, b, AP and c of equation 1 may be carried out as previously described for Scheme I-14-2. The acetyl derivative may then be treated with hydroxylamine to provide the oxime as depicted in step d and then cyclized as depicted in step e (as described for steps f and g of Scheme I-14, respectively) to provide the 3-methyl-4-azabenzisoxazole shown. In equation 2 of Scheme I-16-2 the 3-hydroxy-4-methoxypyridine is first acetylated (step a) then is treated with hydroxylamine and cyclized as previously described to provide 3-methyl-7-methoxy-4-azabenzisoxazole.

Scheme I-16-2

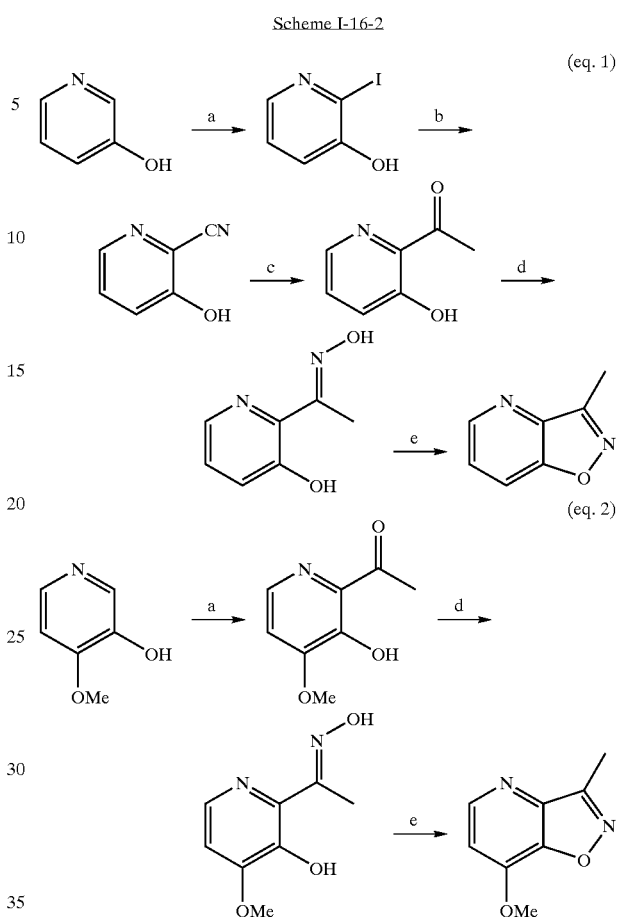

Scheme I-17 depicts the preparation of methyl 4-methoxybenzofuran-3-carboxylate which can then be used to prepare compounds of Formula I using the methods described for Schemes 1, 1A, and 2. 1,3-Cyclohexanedione is treated with aqueous potassium hydroxide, followed by bromopyruvic acid in methanol and then with hydrochloric acid to provide the furan carboxylic acid derivative shown. The furan carboxylic acid derivative is then treated with 10% palladium on carbon and 1-dodecene in refluxing decalin to provide 3-carboxy-4-hydroxybenzofuran. The 3-carboxy-4-hydroxybenzofuran may then be converted to the corresponding methoxy methyl ester derivative by treatment with methyl iodide and potassium carbonate in dimethylsulfoxide at approximately 60° C. Alternatively, the same transformation may be carried out by treatment with diazomethane in tetrahydrofuran/diethyl ether at room temperature. The benzofuran derivative can then be used to prepare compounds of Formula I according to the methods described hereinafter for Schemes 1, 1A and 2.

Scheme I-17

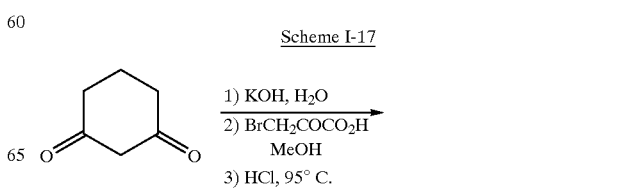

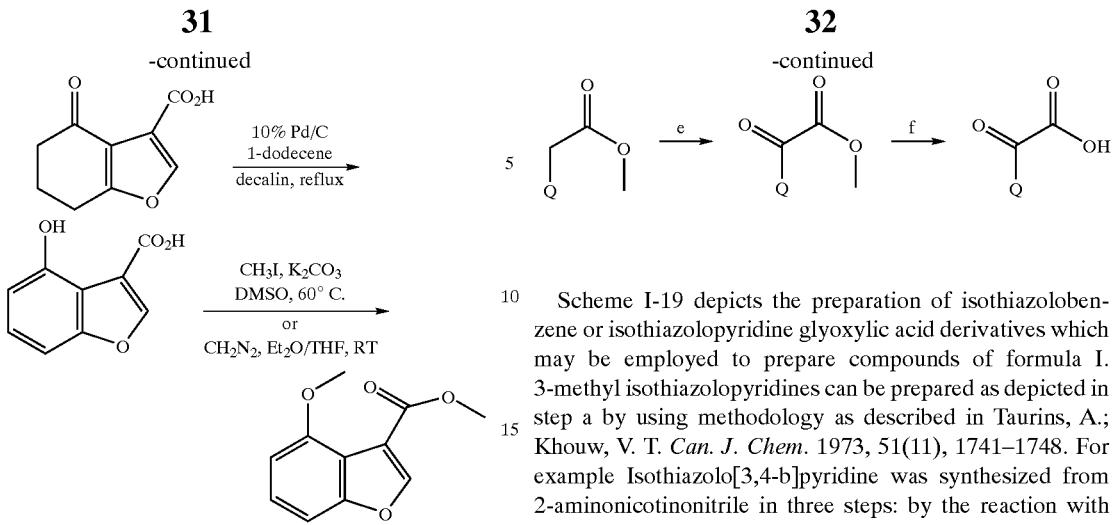

Scheme I-18 shows the preparation of glyoxylic acid intermediates which can serve as useful intermediates for the preparation of compounds of Formula I. The methyl group of methyl containing heterocycle of formula QCH₃ may be converted to the bromide with N-bromosuccinimide as shown in step b. Suitable conditions for the bromination include those as described in *J. Med. Chem.* 1997, 40, 2706–2725 and carried out by heating a mixture of QCH₃ with N-bromosuccinimide and benzoyl peroxide in carbon tetrachloride. Bromide displacement with cyanide, as shown in step c, can be carried out by heating a mixture of the bromide with either copper cyanide or potassium cyanide in either dimethylformamide or aqueous ethanol to provide the nitrile. Hydrolysis of the nitrile followed by esterification, as shown in step d, provides the methyl ester. Acidic or basic hydrolysis of the nitrile may be employed. Esterification of the resulting acid may be carried out under standard conditions or using a reagent such as diazomethane. Oxidation of the methyl ester to the oxalate can then be carried out as depicted in step e. The oxidation can be carried out in one step with selenium dioxide to provide the oxalate. Alternatively, the methyl ester can be treated with a strong base such as lithium bistrimethylsilyl amide in tetrahydrofuran at reduced temperature followed by camphorsulfonyl oxaziridine to provide the corresponding α-hydroxy ester which may be oxidized with the Dess-Martin reagent in order to obtain the oxalate. The oxalate may then be hydrolyzed under standard conditions as depicted by step f to provide the oxalic acid derivative. The oxalic acid derivative may then be coupled to an appropriate piperazine derivative to provide a compound of Formula I. It is to be understood that the methyl acetate derivative of formula QCH₂CO₂CH₃ prepared from step d may also be hydrolyzed to provide the acetic acid derivative of formula QCH₂CO₂H which may then also be coupled to an appropriate piperazine derivative to provide a compound of Formula I.

Scheme I-19 depicts the preparation of isothiazolobenzene or isothiazolopyridine glyoxylic acid derivatives which may be employed to prepare compounds of formula I. 3-methyl isothiazolopyridines can be prepared as depicted in step a by using methodology as described in Taurins, A.; Khouw, V. T. *Can. J. Chem.* 1973, 51(11), 1741–1748. For example Isothiazolo[3,4-b]pyridine was synthesized from 2-aminonicotinonitrile in three steps: by the reaction with NH₃ and H₂S to produce 2-aminothionicotinamide; oxidative cyclization with H₂O₂ to give 3-amino-isothiazolo[3,4-b]pyridine, followed by diazotization and reduction with hypophosphorous acid. 3-Aminoisothiazolo[4,3-b]pyridine was prepared in a similar way from 3-aminopicolinonitrile via 3-aminothiopicolinamide. Isothiazolo[5,4-b]pyridine was synthesized from 2-chloronicotinonitrile in three steps: reduction with HCO₂H in the presence of Raney Nickel to obtain 2-chloronicotinaldehyde; transformation of the latter into 2-thiocyanonicotinaldehyde; and cyclization with NH₃ to obtain isothiazolo[5,4-b]pyridine. 3-Methylizothiazolo[5,4-c]pyridine was prepared by cyclization of 4-acetyl-3-thiocyanopyridine with NH₃. Alternatively, the 3-methylisothiazolopyridines may be prepared as described in Chimichi, S.; Giomi, D.; Tedeschi, P. *Synth. Commun.* 1993, 23(1), 73–78 in a single step procedure by treating a cyanomercaptopyridine with methyllithium in an appropriate solvent such as tetrahydrofuran to provide the 3-methylisothiazolopyridine derivative. As described previously for Scheme I-18 the methyl group may be converted to the bromide with N-bromosuccinimide as shown in step b. Bromide displacement with cyanide, as shown in step c, followed by hydrolysis and esterification, as shown in step d, provides the methyl ester. Oxidation of the methyl ester to the oxalate can then be carried out as depicted in step e. The oxidation can be carried out in one step with selenium dioxide to provide the oxalate. Alternatively, the methyl ester can be treated with a strong base such as lithium bistrimethylsilyl amide in tetrahydrofuran at reduced temperature followed by camphorsulfonyl oxaziridine to provide the corresponding α-hydroxy ester which may be oxidized with the Dess-Martin reagent in order to obtain the oxalate. The oxalate may then be hydrolyzed under standard conditions as depicted by step f to provide the oxalic acid derivative. The oxalic acid derivative may then be coupled to an appropriate piperazine derivative to provide a compound of Formula I.

Scheme I-18

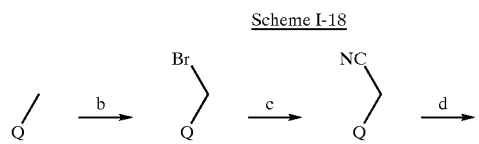

Scheme I-19

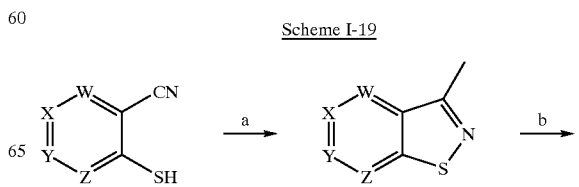

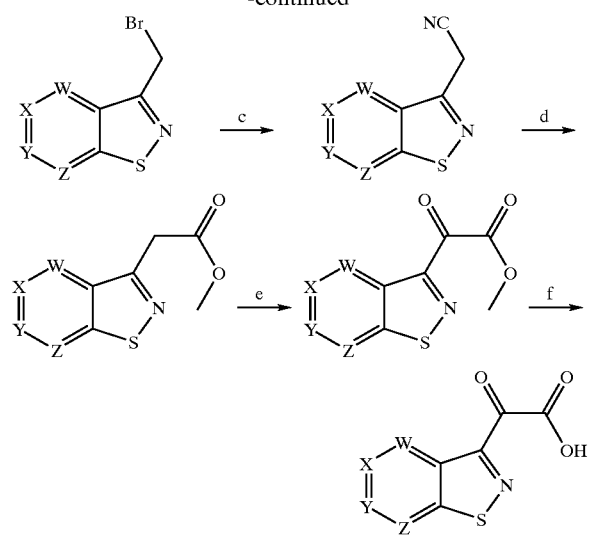

Scheme I-20 provides another example of the preparation of a glyoxylic acid intermediates suitable for the preparation of a compound of Formula I. The methods employed are the same as previously described for the corresponding steps in Schemes I-18 and I-19. R represents a lower alkyl group, preferably methyl or ethyl. The hydroxylation of the ester, as shown in step d, may be carried out using lithium bistrimethylsilylamide and 10-camphorsulfonyl oxaziridine or alternatively by treatment with bromine followed by potassium acetate and 18-crown-6 in acetonitrile followed by column chromatography purification on silica and finally treatment with 5% sodium carbonate, methanol at approximately 65° C. The α-hydroxy ester may then be oxidized as depicted in step e with the Dess-Martin reagent or with pyridinium dichromate or chromium trioxide pyridine complex to provide the glyoxylate which can then be hydrolyzed under standard conditions as shown in step f to provide the glyoxylic acid derivative.

Scheme I-20

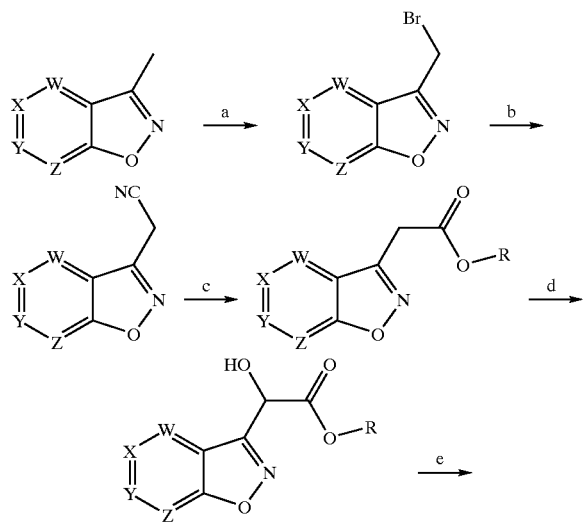

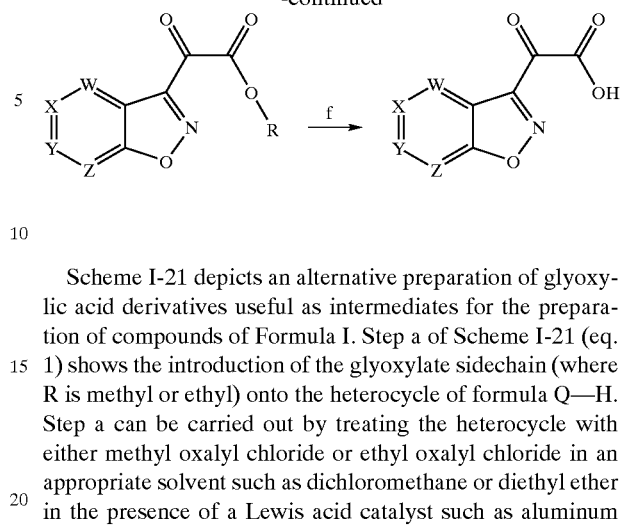

Scheme I-21 depicts an alternative preparation of glyoxylic acid derivatives useful as intermediates for the preparation of compounds of Formula I. Step a of Scheme I-21 (eq. 1) shows the introduction of the glyoxylate sidechain (where R is methyl or ethyl) onto the heterocycle of formula Q—H. Step a can be carried out by treating the heterocycle with either methyl oxalyl chloride or ethyl oxalyl chloride in an appropriate solvent such as dichloromethane or diethyl ether in the presence of a Lewis acid catalyst such as aluminum trichloride to provide the glyoxylate, QC(O)CO$_2$R. The glyoxylate ester can then be hydrolyzed as depicted in steb b by treating the glyoxylate with aqueous base, such as sodium hydroxide or potassium hydroxide, in a suitable solvent such as ethanol or methanol, followed by acidification to provide the glyoxylic acid derivative, QC(O)CO$_2$H. 37 The usual conditions employ methanolic or ethanolic sodium hydroxide followed by acidification with aqueous hydrochloric acid of varying molarity but 1M HCl is preferred. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of −70° C. to the boiling point of the solvent may be employed but −10° C. is preferred. Other conditions for ester hydrolysis are listed in: Protective groups in organic synthesis 3rd ed./Theodora W. Greene and Peter G. M. Wuts. New York: Wiley, 1999 and both this reference and many of the conditions for ester hydrolysis are well known to chemists of average skill in the art. Equation 2 of Scheme I-21 depicts the glyoxylation at the 3-position of the heterocycle and is carried out according to the methods described for equation 1. The glyoxylic acid derivatives may then be coupled with appropriately substituted piperazine derivatives of formula H—TC(O)A to provide compounds of Formula I.

Scheme I-21

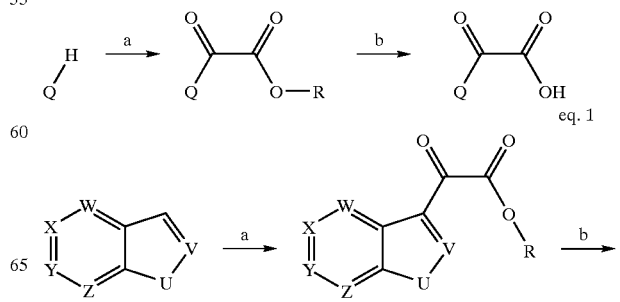

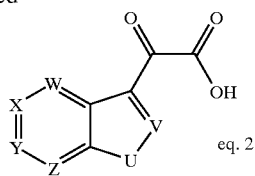

eq. 2

Scheme I-22 shows the preparation of glyoxylic acid chloride derivatives which are also useful intermediates for the preparation of compounds of Formula I. The glyoxylic acid chloride derivative of formula QC(O)C(O)Cl can be prepared by treating an appropriate heterocycle of formula Q—H with oxalyl chloride in an appropriate solvent such as diethyl ether in the presence of an appropriate Lewis acid catalyst such as aluminum trichloride. Equation 2 depicts the introduction of the glyoxylic acid chloride side chain at the 3-position of the heterocycle using the method described for equation 1. The glyoxylic acid chloride derivatives can then be reacted with an appropriately substituted piperazine derivative of formula H—TC(O)A in an appropriate solvent such as tetrahydrofuran or acetonitrile in the presence of a suitable base such as diisopropylethylamine or pyridine to provide compounds of formula I. Additional methodology for attaching the —C(O)C(O)TC(O)A moiety to an appropriate heterocycle is described in WO-0076521 published by the World Patent Office on Dec. 21, 2000.

Scheme I-22

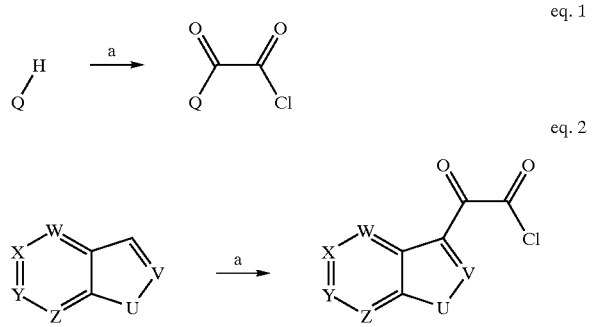

The following heterocycles, which exemplify compounds which may serve as useful intermediates for the preparation of compounds within the scope of Formula I. These compounds may be converted to compounds within the scope of Formula I using the methods described herein or known in the art.

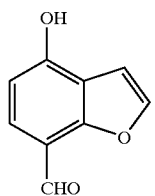

Compounds with oxygenated functionality at position 4 and an aldehyde handle at position 7 of a benzofuran, such as the benzofuran derivative shown above, have been prepared as shown by L. Rene et. al. in *Bull. Chim. Fr.* 1975, (11–12 Pt.2), 2763–6. The phenolic hydroxy can be converted to a methyl ether with diazomethane or iodomethane and KOH in DMSO. The aldehyde at position 7 can be transformed to numerous other functionalities. The compounds may then be converted to compounds of Formula I by methods described herein.

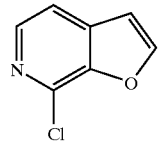

7-chloro-6-azaindole can be prepared as described in Eur. Pat. Application EP 737685 published in 1996 by Viaud and coworkers. A preparation is also described in S. Shiotani and H. Morita *J. Heterocyclic Chem.* 1982, 19, 1207. It can be converted to compounds of Formula I using the chemistry in Sheme 4C. The chloro group can be substituted to install alkoxy groups, heterocycles, cyano, amido, or aryl groups using methodology described below.

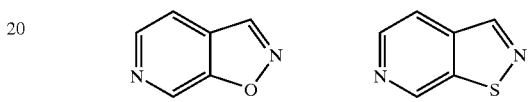

The 6-azabenzisoxazole shown above can be prepared as described in Heterocycles, 1982, 19 (8), 1511–15 by A. Comparini and coworkers. It can be converted to compounds of this invention using the chemistry as described in Schemes 4, 4A, and 4B. The preparation of the 6-azabenzisothiazole shown above has also been described in the literature. The related 6-azabenzisoxazole or 6-azabenzisoxazole derivatives which contain a chloro group in the six membered ring can be substituted to install alkoxy groups, heterocycles, cyano, amido, or aryl groups using methodology described below.

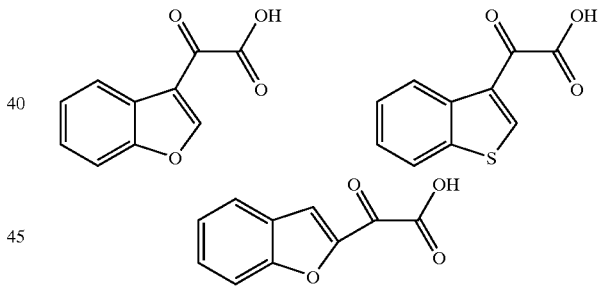

The three oxalic acid derivativess shown above or their corresponding acid chlorides have been described in the literature and methods for coupling to amines has been described by Da Settimo, F. et. al. in *Eur J. Med. Chem.* 1996, 31, 951–956. Methods for preparing these compounds are referenced in this paper and thus could be applied to more substituted benzothiophenes or benzofurans. These benzofuran or benzothiophene derivatives may then be coupled with an appropriately substituted piperazine derivative according to the conditions described herein for Scheme 3 to provide compounds within Formula I.

Indazoles may be prepared from indoles or azaindoles in a single step as described in Han-Cheng Zhang, *J. Med. Chem.* 2001, 44, 1021–1024. The resulting aldehyde may be oxidized with PCC, silver carbonate, buffered NaClO$_2$, CrO3 in sulfuric acid, or Jones reagent. The acid may be esterified with diazomethane or MeOH, HCl to provide an ester. The esters can be converted to the compounds of this invention using the alpha cyano piperazine methodology described elsewhere in the patent. Alternatively, the acid may be decarboxylated and the indazole analogs converted to the desired dicarbonyl derivatives as described elsewhere in this patent application for indazoles.

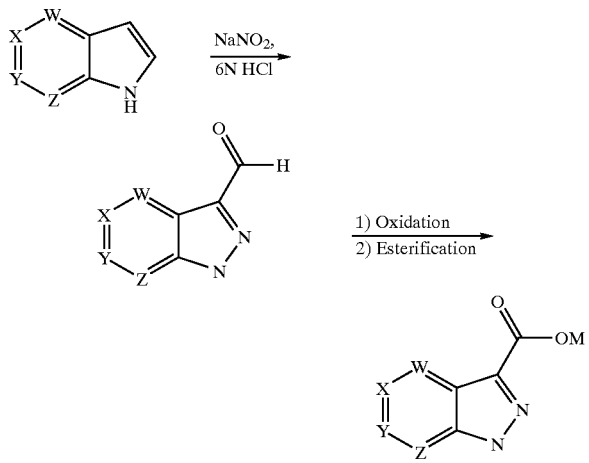

The synthesis of 1H-Indazole-6-carboxylic acid, methyl ester ester has been described in the literature in seven different references and one example is Batt et. al. J. Med. Chem. (2000), 43(1), 41–58.

The synthesis of 1H-Indazole-4-carboxylic acid, methyl ester has been described in the literature in three different references and one example is Batt et. al. J. Med. Chem. (2000), 43(1), 41–58.

The synthesis of 1H-Indazole-5-carboxylic acid, ethyl ester has been described in the literature in four different references and one example is Batt et. al. J. Med. Chem. (2000), 43(1), 41–58.

1H-Indazole-3-carboxylic acid, ethyl ester is commercially available. Similar esters with additional substitution are described in the literature.

Preparation of Compounds of Formula I

Scheme 1 depicts a general method suitable for the synthesis of many of the compounds of formula I. As shown in Scheme 1, a suitable protected piperazine derivative, PG-TH, of Formula VI, (wherein PG is an appropriate amine protecting group) is acylated with an appropriate acylating agent, AC(O)L, (wherein L is a suitable leaving group) to provide the protected acylated piperazine derivative of Formula V. Compound V is then deprotected using standard methods to provide the acylated piperazine derivative of Formula IV. For example, when PG represents tertiary-butoxycarbonyl the compound of Formula V can be deprotected to provide a compound of Formula IV by treatment with a strong acid, such as trifluoroacetic acid or hydrochloric acid, in an appropriate solvent such as dichloromethane. Alternatively, when PG represents benzyl the deprotection may be effected by hydrogenation. The acylpiperazine derivative of Formula IV is then alkylated with 2-chloroacetonitrile in the presence of an appropriate base, such as triethylamine, 4-methylmorpholine or diisopropylethyl amine in an appropriate solvent, such as THF, to provide the cyanomethyl acylpiperazine derivative of Formula III. Reaction of a heterocyclic derivative of formula II (wherein $L^1$ is an appropriate leaving group, such as $OCH_3$) with an anion of the cyanomethyl acylpiperizine of Formula III, provides cyanomethyl amide derivative of Formula Ia. Oxidation of the cyanomethyl amide derivative of Formula Ia to a ketoamide derivative of Formula Ib is carried out preferentially using a peracid such as meta-chloroperoxybenzoic acid (mCPBA). The cheap and simple oxidant sodium hypochlorite solution (common bleach) is also useful.

Other peracids could also be utilized for the oxidation of a compound of Formula Ia to a compound of Formula Ib, including peroxy acetic acid generated in situ. Other methods for oxidation are shown in Table A which describes a one pot condensation/oxidation process which is usually preferred:

TABLE A

Oxidation Conditions

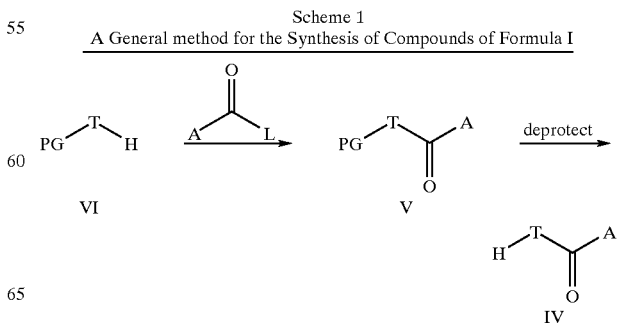

mCPBA (1 eq.)
mCPBA (1.5 eq.)
mCPBA (2 eq.)
Oxone
(2 eq.,with $H_2O$)
$H_2O_2$ (2 eq., 30% in $H_2O$)
$H_2O_2$-Urea
(2 eq.)
AcOOH (2 eq., 32% in AcOH)
Clorox ™
(2 eq., 5.25% NaOCl)

Compounds of Formula II can be esters, preferably methyl esters, however other simple alkyl esters or activated acid derivatives such as acid chlorides, acid anhydrides, or Weinreb amides could also find utility in preparing compounds as shown.

Scheme 1
A General method for the Synthesis of Compounds of Formula I

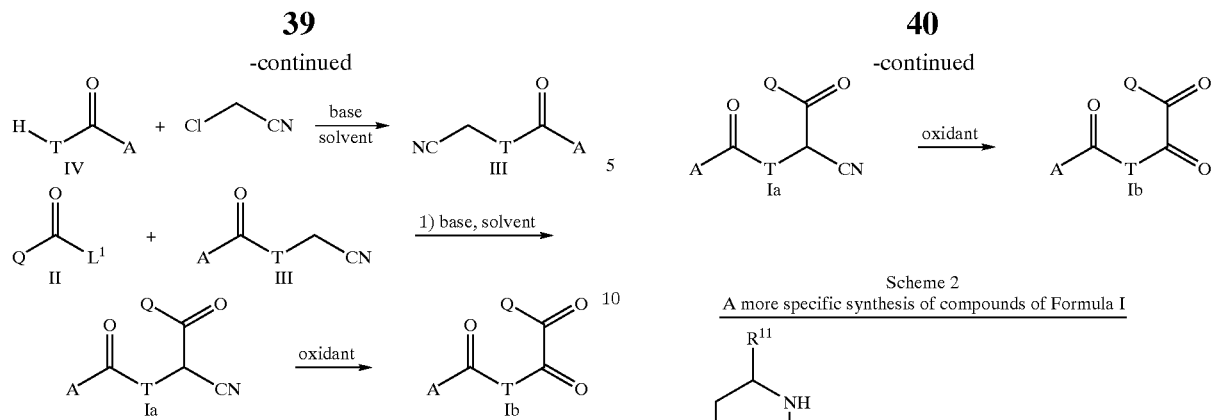

A general literature reference for some of the chemistry depicted in Scheme 1 is Takahashi, K.; Shibasaki, K.; Ogura, K.; Iida, H.; *Chem Lett.* 1983, 859.

Schemes 1 through 9 describe general reaction schemes for preparing various compounds of Formula I. While these schemes are very general, other permutations such as carrying a precursor or precursors to substituents $R^1$ through $R^7$ through the reaction scheme and then converting it to a compound of Formula I in the last step are also contemplated methods of this invention. Nonlimiting examples of such strategies follow in subsequent schemes. Scheme 1A depicts a general method suitable for the synthesis of many of the compounds of Formula I using the methodology described for Scheme 1. As shown in Scheme 1, a piperazine derivative of formula IV may be alkylated with chloroacetonitrile in the presence of a suitable base, such as triethylamine, in an appropriate aprotic solvent, such as tetrahydrofuran, to provide a cyanomethylpiperazine derivative of formula III. Other tertiary amine bases such as 4-methylmorpholine may also be used in this step. Reaction of a suitable heterocyclic carboxylate ester of formula II with an anion of a cyanomethyl piperazine derivative provides cyanomethyl esters of formula Ia. The anion of the cyanomethyl piperazine derivative can be generated by treating a solution of the cyanomethyl piperazine derivative with an appropriate base, such as sodium hexamethyldisilazide (NaHMDS). The esters of formula II are preferably methyl esters but other simple alkyl esters or activated acid derivatives such as acid chlorides, acid anhydrides, or Weinreb amides could also find utility. Oxidation of the alpha cyano ketone of Formula Ia to a ketoamide of Formula Ib is carried out preferentially using a peracid oxidant such as meta-chloroperoxybenzoic acid. Other peracids may be useful for the oxidation of Ia to Ib, including peroxy acetic acid generated in situ. A general literature reference for some of the chemistry depicted in Scheme 1 is Takahashi, K.; Shibasaki, K.; Ogura, K.; Iida, H.; *Chem Lett.* 1983, 859.

Scheme 1A
A General method for the Synthesis of Compounds of Formula I

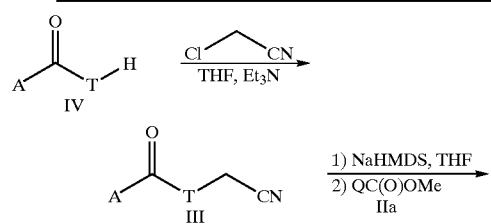

Scheme 2
A more specific synthesis of compounds of Formula I

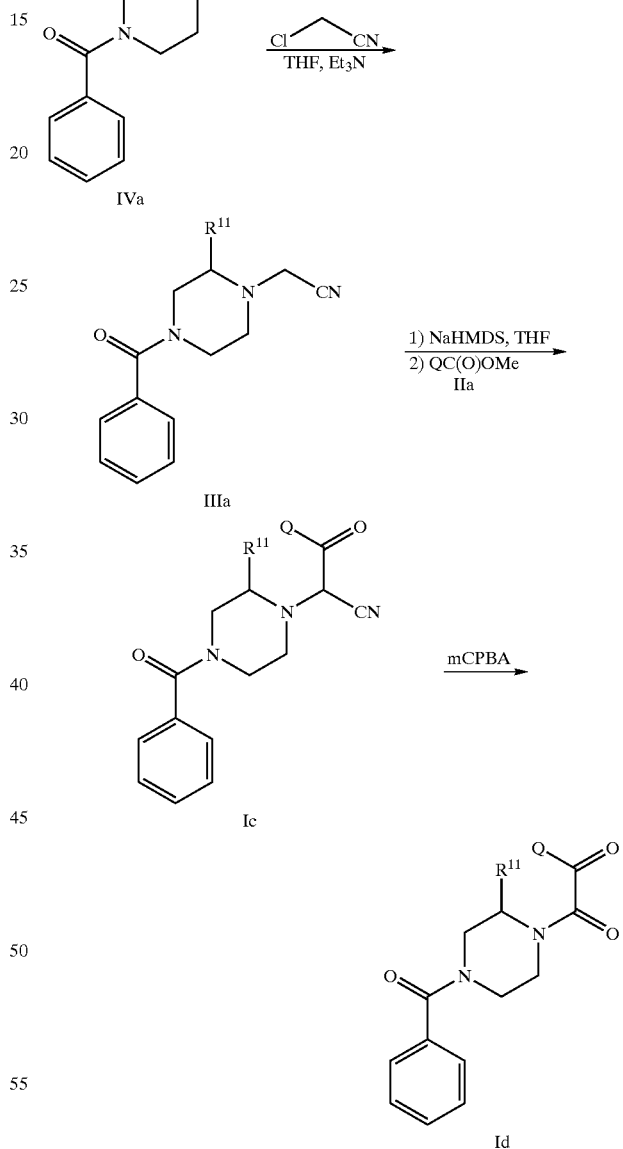

Scheme 2 provides a further example of the synthesis of compounds of Formula I according to the route previously described in Schemes 1 and 1A. The benzoylpiperazine derivative of Formula IVa is first alkylated with 2-chloroacetonitrile in tetrahydrofuran in the presence of triethylamine to provide the cyanomethyl derivative of Formula IIIa. The anion of the cyanomethyl derivative is then generated by treating the intermediate of Formula IIIa with sodium hexamethyldisilazide (NaHMDS) in an aprotic solvent such as tetrahydrofuran. The anion thus generated is then reacted with the heterocyclic carboxylate intermediate of Formula IIa to provide the (2-oxo-1-cyanoethyl) benzoylpiperazine derivative of Formula Ic. The compound of Formula Ic may then be oxidized using an appropriate oxidant, such as 3-chloroperoxybenzoic acid (mCPBA) to provide compounds of Formula Id.

Alternatively, as shown in Scheme 3 below, compounds of formula Ib can be prepared by reaction of a heterocyclic glyoxylic acid derivative of Formula VII (QC(O)CO$_2$H), with a piperazine derivative of Formula IV (HTC(O)A), under standard peptide coupling conditions to provide compounds of Formula Ib. Standard peptide coupling refers to coupling an amine with a carboxylic acid in the presence of an amine acid coupling reagent such as DCC, PyBop, EDC, or DEPBT. The preparation of DEPBT is described by Li, H.; Jiang, X.; Ye, Y.-H.; Fan, C.; Romoff, T.; and Goodman, M. in *Organic Lett.*, 1999, 1, 91–93.

The group T as referred to herein is either

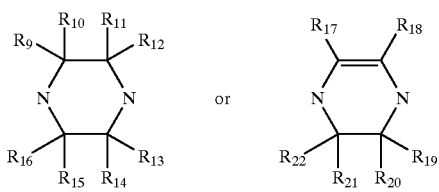

One preferred method for carrying out this reaction is to use the reagent 3-(diethoxyphosphoryloxy)-1,2,3-benzotriazin-4(3H)-one (DEPBT) and an amine HTC(O)A in DMF as solvent containing a tertiary amine such as diisopropylethylamine. Another preferred method is to use the reagent 1-(3-Dimethylaminopropyl)-3-ethylcarbodiimide hydrochloride in an appropriate solvent and in the presence of diisopropylethylamine. Typical stoichiometries are given in the specific examples but these ratios may be modified. The amide bond construction reactions depicted in Scheme 3 could be carried out using the specialized conditions described herein or alternatively by applying the conditions or coupling reagents for amide bond construction described in the literature. Some specific non-limiting examples are given in this application.

Scheme 3
Glyoxylic acid method for preparation of compounds of Formula Ib

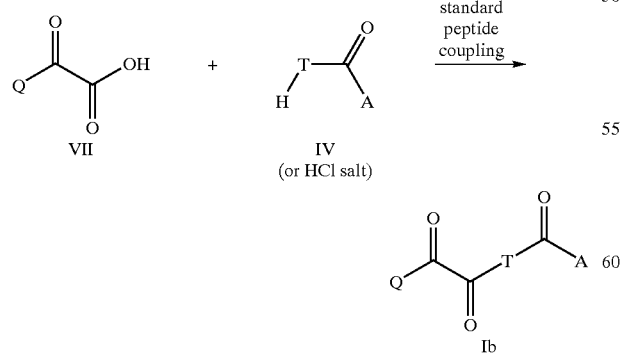

Another method for the synthesis of compounds of Formula Ib is shown in Scheme 4, below. The hydrolysis of the heterocyclic oxoacetic acid ester intermediate of Formula VIII, to form the heterocyclic oxoacetic acid of Formula VII, is shown in Step 1 of Scheme 4. The usual conditions employ methanolic or ethanolic sodium hydroxide followed by acidification with aqueous hydrochloric acid of varying molarity but 1M HCl is preferred. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of −70° C. to the boiling point of the solvent may be employed but −10° C. is preferred. Other conditions for ester hydrolysis are well known to chemists of average skill in the art. It is to be understood that these hydrolysis conditions are applicable to other regioisomeric heterocyclic oxoacetic acid esters. The glyoxylic acid derivative of Formula VII may then be converted to a compound of Formula Ib directly as described in Scheme 3, above. Alternatively, as Step 2 of Scheme 4 depicts, the glyoxylic acid derivative of Formula VII can be converted to the corresponding glyoxylic acid chloride of Formula IX. This transformation can be carried out using thionyl chloride, reaction with oxalyl chloride, or other methods well known in the art. Alternatively, the intermediates of Formula IX can also be obtained as described previously for Scheme I-22. Coupling of the piperazine derivative, H—T—C(O)A to the intermediate glyoxylic acid chloride of Formula IX, may be carried out in a basic solvent such as pyridine or triethylamine, or in an inert solvent in the presence of pyridine as base or other tertiary amine bases to provide compounds of Formula Ib. Schotten-Baumann conditions could also be employed for this coupling (aqueous base).

Scheme 4
Glyoxylic acid chloride method

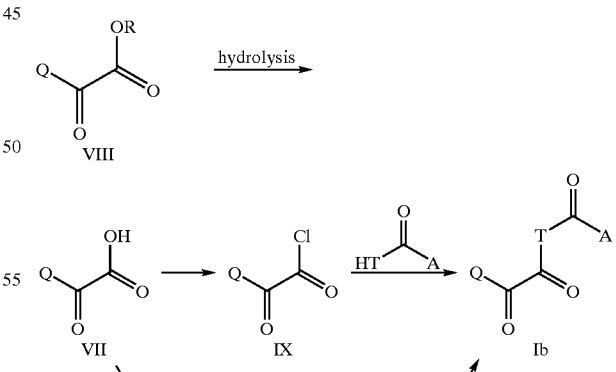

Scheme 4A provides a further depiction of routes used to prepare compounds of the invention. In equation 1, an appropriate heterocycle is treated with oxalyl chloride in the presence of a Lewis acid catalyst, such as aluminum trichloride, in an aprotic solvent such as diethyl ether. The intermediate heterocyclic oxalyl chloride derivative may then be coupled to the piperazine derivative of Formula HTC(O)A in the presence of a suitable base, such as diisopropylethylamine (Hunig's base) to provide compounds within Formula I. Alternatively, the heterocycle may be treated with ethyl oxalyl chloride or methyl oxalyl chloride in the presence of a Lewis acid catalyst, such as aluminum trichloride, in an appropriate aprotic solvent such as dichloromethane, to provide the corresponding heterocyclic oxalate (step a of eq. 2). The oxalate may then be hydrolyzed (step b of eq. 2) to provide the corresponding oxalic acid derivative which can then be coupled to the piperazine derivative of formula HTC(O)A using the conditions shown (step c of eq. 2) or other standard peptide coupling methods as previously described.

Scheme 4A

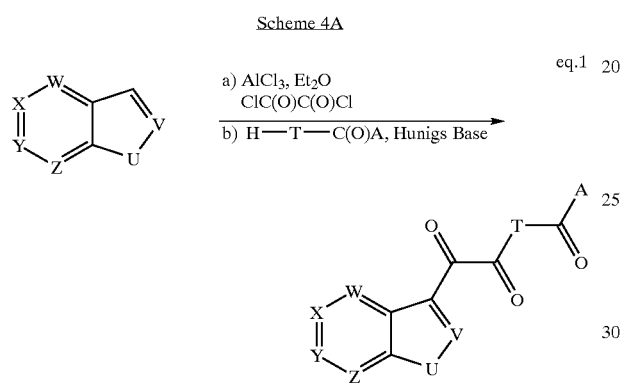

eq.1

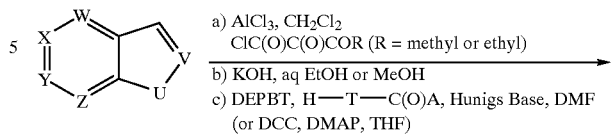

eq.2

Scheme 4B, below, depicts the preparation of benzofuran derivatives within the scope of Formula I, using the methods described above for Schemes 4 and 4A. The starting benzofuran derivatives can be prepared according to the methods described by Hertel, L. et al. in PCT Appl. WO 0000198 (for example where $R^3$ is F and $R^6$ is $CH_3$).

Scheme 4B

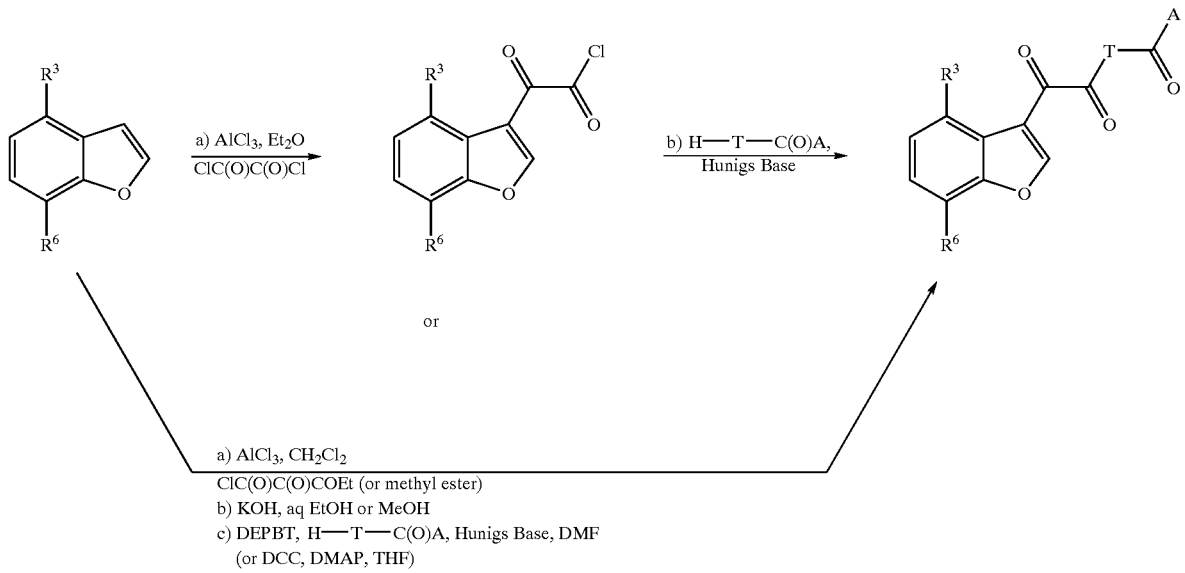

Scheme 4C, equation 1, below, depicts the preparation of an azabenzofuran derivative within the scope of Formula I according to the methods previously described for Schemes 4, 4A and 4B. The starting 7-chloro-4-azabenzofuran was prepared as described by Shiotani, S. et al. in *J. Heterocyclic Chem.* 1996, 33, 1051. The chloro group can then be converted to an aryl or heteroaryl substituent by using methods well known in the art, such as the Suzuki coupling or Stille coupling as depicted in equation 2. Typical conditions which may be used for the Suzuki or Stille type couplings are described subsequently for equations 4–6 of Scheme 6.

α-hydroxyamide of Formula If, with an oxidant, such as Dess-Martin reagent, will provide the desired α-ketoamides of formula Ib.

An alternative route which may be used to obtain the α-ketoamides of Formula Ib involves the direct oxidation of the acetamide derivative of Formula Ie. A preferred method is to treat the acetamide derivative of Formula Ie with an oxidant, such as selenium dioxide ($SeO_2$) in a polar solvent such as dioxane to provide the desired α-ketoamides of formula Ib.

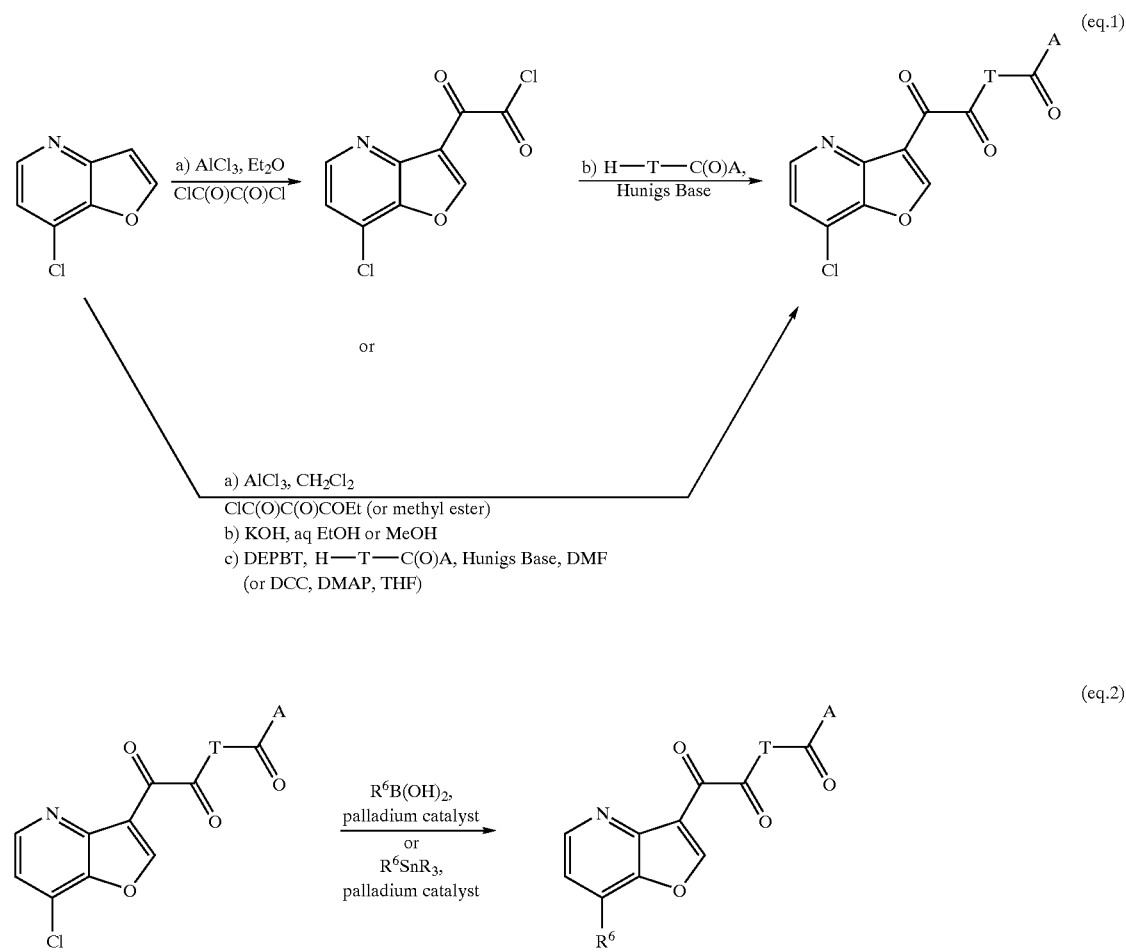

An alternate method (three step procedure) for preparing compounds of Formula I is shown in Scheme 5, below. Reaction of a known or synthesized heterocyclic acetic acid derivative of Formula X with a piperazine derivative of Formula IV, under standard peptide coupling conditions will afford the desired amides of Formula Ie. Preferred peptide coupling conditions include the use of EDC in the presence of diisopropylethylamine. Treatment of the amide derivative, Ie, with a strong base, such as lithium diisopropylamide (LDA), followed by quenching with (+,-)-Davis' reagent will afford the corresponding α-hydroxyamide derivatives of formula If. Finally, oxidation of the

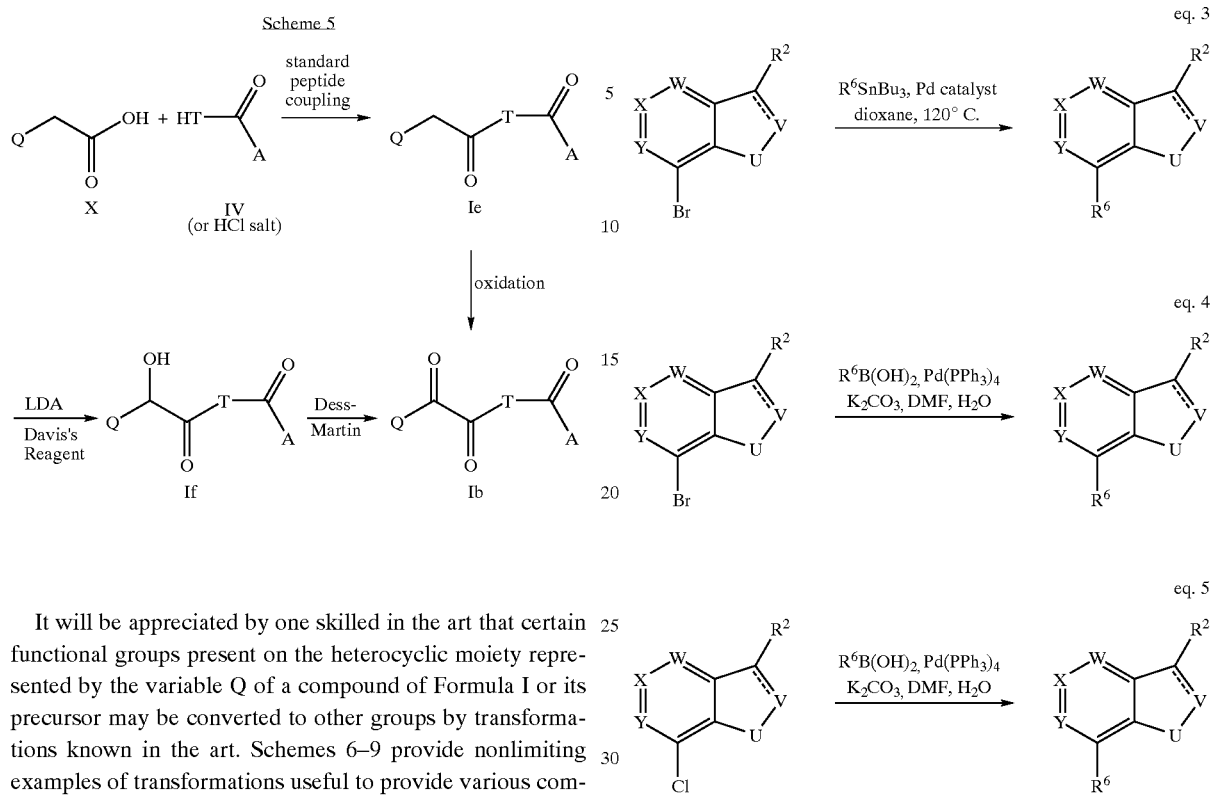

It will be appreciated by one skilled in the art that certain functional groups present on the heterocyclic moiety represented by the variable Q of a compound of Formula I or its precursor may be converted to other groups by transformations known in the art. Schemes 6–9 provide nonlimiting examples of transformations useful to provide various compounds of Formula I. In Schemes 6–9 various functional group transformations are shown for the $R^6$ position of the heterocyclic moiety represented by Q in the general formula (with the point of attachment being at one of positions $R^1$–$R^5$). It is to be understood that the same functional group conversions may be applicable to any of the $R^1$–$R^6$ positions of the heterocyclic moiety (other than the $R^1$–$R^6$ position which is the point of attachment). The transformations depicted in Schemes 6–9 are applicable to both intermediates which can then be converted to compounds of Formula I and to compounds of Formula I.

Scheme 6

Conversion of halides:

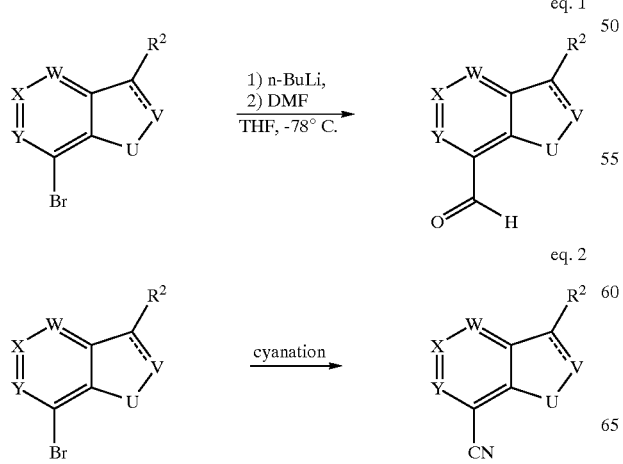

Scheme 6, above, depicts the conversion of a bromide to various other functional groups. In equation 1, treatment of the bromide with a strong base, such as n-butyl lithium, in an aprotic solvent, such as THF, followed by treatment with dimethylformamide results in the aldehyde shown.

Equation 2 of Scheme 6 depicts the conversion of the bromide to the cyano derivative. This transformation can be achieved by treating the bromide with a reagent such as sodium cyanide, copper cyanide or zinc cyanide in a solvent such as dimethylformamide.

Equations 3 and 4 of Scheme 6 show a suitable bromo derivative may undergo metal mediated couplings with various stannanes or boronic acid derivatives. Conditions for the Stille-type coupling, shown in equation 3, are well known in the art and involve treatment of the bromide (or iodide or triflate) with an aryl, heteroaryl or vinyl stannane in the presence of an appropriate palladium catalyst in an appropriate solvent. Palladium catalysts used include, but are not limited to, tetrakis-triphenylphosphine palladium and palladium (II) acetate. Appropriate solvents include, but are not limited to, polar solvents such as dioxane and 1-methyl-2-pyrrolidinone. Numerous examples of conditions for carrying out the Stille reaction may be found in references such as Farina, V.; Roth G. P.; Adv. Met.-Org. Chem. 1996, 5, 1–53; Farina, V.; Krishnamurthy, V.; Scott, W. J.; Org. React. (N.Y.) 1997, 50, 1–652; and Stille, J. K.; Angew. Chem. Int. Ed. Engl. 1986, 25, 508–524.

Equation 4 of Scheme 6 depicts the Suzuki-type coupling of the bromide with an appropriate boronic acid derivative. Appropriate boronic acid derivatives include aryl and heteroaryl boronic acid derivatives. This transformation may be carried out in the presence of an appropriate palladium catalyst, such as tetrakis-triphenylphosphine palladium, and a base, such as potassium carbonate, in a solvent or solvent mixture such as dimethylformamide and water. Typical reaction conditions for carrying out the Suzuki-type reaction can be found in Miyaura, N.; Suzuki, A.; Chem. Rev. 1995, 95, 2457.

Alternative methods are available to one skilled in the art for carrying out transformations analogous to those shown in equations 3 and 4 of Scheme 6. For example, substituted azabenzoxazoles or other heterocyclic groups of general formula Q containing a chloride, bromide, iodide, triflate, or phosphonate undergo coupling reactions with a boronate (Suzuki type reactions) or a stannane to provide the corresponding substituted heterocycles. Triflates and boronates are prepared via standard literature procedures from the corresponding hydroxy bearing heterocycle. The substituted heterocyles may undergo metal mediated coupling to provide compounds of Formula I wherein $R^6$ is aryl, heteroaryl, or heteroalicyclic for example. The bromoheterocycle intermediates, (or heterocyclic triflates or iodides) may undergo Stille-type coupling with heteroarylstannanes as shown in equation 3. Conditions for this reaction are well known in the art and the following are three example references a) Farina, V.; Roth, G. P. Recent advances in the Stille reaction; Adv. Met.-Org. Chem. 1996, 5, 1–53. b) Farina, V.; Krishnamurthy, V.; Scott, W. J. The Stille reaction; Org. React. (N.Y.) 1997, 50, 1–652. and c) Stille, J. K. Angew. Chem. Int. Ed. Engl. . 1986, 25, 508–524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art to carry out transformations such as those depicted in equation 3 and 4 of Scheme 6. It can be well recognized that a heterocyclic stannane could also be coupled to a heterocyclic or aryl halide or triflate to construct compounds of Formula I. Suzuki coupling (Norio Miyaura and Akiro Suzuki Chem Rev. 1995, 95, 2457.) between a bromo heterocycle intermediate and a suitable boronate could also be employed.

Suzuki couplings between chloroheterocycle intermediates, as depicted in equation 5 of Scheme 6, are also feasible. If standard conditions fail new specialized catalysts and conditions can be employed. Some references (and the references therein) describing catalysts which are useful for coupling with aryl and heteroaryl chlorides are: Littke, A. F.; Dai, C.; Fu, G. C. J. Am. Chem. Soc. 2000, 122(17), 4020–4028; Varma, R. S.; Naicker, K. P. Tetrahedron Lett. 1999, 40(3), 439–442; Wallow, T. I.; Novak, B. M. J. Org. Chem. 1994, 59(17), 5034–7; Buchwald, S.; Old, D. W.; Wolfe, J. P.; Palucki, M.; Kamikawa, K.; Chieffi, A.; Sadighi, J. P.; Singer, R. A.; Ahman, J PCT Int. Appl. WO 0002887 2000; Wolfe, J. P.; Buchwald, S. L. Angew. Chem., Int. Ed. 1999, 38(23), 3415; Wolfe, J. P.; Singer, R. A.; Yang, B. H.; Buchwald, S. L. J. Am. Chem. Soc. 1999, 121(41), 9550–9561; Wolfe, J. P.; Buchwald, S. L. Angew. Chem., Int. Ed. 1999, 38(16), 2413–2416; Bracher, F.; Hildebrand, D.; Liebigs Ann. Chem. 1992, 12, 1315–1319; and Bracher, F.; Hildebrand, D.; Liebigs Ann. Chem. 1993, 8, 837–839.

Alternatively, the boronate or stannane may be formed on the heterocyclic moiety via methods known in the art and the coupling performed in the reverse manner with aryl or heteroaryl based halogens or triflates.

Methods for direct addition of aryl or heteroaryl organometallic reagents to alpha chloro nitrogen containing heterocyles or the N-oxides of nitrogen containing heterocycles are known and applicable to the compounds described herein. Some examples are Shiotani et. al. J. Heterocyclic Chem. 1997, 34(3), 901–907; Fourmigue et.al. J. Org. Chem. 1991, 56(16), 4858–4864.

Scheme 7, below, depicts various transformations of a carboxylic acid group at the $R^6$ position. In equation 1, the carboxylic acid group is being converted to an amide by using standard peptide coupling techniques. Standard peptide coupling refers to coupling an amine with a carboxylic acid in the presence of an amine acid coupling reagent such as DCC, PyBop, EDC, or DEPBT.

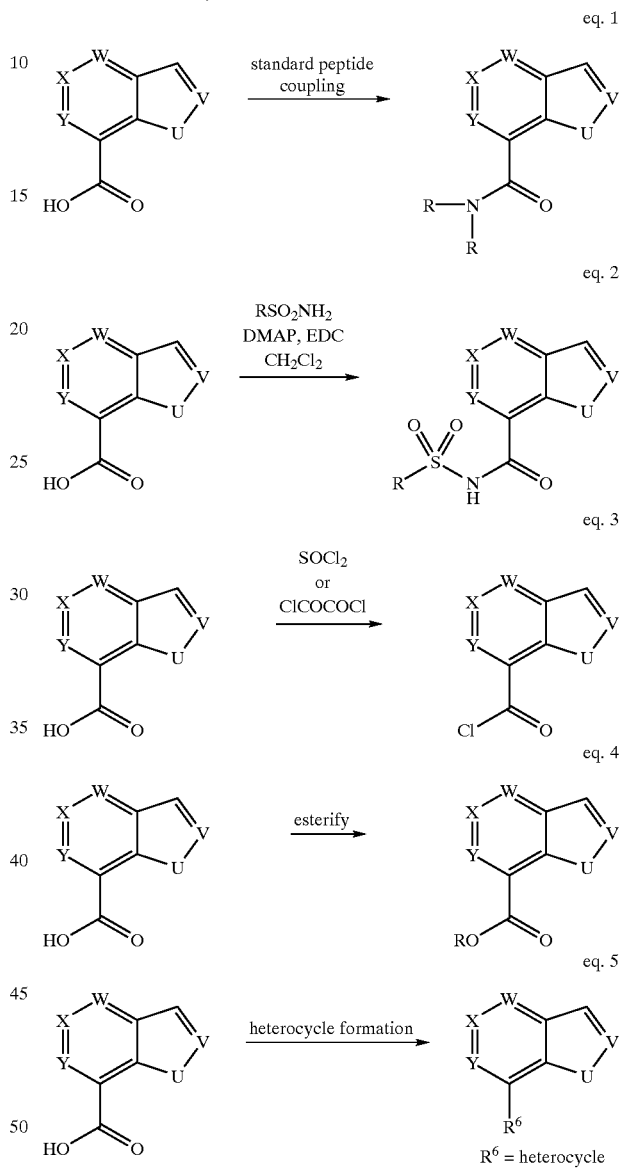

Equation 2 of Scheme 7 shows the conversion of the carboxylic acid group to an acylsulfonamide group by treating the carboxylic acid with a primary sulfonamide, such as methylsulfonamide or phenylsulfonamide in the presence of a peptide coupling agent, such as EDC, and a base, such as DMAP, in an appropriate aprotic solvent, such as dichloromethane.

The carboxylic acid group can also be converted to the corresponding acid chloride by treatment with thionyl chloride (neat or in an inert solvent) or oxalyl chloride in an inert solvent such as benzene, toluene, THF or dichloromethane as shown in equation 3 of Scheme 7. The acid chloride may then be further reacted, for example with an excess of ammonia, primary amine or secondary amine in an inert solvent such as benzene, toluene, THF or dichloromethane to provide the corresponding amides. The acid chloride may also be reacted with a stoichiometric amount of amine in the presence of a base, such as triethylamine, 4-methylmorpholine, 2,6-lutidine or pyridine. Alternatively, the acid chloride may be reacted with an amine under basic conditions (usually sodium hydroxide or potassium hydroxide) in solvent mixtures containing water and possibly a miscible cosolvent such as dioxane or THF.

The carboxylic acid group can also be esterified, as shown in equation 4 of Scheme 7, using standard conditions well known in the art. For example, the acid may be converted to the methyl ester by treatment with diazomethane or trimethylsilyldiazomethane in methanol/benzene. Other standard esterification conditions, such as those described by Richard C. Larock in Comprehensive Organic Transformations $2^{nd}$ Ed. 1999, John Wiley and Sons, New York or Theodora W. Greene and Peter G. M. Wuts in Protective Groups in Organic Synthesis $3^{rd}$ Ed. 1999, Wiley, New York may also be used.

Equation 5 of Scheme 7 shows the acid being used as a versatile precursor for the formation of various heterocycles. The acid could be converted to hydrazonyl bromide and then a pyrazole via methods described by Shawali in *J. Heterocyclic Chem.* 1976, 13, 989. One method for general heterocycle synthesis would be to convert the acid to an alpha bromo ketone by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions described by Hulton et al. in *Synth. Comm.* 1979, 9, 789 to react the alpha bromo ketone would provide oxazoles. Reaction of the alpha bromoketone with urea via the methods described by Pattanayak, B. K. et al. in *Indian J. Chem.* 1978, 16, 1030 would provide 2-amino oxazoles. The alpha bromoketone could also be used to generate furans using beta keto esters as described in *Chemische Berichte* 1902, 35, 1545 and *Chemische Bericte* 1911, 44, 493; pyrroles (from beta dicarbonyls as in *Indian J. Chem.* 1973, 11, 1260; thiazoles by Hantsch methods as described by Roomi et al in *Can. J. Chem.* 1970, 48, 1689; or isoxazoles and imidazoles as described by Sorrel, T. N. in *J. Org. Chem.* 1994, 59, 1589. Coupling of the aforementioned acid chloride with N-methyl-O-methyl hydroxyl amine would provide a "Weinreb Amide" which could be used to react with alkyl lithiums or Grignard reagents to generate ketones. Reaction of the Weinreb anion with a dianion of a hydroxyl amine would generate isoxazoles as in Nitz, T. J. et al. *J. Org. Chem.* 1994, 59, 5828–5832. Reaction with an acetylenic lithium or other carbanion would generate alkynyl indole ketones. Reaction of this alkynyl intermediate with diazomethane or other diazo compounds would give pyrazoles as in Bowden, K. et al. *J. Chem. Soc.* 1946, 953. Reaction with azide or hydroxyl amine would give heterocycles after elimination of water. Nitrile oxides would react with the alkynyl ketone to give isoxazoles as described in Chimichi, S. *Synth. Comm.* 1992, 22, 2909. Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles as described by Scholkopf et al. in *Angew. Int. Ed. Engl.* 1971, 10(5), 333. These could be converted to amines, alcohols, or halides using standard reductions or Hoffman/Curtius type rearrangements.

Equation 1 of Scheme 8 depicts the oxidation of an heterocyclic aldehyde to the corresponding carboxylic acid. Numerous methods are suitable for the conversion of an aldehyde to an acid and many of these are well known in the art and described in standard organic chemistry texts such as Richard C. Larock in Comprehensive Organic Transformations $2^{nd}$ Ed. 1999, John Wiley and Sons, New York. One preferred method is the use of silver nitrate or silver oxide in aqueous or anhydrous methanol at a temperature of about 25° C. or as high as reflux for 1 to 48 hours. Alternatively, the aldehyde could be oxidized to the acid using other standard oxidants such as $KMnO_4$ or $CrO_3/H_2SO_4$.

Equation 2 of Scheme 8 depicts the reaction of the aldehyde with hydroxylamine (R=H) or a hydroxylamine derivative (R=alkyl or substituted alkyl) in a suitable solvent, such as ethanol to provide the oximes shown.

Scheme 8

Conversion of aldehydes:

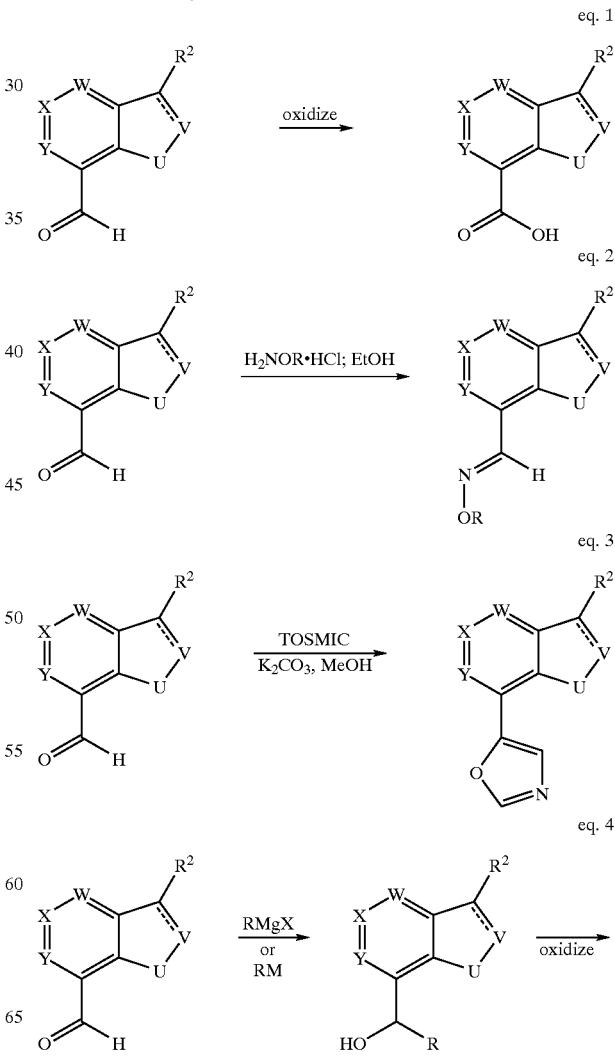

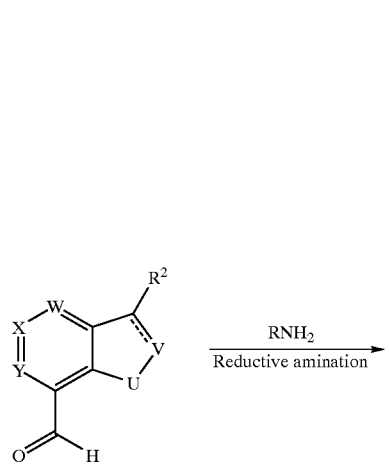

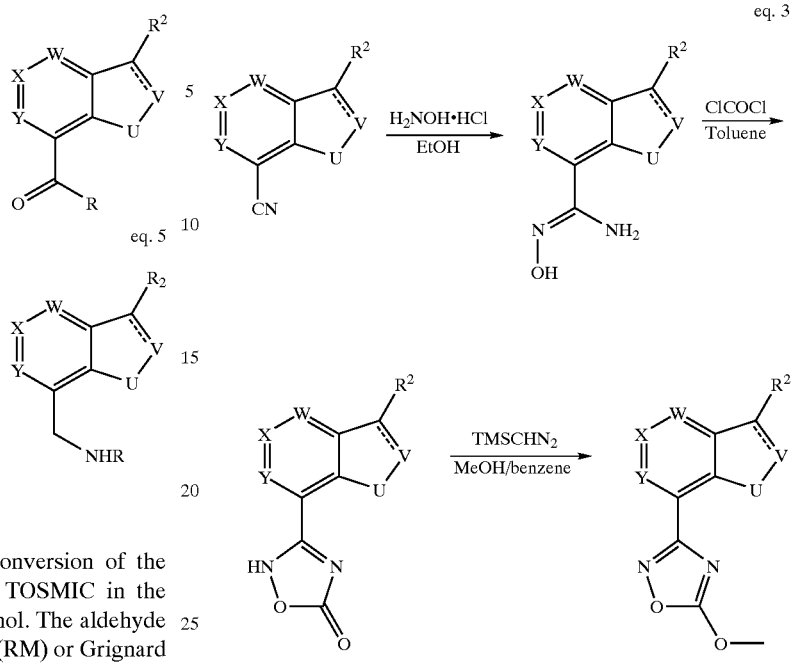

Equation 3 of Scheme 8 shows the conversion of the aldehyde group to an oxazole by using TOSMIC in the presence of potassium carbonate in methanol. The aldehyde could also be reacted with a metal reagent (RM) or Grignard reagent (RMgX, X=halide) to generate secondary alcohols which could then be oxidized to the corresponding ketones as shown in equation 4 of Scheme 8. Suitable Grignard reagents would include reagents wherein R is alkyl, aryl or heteroaryl. The oxidation of the secondary alcohols to the corresponding ketones, shown as the second step in equation 4, may be accomplished using oxidants such as TPAP, $MnO_2$ or PCC.

Scheme 9
Conversion of nitriles:

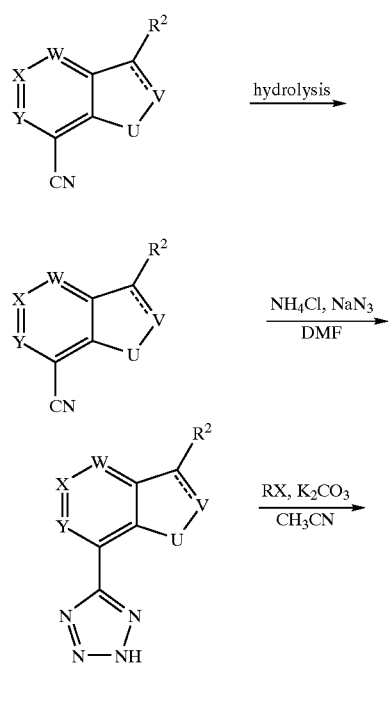

Equation 1 of Scheme 9 depicts the hydrolysis of a nitrile group to the corresponding carboxylic acid. Suitable conditions for carrying out this hydrolysis employ heating the nitrile at reflux with potassium hydroxide in a mixture of water and ethanol for 1 to 100 hours to provide the acid.

Equation 2 of Scheme 9 depicts the conversion of the nitrile to a tetrazole by reacting the nitrile with ammonium chloride and sodium azide in DMF. The tetrazole can then be alkylated by treatment with an electrophile, such as an alkyl halide in the presence of potassium carbonate or alternatively by treatment with a reagent such as trimethylsilyldiazomethane in methanol/benzene.

Scheme 9, equation 3 shows the preparation of an oxadiazole from the nitrile by the addition of hydroxylamine followed by ring closure upon treatment with phosgene. The oxadiazole may then be methylated using trimethylsilyldiazomethane (TMSCHN$_2$) in a mixture of methanol and benzene.

Scheme 10

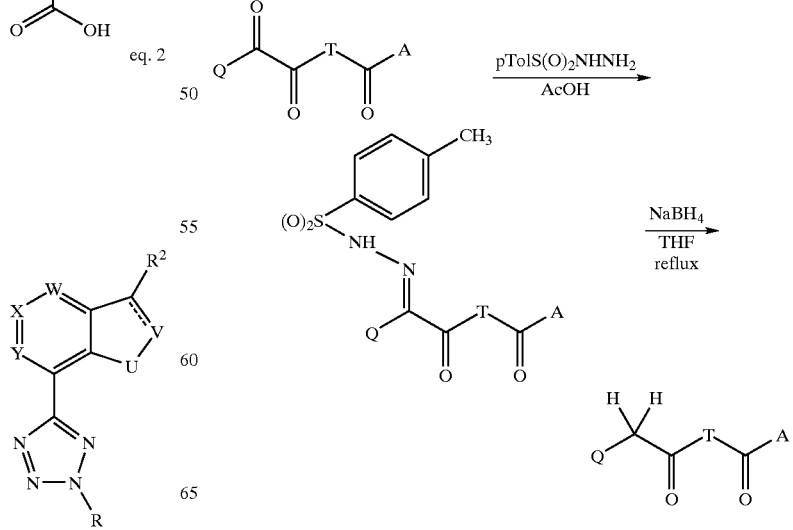

Scheme 10 describes a method by which compounds of formula I can be prepared in which m is 0, n is 1, p is 1, and $R^8=R^{8'}$=hydrogen. Reaction of the keto amide compound with a suitable hydrazide such as p-toluenesulfonyl hydrazide in glacial acetic acid provides the desired hydrazide amide. Frequently heating, sometimes at 90° C. is needed to carry out the reaction. The hydrazide amide is then reduced with sodium borohydride in a solvent such as THF to provide the desired methylene amide. This reaction may also need to be heated to reflux for best results. The procedures in the sequence of example 10 for the reduction of the carbonyl to the methylene via the p-toluensulphonhydrazone intermediate is adapted from: Guan, X.; Borchardt, R. T. *Tetrahedron Lett.*, 1994, 35, 19, 3013–3016.

Scheme 11

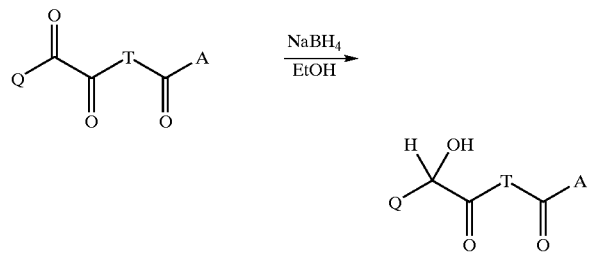

Scheme 11 describes a method by which compounds of formula I can be prepared in which m is 0, n is 1, p is 1, and where one of $R^8$ or $R^{8'}$ is hydroxy and the others are hydrogen. Reduction of the keto amide compound with sodium borohydride (1 to 10 equivalents may be required for best yield of reaction) An example of the procedure described in Example 11 above can be found in Dillard, R. D.; Bach, N. J.; Draheim, S. E.; Berry, D. R.; Carlson, D. G.; Chirgadze, N. Y.; Clawson, D. K.; Hartley, L. W.; Johnson, L. M.; Jones, N. D.; McKinney, E. R.; Mihelich,.E. D.; Olkowski, J. L.; Schevitz, R. W.; Smith, A. C.; Snyder, D. W.; Sommers, C. D.; Wery, J.-P. *J. Med. Chem.*, 1996, 39, 5119–5136 (example 21a of the reference).

Experimental Procedures

The following examples represent typical syntheses of the compounds of Formula I as described generally above. These examples are illustrative only and are not intended to limit the invention in any way. The reagents and starting materials are readily available to one of ordinary skill in the art.

Chemistry

Typical Procedures and Characterization of Selected Examples

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), and DMSO-d6 ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

| LC/MS Method (i.e., compound identification) | |
|---|---|
| Column A: | YMC ODS-A S7 3.0 × 50 mm column |
| Column B: | PHX-LUNA C18 4.6 × 30 mm Column |
| Column C: | XTERRA ms C18 4.6 × 30 mm column |
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Gradient: | 100% Solvent A/0% Solvent B to 0% Solvent A/100% Solvent B |
| Gradient time: | 2 minutes |
| Hold time | 1 minute |
| Flow rate: | 5 mL/min |
| Detector Wavelength: | 220 nm |
| Solvent A: | 10% MeOH/90% H$_2$O/0.1% Trifluoroacetic Acid |
| Solvent B: | 10% H$_2$O/90% MeOH/0.1% Trifluoroacetic Acid |

Compounds purified by preparative HPLC were diluted in methanol (1.2 mL) and purified using the following methods on a Shimadzu LC-10A automated preparative HPLC system.

| Preparative HPLC Method (i.e., compound purification) | |
|---|---|
| Purification Method: | Initial gradient (40% B, 60% A) ramp to final gradient (100% B, 0% A) over 20 minutes, hold for 3 minutes (100% B, 0% A) |
| Solvent A: | 10% MeOH/90% H$_2$O/0.1% Trifluoroacetic Acid |
| Solvent B: | 10% H$_2$O/90% MeOH/0.1% Trifluoroacetic Acid |
| Column: | YMC C18 S5 20 × 100 mm column |
| Detector Wavelength: | 220 nm |

Preparation of Intermediates

Preparation 1

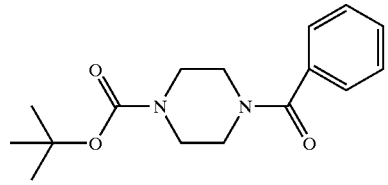

To a solution of tert-butyl-1-piperazinecarboxylate (15.0 g. 80.5 mmol) and benzoic acid (8.94 g, 73.2 mmol) in CH$_2$Cl$_2$ (500 mL), was added DMAP (9.84 g, 80.5 mmol) and EDC (15.39 g, 80.5 mmol). The reaction mixture was stirred at rt for 17 h, and then washed with excess hydrochloric acid (5×250 mL, 1 N aq.) and water (350 mL). The organic layer was dried over MgSO$_4$, filtered and the filtrate concentrated in vacuo to provide Preparation 1 as an off white solid (21 g, 99%). $^1$H NMR: (300 MHz, CD$_3$OD) δ 7.46 (m, 5H), 3.80–3.30 (b m, 8H), 1.47 (s, 9H); LC/MS: (ES+) m/z (M+H)$^+$=291, (2M+H)$^+$=581, HPLC R$_t$=1.430.

Preparation 2

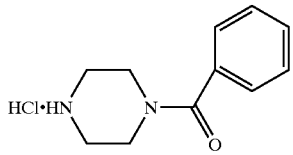

To Preparation 1 was charged a solution of HCl in Dioxane (80 mL, 4 M), and the mixture stirred at room temperature for 5 h. The reaction mixture was concentrated in vacuo to afford the hydrochloride salt of Preparation 2 as a white solid (100% conversion). $^1$H NMR: (300 MHz, CD$_3$OD) δ 7.5 (m, 5H), 4.0–3.7 (b, 4H), 3.7–3.6 (b m, 4H); LC/MS: (ES+) m/z (M+H)$^+$=191, (2M+H)$^+$=381, HPLC R$_t$=0.210.

Preparation 3

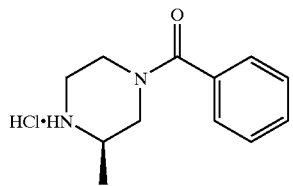

Prepared in the same manner as Preparations 1 and 2 starting from tert-butyl-1-(2-(R)-methylpiperazine) carboxylate (15.0 g. 80.5 mmol) and benzoic acid (8.94 g, 73.2 mmol). $^1$H NMR: (300 MHz, CD$_3$OD) δ 7.47 (m, 5H), 4.50 (app d, J=10.6, 1H), 3.59 (b s, 1H), 3.14–2.57(b m, 5H), 1.15–0.97 (b m, 3H); LC/MS: (ES+) m/z (M+H)$^+$=205, (2M+H)$^+$=409, HPLC R$_t$ =0.310.

Preparations 4–5

Preparations 4 and 5 were prepared according to the following general procedure and as further described below.

General Procedures

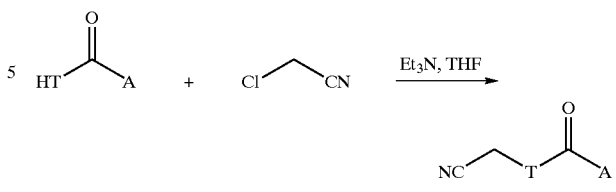

Typical procedure to prepare 1-carbonyl-4-cyanomethylpiperazine derivatives: An excess of chloroacetonitrile (7 mL) was added to a solution of piperazine derivative of formula HTC(O)A (10.5 mmol) in THF (100 mL) and Et$_3$N (10 mL). The reaction was stirred for 10 hours then was quenched with saturated aqueous NaHCO$_3$ (100 mL). The aqueous phase was extracted with EtOAc (3×100 mL). The combined organic layer was dried over MgSO$_4$, filtered, and the filtrate concentrated to a residue, which was used in the further reactions without any purification.

Preparation 4

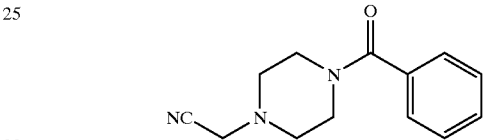

An excess of chloroacetonitrile (7 mL) was added in to a solution of 1-benzoylpiperazine (2 g, 10.5 mmol) in THF (100 mL) and Et$_3$N (10 mL). The reaction was stirred for 10 h before being quenched with saturated aqueous NaHCO$_3$ (100 mL). The aqueous phase was extracted with EtOAc (3×100 mL). The combined organic layer was dried over MgSO$_4$ and concentrated to a residue, Preparation 4, which was used in the further reactions without any purification.

Characterization of Compounds which were Prepared via the same Method Described above

| Entry # | Structure | MS (M + H)$^+$ Calcd. | MS (M + H)$^+$ Observ. And Retention Time |
|---|---|---|---|
| Preparation 4 | 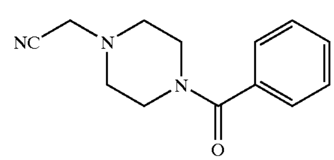 | 230.13 | 230.02 0.84 min (column I) |
| Preparation 5 | 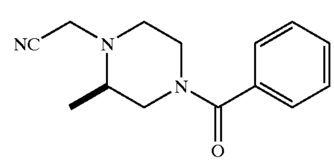 | 244.14 | 244.09 0.96 min (column I) |

| Entry # | Structure | MS (M + H)+ Calcd. | MS (M + H)+ Observ. And Retention Time |
|---|---|---|---|
| Preparation 5a (same method as Prep 4 and 5) | 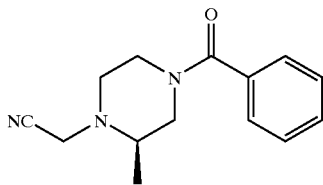 | 244.14 | 244.09 0.95 min (column I) |

Preparation 5

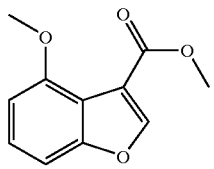

An excess of chloroacetonitrile (7 mL) was added in to a solution of 1-benzoyl-3-(R)-piperazine (2 g, 10.5 mmol) in THF (100 mL) and Et$_3$N (10 mL). The reaction was stirred for 10 h before being quenched with saturated aqueous NaHCO$_3$ (100 mL). The aqueous phase was extracted with EtOAc (3×100 mL). The combined organic layer was dried over MgSO$_4$ and concentrated to a residue, Preparation 5, which was used in the further reactions without any purification.

Preparation 6

In a sealed tube 3-carboxy-4-hydroxybenzofuran, prepared according to the method of Kneen, G.; Maddocks, P. J., *Syn. Comm.* 1986, 1635, (250 mg, 1.40 mmol), K$_2$CO$_3$ (500 mg, 3.62 mmol), acetone (10 mL) and iodomethane (6 mL) were combined and heated to 60° C. for 3 days. The reaction was cooled, concentrated, slurried with Et$_2$O and filtered. The filtrate was concentrated and purified by preparative thin layer chromagraphy (SiO$_2$, 9:1 hexanes/EtOAc (eluting twice)) to yield Preparation 6 (184 mg, 0.89 mmol, 64%) as a white solid. $^1$H NMR: (500 MHz, CDCl$_3$) δ 8.14 (s, 1H), 7.92 (dd, J=8.2, 8.2 Hz, 1H), 7.15 (d, J=8.3 Hz, 1H), 6.77 (d, J=8.1 Hz, 1H), 3.98 (s, 3H), 3.90 (s, 3H); $^{13}$C NMR: (125 MHz, CDCl$_3$) δ 163.1, 157.3, 154.5, 150.3, 126.4, 114.7, 113.9, 105.3, 104.8, 56.1, 51.8. MS: m/z (M+H)+ calcd for C$_{11}$H$_{10}$O$_4$: 207.06; found 207.09. HPLC retention time: 1.36 minutes (column B).

Preparation of Compounds of Formula I

EXAMPLES

Examples 1–4

Examples 1 through 4 were prepared according to the following general procedure and as described for Example 1.

General Procedure to Prepare Cyano-ketone Derivatives

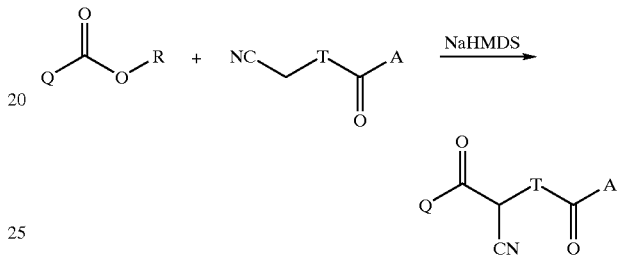

NaHMDS (1.75 mL, 1.0 M in THF) was added into a solution of an amido cyanomethylpiperazine derivative of formula AC(O)TCH$_2$CN (0.44 mmol) and carboxylate of formula QC(O)OR (R is methyl or ethyl, 0.44 mmol) in THF. The reaction was stirred for 10 hours at room temperature then was concentrated in vacuo. The residue was purified using Shimadzu automated preparative HPLC System to give the product of general formula QC(O)CH(CN)TC(O)A.

Example 1

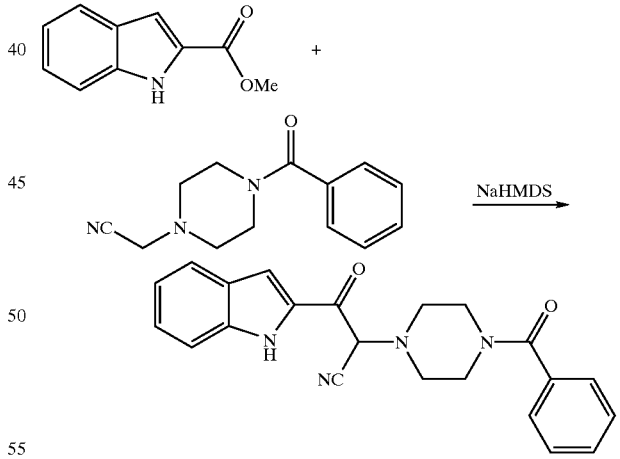

Preparation of N-(benzoyl)-N'-[2-(indol-2-yl)-2-oxo-1-cyano-ethyl]-piperazine, according to the general procedure above, as follows: NaHMDS (1.75 mL, 1.0 M in THF) was added into a solution of 1-benzoyl-4-cyanomethylpiperazine (100 mg, 0.44 mmol) and commercially available methyl-1H-indole-2 carboxylate (83 mg, 0.44 mmol) in THF. The reaction was stirred for 10 hours at room temperature then was concentrated in vacuo. The residue was purified using Shimadzu automated preparative HPLC System to give 1-(benzoyl)-4-[2-(indol-2-yl)-2-oxo-1-cyanoethyl]piperazine.

Example 2 was prepared according to the above general procedure and analogous to the preparation of Example 1 starting from methyl 6-methoxy-1H-indole-2-carboxylate and 1-benzoyl-4-cyanomethyl-3-methylpiperazine. Examples 3 and 4 were prepared according to the above general procedure and analogous to the preparation of Example 1 starting from methyl 4-methoxybenzofuran-3-carboxylate, Preparation 6, and 1-benzoyl-4-cyanomethylpiperazine, Preparation 4, or 1-benzoyl-4-cyanomethyl-3-(R)-methylpiperazine, Preparation 5, respectively.

AC(O)TCH$_2$CN, (0.44 mmol), and an appropriate heterocyclic carboxylate of formula QCO$_2$R', where R' is methyl or ethyl, (0.44 mmol) in an appropriate solvent such as THF. After the reaction was stirred for 10 hours at room temperature, mCPBA (200 mg, >77%) was added and the resulting mixture was stirred for another 10 hours at room temperature. Then the reaction mixture was concentrated in vacuo and the residue was purified using Shimadzu automated preparative HPLC System or by column chromatography or thin layer chromatography to provide the oxoacetylpiperazine derivative of formula QC(O)C(O)TC(O)A.

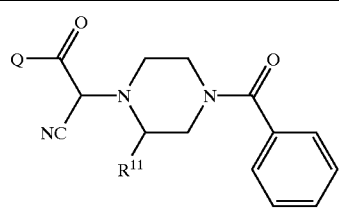

| Example | Q | R$^{11}$ | MS (M + H)$^+$ Calcd. | MS (M + H)$^+$ Observ. | HPLC Retention Time (Min.) | HPLC Column Used |
|---|---|---|---|---|---|---|
| 2 | 6-MeO-indol-2-yl | Me | 417.19 | 417.07 | 1.69 | A |
| 3 | 4-MeO-benzofuran-3-yl | H | 404.15 | 404.18 | 1.48 | A |
| 4 | 4-MeO-benzofuran-3-yl | (R)-Me | 418.17 | 418.20 | 1.55 | A |

Examples 5–14

Examples 5–14 were prepared according to the following general procedure or as described for examples 5 and 6.

General Procedure to Prepare Oxoacetylpiperazine Derivatives

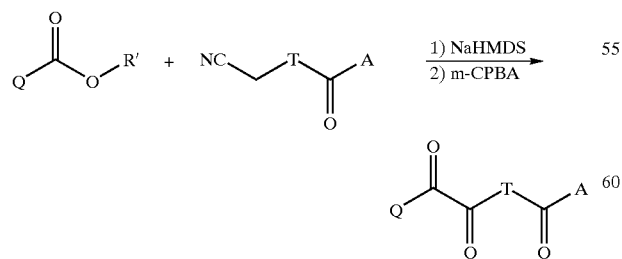

General procedure to prepare oxoacetyl-piperazines: NaHMDS (1.75 mL, 1.0 M in THF) was added into a solution of an appropriate cyanomethylpiperazine derivative of formula

Example 5

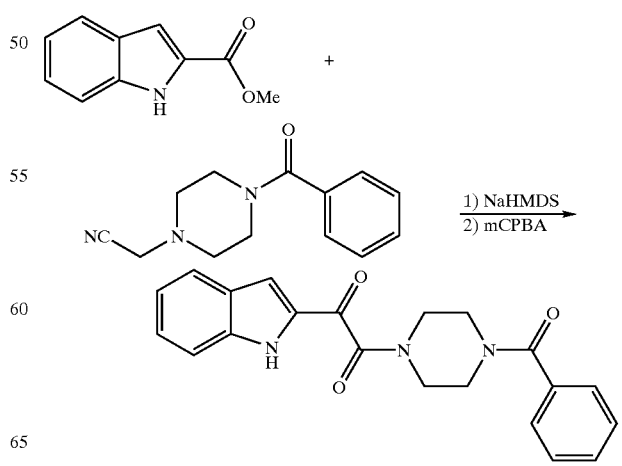

Typical procedure to prepare oxoacetyl-piperazines: Preparation of 1-(benzoyl)-4-[(indol-2-yl)-2-oxoacetyl]piperazine: NaHMDS (1.75 mL, 1.0 M in THF) was added into a solution of 1-benzoyl-4-cyanomethylpiperazine, Preparation 4, (100 mg, 0.44 mmol) and commercially available methyl 1H-indolyl-2-carboxylate (83 mg, 0.44 mmol) in THF. After the reaction was stirred for 10 hours at room temperature, mCPBA (200 mg, >77%) was added and the resulted mixture was stirred for another 10 hours at room temperature. Then the reaction mixture was concentrated in vacuo and the residue was purified using Shimadzu automated preparative HPLC System to give 1-(benzoyl)4-[(indol-2-yl)-2-oxoacetyl]piperazine (3.9 mg).

Example 6

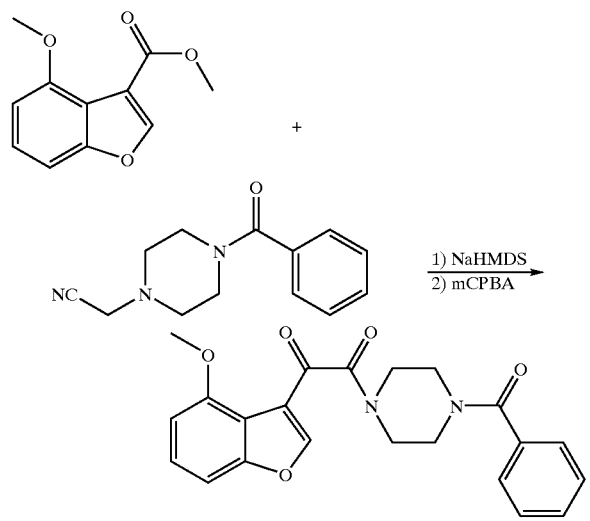

Preparation of 1-(benzoyl)-4-[(benzofuran-3-yl)-2-oxoacetyl]piperazine Sodium hexamethyldisilazide (1.0 M in THF, 1.90 ml, 1.90 mmol) was added dropwise to a stirring solution of methyl 4-methoxybenzofuran-3-carboxylate, Preparation 6 (128 mg, 0.62 mmol) and 1-benzoyl-4-cyanomethylpiperazine, Preparation 4 (149 mg, 0.65 mmol) in THF (10 mL) and stirred 16 hours at room temperature. A solution of m-chloroperoxybenzoic acid (~75% pure, 290 mg, 1.25 mmol) in THF (3 mL) was then added to the reaction mixture and stirring continued 30 min. The viscous solution was diluted with THF (4 mL) and $CH_2Cl_2$ (4 mL), stirred 30 min. and then partitioned between $CH_2Cl_2$ (40 mL) and saturated aqueous $NaHCO_3$ (40 mL). The aqueous layer was further extracted with $CH_2Cl_2$ (2×30 mL) and the combined organics were washed with brine (30 mL), dried over $MgSO_4$, filtered, and the filtrate was concentrated in vacuo. The residue was purified by preparative thin layer chromatography ($SiO_2$, EtOAc) to provide the titled compound (24 mg, contaminated with ~20% of an unknown impurity, 0.050 mmol, 8%) as a yellow solid. $^1$H NMR: (500 MHz, $CDCl_3$) δ 8.34 (s, 1H), 7.55–7.36 (m, 5H), 7.35 (dd, J=8.2, 8.2 Hz, 1H), 7.19 (d, J=8.3 Hz, 1H), 6.80 (d, J=8.1 Hz, 1H), 3.95 (s, 3H), 4.05–3.28 (m, 8H). MS m/z $(M+H)^+$ calcd for $C_{22}H_{20}N_2O_5$:393.14; found 393.13. HPLC retention time: 1.38 minutes (column B).

Examples 7–14

Examples 7–14 were prepared according to the general procedure described above, starting from an appropriate heterocyclic carboxylate of general formula $QCO_2R'$ and an appropriate amido cyanomethylpiperazine derivative. The compounds were characterized as described in Table 1, below.

TABLE I

| Example Number | Q | $R^{11}$ | MS (M + H)$^+$ Calcd. | MS (M + H)$^+$ Observ. | HPLC Retention Time (Min.) | HPLC Column Used |
|---|---|---|---|---|---|---|
| 5 | indol-2-yl | H | 362.15 | 362.06 | 1.27 | A |
| 7 | 6-methoxyindol-2-yl | Me | 428.16* | 427.99* | 1.44 | A |

TABLE I-continued

| Example Number | Q | R[11] | MS (M + H)[+] Calcd. | MS (M + H)[+] Observ. | HPLC Retention Time (Min.) | HPLC Column Used |
|---|---|---|---|---|---|---|
| 8 | 6-F-indol-2-yl | Me | 394.16 | 394.05 | 1.73 | A |
| 9 | 5-Cl-indol-2-yl | Me | 410.13 | 409.99 | 1.60 | A |
| 10 | 1,3-dimethyl-4-OMe-pyrazolo[3,4-b]pyridin-5-yl | H | 422.18 | 422.16 | 1.20 | A |
| 11 | 1,3-dimethyl-4-Cl-pyrazolo[3,4-b]pyridin-5-yl | Me | 472.18** | 472.13** | 1.35 | A |
| 12 | 1,3-dimethyl-4-OMe-pyrazolo[3,4-b]pyridin-5-yl | Me | 436.20 | 436.22 | 1.29 | A |
| 13 | 1-ethyl-4-NH(CH$_2$)$_3$CH$_3$-pyrazolo[3,4-b]pyridin-5-yl | Me | | | | |
| 14 | 1-ethyl-4-NH(CH$_2$)$_3$CH$_3$-pyrazolo[3,4-b]pyridin-5-yl | H | | | | |

**(M + methanol + H)[+] instead of (M + H)[+].
*(M + Na)[+] instead of (M + H)[+]

Examples 15–19

Examples 15–19 were prepared from the corresponding glyoxylic acid and benzoyl piperazine according to the general procedure described below.

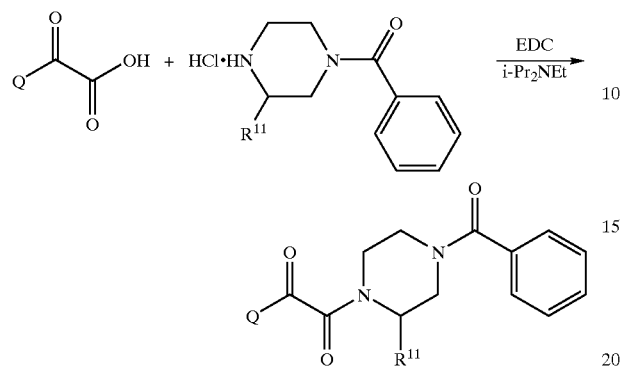

To a solution of glyoxylic acid derivative (QCOCOOH, 1 equiv.) in DMF was added 3-(R)-methyl-1-benzoylpiperazine hydrochloride, for examples 15–17 (1.5 equiv) or 1-benzoylpiperazine hydrochloride, for examples 18–19 (1.5 equiv), followed by EDC (1.5 equiv.) and diisopropylethylamine (3 equiv). The reaction mixture was stirred at room temperature for 16 hours and the crude product was purified by preparative HPLC. The compounds were characterized as shown in Table 2 or the following examples.

TABLE 2

| Example Number | $R^{11}$ | Q | HPLC Retention Time | MS Data $(M + H)^+$ |
|---|---|---|---|---|
| 15 | (R)-Me | NC-indole-5-yl | 1.35 | 401 |
| 16 | (R)-Me | EtO₂C-indole-5-yl | 1.32 | 448 |
| 17 | (R)-Me | 3-NC-indole-6-yl | 1.25 | 401 |

Example 18

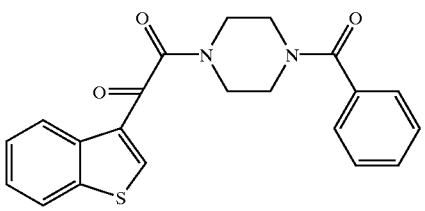

1-(benzoyl)-4-[(benzothiophen-3-yl)-2-oxoacetyl]piperazine: $^1$H NMR (300 MHz, CDCl$_3$) δ 8.74 (d, 1H, J=7.8 Hz), 8.51 (s, 1H), 7.90 (d, 1H, J=8.1 Hz), 7.27 (m, 7H), 3.65 (m, 8H). MS m/z: (M+H)$^+$ calcd for C$_{21}$H$_{19}$N$_2$O$_3$S: 379.11; found 379.07. HPLC retention time: 1.64 minutes (column A).

Example 19

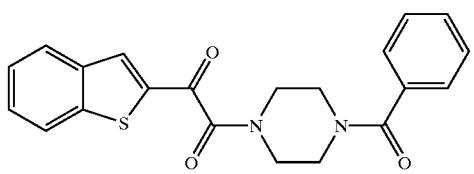

1-(benzoyl)-4-[(benzothiophen-2-yl)-2-oxoacetyl]piperazine: $^1$H NMR (500 MHz, CDCl$_3$) δ 8.00 (m, 2H), 7.76 (s, 1H), 7.68 (m, 7H), 4.0 (m, 8H).

Example 20

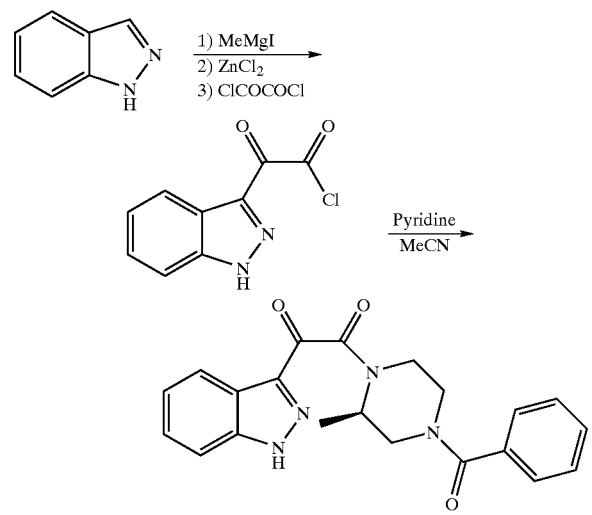

Preparation of 1-(benzoyl)-4-[(indazol-3-yl)-2-oxoacetyl]-piperazine: To a solution of indazole (1.0 g) in THF (50 mL), 3.1 mL of methyl magnesium iodide (3.0 M in diethyl ether) was added at room temperature. The resulting mixture was stirred at room temperature for 1 hour then ZnCl$_2$ (1.0 M in diethyl ether) was added. The reaction mixture was then stirred 1 hour, then an excess of oxalyl chloride (7.39 mL) was added slowly. The reaction mixture was stirred for 8 hours at room temperature then was concentrated in vacuo in order to remove solvent and excess oxalyl chloride and to provide a residue containing (1H-Indazol-3-yl)-2-oxo-acetyl chloride.

The crude residue containing (1H-Indazol-3-yl)-2-oxo-acetyl chloride (50 mg) was dissolved in dry CH₃CN (7 mL), and to the resulting solution was added 3-(R)-methyl-1-benzoyl piperazine (50 mg) and pyridine (1 mL). The reaction mixture was stirred for 1 hour at room temperature then was concentrated in vacuo. The resulting residue was purified using Shimadzu automated preparative HPLC System to give 1-(benzoyl)-4-[(1H-indazol-3-yl)-2-oxoacetyl] piperazine (2.5 mg). $^1$H NMR (500 MHz, MeOD) δ 8.42 (m, 2H), 7.90 (m, 1H), 7.69 (m, 1H), 7.46 (m, 5H), 5.00–3.00 (m, 8H), 1.30 (m, 3H). MS m/z: (M+H)⁺ calcd for $C_{21}H_{21}N_4O_3$:377.16; found 377.28. HPLC retention time: 1.49 minutes (column A).

| Example Number | Q | $R^{11}$ | MS (M + H)⁺ Calcd. | MS (M + H)⁺ Observ. | HPLC Retention Time | HPLC Column Used |
|---|---|---|---|---|---|---|
| 20 | indazol-3-yl | (R)-Me | 377.16 | 377.28 | 1.36 | A |

Example 21

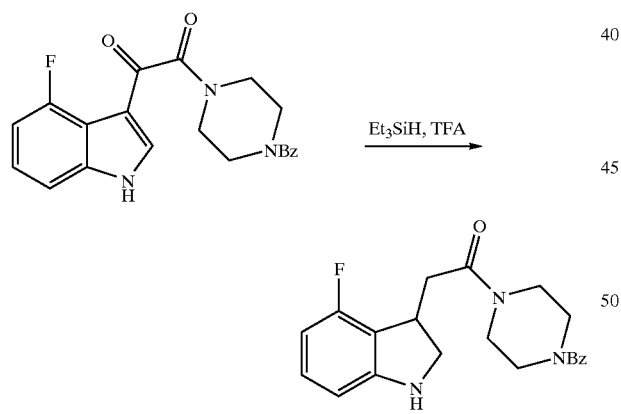

Preparation of N-(benzoyl)-N'-[(4-fluoro1-indolin-3-yl)-acetyl]-piperazine: N-(benzoyl)-N'-[(4-fluoro-indol-3-yl)-2-oxoacetyl]-piperazine (500 mg) was dissolved in a solution of Et₃SiH (1 ml) in TFA (10 ml). The reaction was stirred for 10 hours. Solvents were removed under vaccum, and the residue was purified using Shimadzu automated preparative HPLC System to give N-(benzoyl)-N'-[(4-fluoro1-indolin-3-yl)-acetyl]-piperazin (2.5 mg).

-continued

| Q | $R^{11}$ | (M + H)⁺ Calcd. | (M + H)⁺ Observ. | tion Time | Column Used |
|---|---|---|---|---|---|
| 4-fluoroindolin-3-yl | H | 368.18 | 368.11 | 0.99 | A |

Example 22

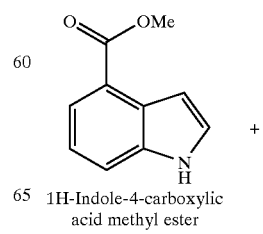

1H-Indole-4-carboxylic acid methyl ester

+

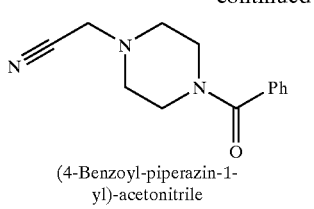

(4-Benzoyl-piperazin-1-yl)-acetonitrile

1) NaHMDS, THF
2) mCPBA
→

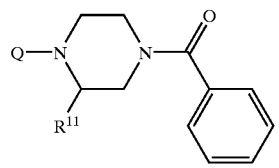

1-(4-Benzoyl-piperazin-1-yl)-2-(1H-indol-4-yl)-ethane-1,2-dione

Preparation of 1-(4-benzoyl-piperazin-1-yl)-2-(1H-indol-4-yl)-ethane-1,2-dione: NaHMDS (1.3 mL of a 1.0 M in THF solution, 1.3 mmol) was added to a stirring solution of 1H-indole-4-carboxylic acid methyl ester (0.048 g, 0.27 mmol) and (4-benzoyl-piperazin-1-yl)-acetonitrile (63 mmol, 0.27 mmol) in THF (3 mL) and the reaction mixture was stirred overnight. mCPBA (0.01 g of 77% max., 0.43 mmol) was added to the reaction mixture, stirred 1 d, and the solution was partitioned between brine (15 mL) and EtOAc (3×10 mL). The combined organic layers were dried (MgSO$_4$), filtered, concentrated and purified using Shimadzu automated preparative HPLC System to give 1-(4-benzoyl-piperazin-1-yl)-2-(1H-indol-4-yl)-ethane-1,2-dione (0.028 mg, 77 mmol, 29%) as a yellow solid: MS m/z: (M+H)$^+$ calcd for C$_{21}$H$_{19}$N$_3$O$_3$:362.14; found 362.09. HPLC retention time: 1.13 minutes (column A).

Examples 23–25

The following compounds were prepared by methods described for the products and intermediates in Example 22 except that 1H-indole-7-carboxylic acid methyl ester, 1H-indole-5-carboxylic acid methyl ester, or 1H-indole-6-carboxylic acid methyl ester were used as the starting materials.

Characterization of Intermediates or Final Products with the following Sub-structure

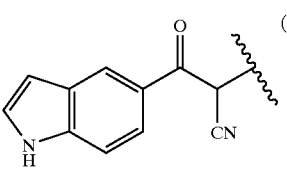

| Example | Q | R | MS (M + H)$^+$ Calcd. | MS (M + H)$^+$ Observ. And Retention Time |
|---|---|---|---|---|
| Example 23 | 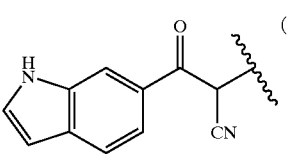 | Me | 376.17 | 376.25 Rf = 2.04 min. (column A) |
| Example 24 | ![indole-5-yl carbonyl] | (R)-Me | 387.18 | 387.11 Rf = 1.68 min. (column E) |
| Example 25 | ![indole-6-yl carbonyl] | (R)-Me | 387.18 | 387.12 Rf = 1.75 min. (column E) |

Example 26

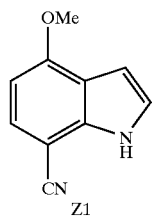
Z1

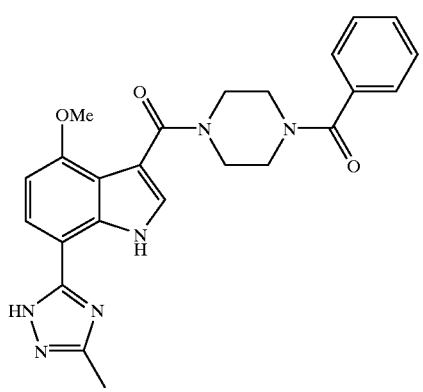
BMS-553570

To a mixture of 4-methoxy-7-cyanoindole Z1 (603 mg, 3.50 mmol) in 1,2-dichloroethane (30 ml) at r.t. was added dropwise oxalyl chloride (3.5 ml, 40 mmol), and the resulting mixture refluxed at 100° C. for 16 h (Ref. Taber, D. F.; Sethuraman M. R. *J. Org. Chem.* 2000, 65, 254). The excess reagent and volatile were then evaporated in vacuo and the residue further dried under high vacuum. To a mixture of the crude residue in THF (20 ml) at r.t. was added benzoylpiperazine hydrochloride (965 mg, 4.26 mmol). The mixture was stirred for about 10 min and then cooled to 0° C. before adding N,N-diisopropylethylaminie (3.0 ml, 17.2 mmol). The reaction mixture was stirred at r.t. for 3 h, evaporated in vacuo and the residue obtained partitioned between 1N hydrochloric acid and dichloromethane. The organic mixture was evaporated in vacuo and the residue purified by preparative TLC (5% MeOH/CH$_2$Cl$_2$). To the purified material (80 mg) in a reusable sealed tube at r.t. was added a solution of HCl in 1,4-dioxane (2.3 ml, 4 N), followed by ethanol (0.46 ml, 200 proof, anhydrous). The resulting reaction mixture was cooled to −5° C. and then bubbled anhydrous HCl gas through for 50 min. The mixture was then warmed to r.t. and stirred overnight in the tightly closed sealed tube. The mixture was transferred to a round bottom flask and evaporated to give a crude yellowish oil. To this crude oil in ethanol (2.0 ml, 200 proof, anhydrous) was added N,N-diisopropylethylamine (77 mg, 0.6 mmol) and acetic hydrazide (69 mg, 0.93 mmol, dried under high vacuum before use). The reaction mixture was stirred at 60° C. for 17 h and added acetic hydrazide (69 mg, 0.93 mmol). The mixture was then further stirred at 80 to 95° C. for about 30 h and 105° C. for 2 days before evaporated to give a residue, from which the product of example 26 was isolated by preparative TLC (5% MeOH/CH$_2$Cl$_2$). $^1$H NMR: (CDCl$_3$) □ 10.55 (b s, 1H), 7.80 (b s, 1H), 7.41 (b s, 5H), 7.34 (b s, 1H), 6.55 (b d, 1H), 4.00–3.30 (b m, 8H), 3.89 (s, 3H), 2.44 (s, 3H); LC/MS: (ES+) m/z (M+H)$^+$=445; HPLC R$_t$=1.047 (HPLC conditions: Start %B=0, Final %B=100, Gradient time=2 min, Flow rate=5 ml/min, Wavelength=220 nm, Solvent A=10% MeOH/90% H$_2$O/0.1% TFA, Solvent B=90% MeOH/10% H$_2$O/0.1% TFA, Column YMC ODS-A C18 S7 3.0×50 mm).

General Procedures for Preparation of Examples 27–29

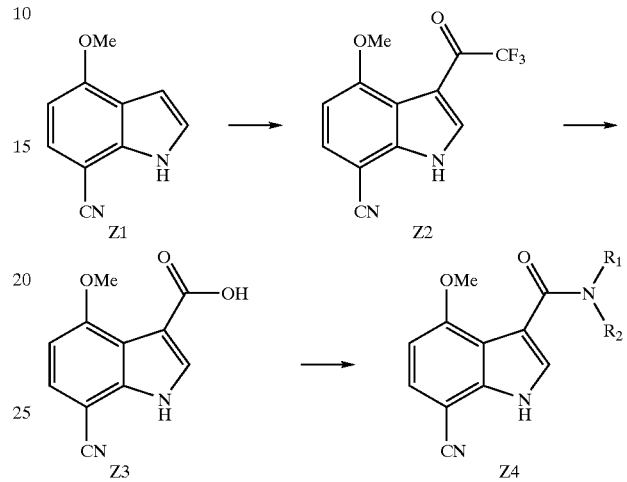

Representative Procedures

To a solution of indole Z1 (650 mg, 3.78 mmol) in THF (6 ml) at r.t. was added trifluoroacetic anhydride (1.8 ml, 12.7 mmol). The reaction flask was cooled in an ice-water bath and pyridine (0.35 ml, 4.33 mmol) added to the mixture, which was then stirred at r.t. for about 30 h. the reaction was quenched with water and the mixture extracted twice with ethyl acetate. The combined organic extracts were evaporated in vacuo to give a crude yellowish solid, which was titurated with MeOH and the solid filtered to obtain the trifluoromethylketone Z2.

A mixture of the trifluoromethylketone Z2 (302 mg, 1.15 mmol) in DMF (4 ml) was stirred at r.t. with the reaction flask open to air for about 10 min. The mixture was then added dropwise to a suspension of NaH (318 mg, 13.3 mmol) in DMF (4 ml), and the resulting mixture stirred at 60° C. for 30 min. The reaction mixture was then cooled to 0° C. and added excess of 1N hydrochloric acid. The precipitates were filtered and dried to give the acid Z3, and the filtrate extracted with ether (12 times). The combined organic extracts were evaporated in vacuo and the residue washed with MeOH to give another batch of acid Z3. (Ref. Delgado, A.; Clardy, J.; *Tetrahedron Lett.* 1992, 33, 2789.)

Amide Z4 was prepared by coupling to the corresponding amine (1.5 equiv.) in DMF at r.t. using EDC (1.8 equiv.), DMAP (2 equiv.) and NMM (4.6 equiv.) (or in CH$_2$Cl$_2$ using polymer-bound cyclohexylcarbodiimide (3 equiv., Novabiochem) and N,N-diisopropylethylamine (5 equiv.)). The reaction mixture was stirred overnight, added excess of 1N hydrochloric acid and extracted with EtOAc (6 times). The combined organic extracts were back washed with 1N hydrochloric acid and evaporated in vacuo to give a crude residue, which was purified by reverse phase preparative HPLC.

Other indole analogs, e.g. 4-fluoroindole and 7-bromoindole, were prepared analogously.

| Examples | Compound | (M + H)+ | HPLC R$_t$/min |
|---|---|---|---|
| Example 27 | (4-OMe, 7-CN indole-3-carbonyl-piperazine-benzoyl) | 389 | 1.203 |
| Example 28 | (4-OMe, 7-CN indole-3-carbonyl-(methyl)piperazine-benzoyl) | 403 | 1.267 |
| Example 29 | (4-F indole-3-carbonyl-piperazine-benzoyl) | 352 | 1.307 |

HPLC conditions for examples 27–29: Start % B=0, Final % B=100, Gradient time=2 min, Flow rate=5 ml/min, Wavelength=220 nm, Solvent A=10% MeOH/90% H$_2$O/ 0.1% TFA, Solvent B=90% MeOH/10% H$_2$O/0.1% TFA, Column XTERRA C18 S7 3.0×50 mm.

Example 30

The following compound was prepared by methods described for the products and intermediates in Example 22 except that 1H-indole-7-carboxylic acid methyl ester was used as the starting materials.
Characterization of Intermediates or Final Products with the following Sub-structure

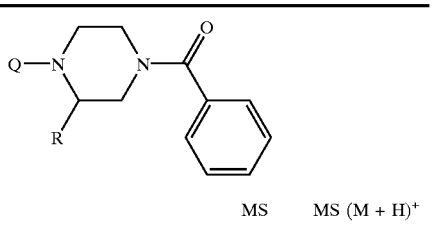

| Example | Q | R | (M + H)+ Calcd. | Observ. And Retention Time |
|---|---|---|---|---|
| Example 30 | (indole-CN-carbonyl) | Me | 387.18 | 387.12 Rf = 1.65 min. (column A) |

Example 31

Preparation of
3-[2-(4-Benzoyl-piperazin-1-yl)-2-oxo-ethyl]-4-fluoro-1H-indole-7-carboxylic acid methylamide Step A 3-[2-(4-Benzoyl-piperazin-1-yl)-1-para-toluenesulfonhydrazono-2-oxo-ethyl]-4-fluoro-1H-indole-7-carboxylic acid methylamide.

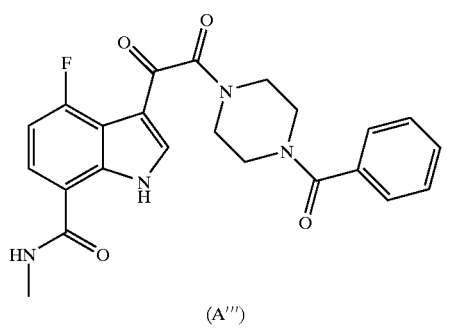

(A''')

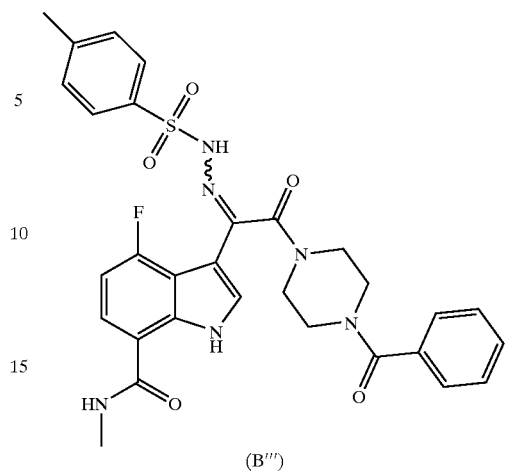

(B''')

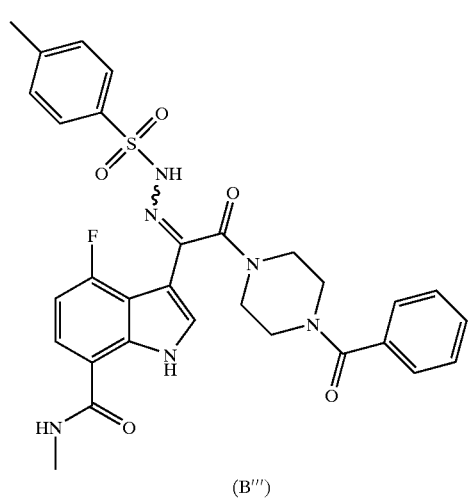

(B''')

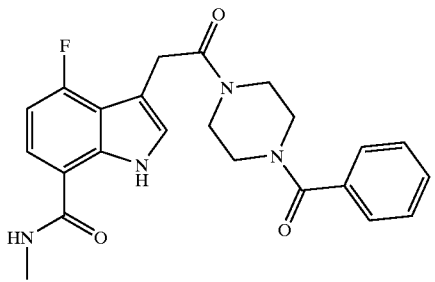

(Example 31)

A suspension of 3-[2-(4-benzoyl-piperazin-1-yl)-2-oxo-acetyl]-4-fluoro-1H-indole-7-carboxylic acid methylamide (A''', 0.400 g 0.92 mmol) in 2,2,2-trifluoroethanol (5 mL) was treated with p-toluenesulfonhydrazide (0.256 g, 1.37 mmol) and glacial acetic acid (0.5 mL), and heated at refluxing temperature (oil bath, 90° C.). The suspension became a solution upon warming. The reaction was stirred at reflux under nitrogen atmosphere for 36 hours. Solvent was removed by rotary evaporator, and the crude residue was purified by flash silica gel column chromatography, eluting with ethyl acetate:methanol (100:0 changing to 90:10). The combined mixture of syn- and anti-addition products was dried by rotary evaporation to give the title compound (B''') as a yellow solid (0.335 g, 0.55 mmol, Y 59.8%). $^1$H-NMR (500 MHz, d-6 DMSO): 12.02 and 11.85 (s, 1H); 11.01 and 10.89 (s, 1H) 8.60 (br, 1H, CONH); 7.8–7.4 (m, 10H, aromatic); 7.14 (br s, 1H, C2-H); 6.93 (m, 1H, C5-H); 3.9–3.4 (2×br, 8H, piperazine); 3.17 (s, 3H, CH$_3$Ph); 2.85 and 2.83 (d, 3H, CH$_3$). LRMS (ES+) m/z [M+H]$^+$=605.2, (ES−) m/z [M−H]$^−$=603.3.

3-[2-(4-Benzoyl-piperazin-1-yl)-2-oxo-ethyl]-4-fluoro-1H-indole-7-carboxylic acid methylamide (Example 31).

A suspension of B''' (0.270 g, 0.45 mmol) in anhydrous tetrahydrofuran (12 mL) under nitrogen atmosphere was treated with sodium borohydride (1.678 g, 9.0 mmol) and the suspension was warmed to refluxing temperature (oil bath, 90° C.). At the elevated temperature the reaction mixture was treated with a minimum amount of anhydrous methanol (dropwise addition until dissolution occurred), and the reaction was stirred at reflux overnight. After cooling, glacial acetic acid (3 mL) was added and the whole reaction mixture was passed quickly through a short path silica gel column, eluting with dichloromethane followed by 1:10 methanol:dichloromethane. The fractions containing product were dried in vacuo and the residue was purified by flash silica gel column chromatography eluting with dichloromethane and 1:20 methanol:dichloromethane. Product was recovered as a pale yellow solid (0.018 g, 0.043 mmol, Y. 9.6%). $^1$H—NMR (300 MHz, d-4 methanol): 8.4 (br, 0.4H, NH); 7.53–7.42 (m, 7H, aromatic); 7.17 (s, 1H, C2-H); 6.71 (m, 1H, C5-H); 4–3.4 (2×br, 8H, piperazine); 3.35 (m, 2H, CH$_2$CO); 2.94 (d, 3H, CH$_3$). LRMS (ES+) m/z [M+H]$^+$=423.14, (ES−) m/z [M−H]$^−$=421.2.

Note: The procedure for the reduction of the carbonyl to the methylene via the p-toluensulphonhydrazone intermediate is adapted from: Guan, X.; Borchardt, R. T. *Tetrahedron Lett.*, 1994, 35, 19, 3013–3016.

Example 32

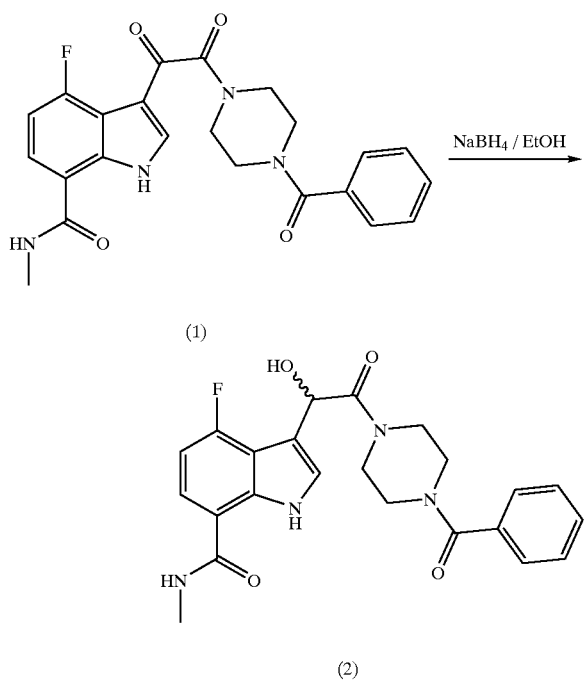

3-[2-(4-Benzoyl-piperazin-1-yl)-1-hydroxy-2-oxo-ethyl]-4-fluoro-1H-indole-7-carboxylic acid methylamide (2): A suspension of 3-[2-(4-Benzoyl-piperazin-1-yl)-2-oxo-acetyl]-4-fluoro-1H-indole-7-carboxylic acid methylamide (A''', 0.260 g., 0.60 mmol) in absolute ethanol (5 mL) under nitrogen atmosphere was treated with sodium borohydride (0.031 g, 0.8 mmol). The suspension became a solution within several minutes. The reaction was stirred overnight. Solvent was removed in-vaccuo and the residue was purified by silica gel column chromatography, eluting with ethyl acetate:methanol (100:0 changing to 90:10). Product fractions were pooled and dried in-vaccuo to give the title compound (Example 32, 0.106 g, 0.24 mmol, Y 40%). 1H—NMR (300 MHz, d-6 DMSO): 11.33 (s, 1H indole NH); 8.51 (d, 1H, CONH); 7.7–7.1 (m, 7H, aromatic); 6.85 (m, 1H, C5-H); 5.70 (b, 1H, OH); 5.27 (d, 1H, CHCO); 3.8–3.3 (2×br, 8H, piperazine)2.83 (d, 3H, $CH_3$). LRMS (ES+) m/z $[M+Na]^+$=460.9, (ES−) $[M-H]^-$=437.0.

Procedure adapted from: Dillard, R. D.; Bach, N. J.; Draheim, S. E.; Berry, D. R.; Carlson, D. G.; Chirgadze, N. Y.; Clawson, D. K.; Hartley, L. W.; Johnson, L. M.; Jones, N. D.; McKinney, E. R.; Mihelich, E. D.; Olkowski, J. L.; Schevitz, R. W.; Smith, A. C.; Snyder, D. W.; Sommers, C. D.; Wery, J.-P. J. Med. Chem., 1996, 39, 5119–5136 (example 21a).

Characterization of Biological Active Compounds

Biology

In Table 3 and hereafter, the following definitions apply.

"$\mu M$" means micromolar;

"ml" means milliliter;

"$\mu l$" means microliter;

"mg" means milligram;

The materials and experimental procedures used to obtain the results reported in Table 3 are described below.

Cells

Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/ml Geneticin (Life Technologies, Gaithersburg, Md.) and 0.4 mg/ml Zeocin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Life Technologies, Gaithersburg, Md.).

Experiment

1. Compound was added to HeLa CD4 CCR5 cells plated in 96 well plates at a cell density of $5 \times 10^4$ cells per well in 100 $\mu l$ Dulbecco's Modified Eagle Medium containing 10% fetal Bovine serum at a concentration of <20 $\mu M$.
2. 100 $\mu l$ of single-round infectious reporter virus in Dulbecco's Modified Eagle Medium was then added to the plated cells and compound at an approximate multiplicity of infection (MOI) of 0.01, resulting in a final volume of 200 $\mu l$ per well and a final compound concentration of <10 $\mu M$.
3. Samples were harvested 72 hours after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 $\mu l$ of Dulbecco's Modified Eagle Medium (without phenol red) and 50 $\mu l$ of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. An $EC_{50}$ provides a method for comparing the antiviral potency of the compounds of this invention. The effective concentration for fifty percent inhibition ($EC_{50}$) was calculated with the Microsoft Excel Xlfit curve fitting software. For each compound, curves were generated from percent inhibition calculated at 10 different concentrations by using a four parameter logistic model (model 205). The $EC_{50}$ data obtained is shown below in Table 3. In Table 3, compounds with an $EC_{50}$ of greater than 5 $\mu M$ are designated as Group C; compounds with an $EC_{50}$ of 1 $\mu M$ to 5 $\mu M$ are designated Group B; compounds with an $EC_{50}$ of less than 1 $\mu M$ are designated as Group A; and compounds with a potency of greater than 0.5 $\mu M$ which were not evaluated at higher doses to determine the $EC_{50}$ value are designated Group D.

TABLE 3

| Example # | Q | m,n,p,R⁸, R⁸' | T | EC$_{50}$ Range |
|---|---|---|---|---|
| 2 | 6-MeO-indol-2-yl | m = 1, n = 1, p = 0, R⁸ = CN, R⁸' = H | (S)-3-methylpiperazine | A |
| 3 | 4-MeO-benzofuran-3-yl | m = 1, n = 1, p = 0, R⁸ = H, R⁸' = CN | piperazine | A |
| 4 | 4-MeO-benzofuran-3-yl | m = 1, n = 1, p = 0, R⁸ = H, R⁸' = CN | (S)-3-methylpiperazine | D |
| 5 | indol-2-yl | m = 1, n = 0, p = 1 | piperazine | A |
| 6 | 4-MeO-benzofuran-3-yl | m = 1, n = 0, p = 1 | piperazine | D |
| 7 | 6-MeO-indol-2-yl | m = 1, n = 0, p = 1 | (S)-3-methylpiperazine | A |
| 8 | 5-F-indol-2-yl | m = 1, n = 0, p = 1 | (S)-3-methylpiperazine | A |
| 9 | 5-Cl-indol-2-yl | m = 1, n = 0, p = 1 | (S)-3-methylpiperazine | A |

TABLE 3-continued

| Example # | Q | m,n,p,R⁸,R⁸' | T | EC$_{50}$ Range |
|---|---|---|---|---|
| 10 | 4-methoxy-1,3-dimethyl-1H-pyrazolo[3,4-b]pyridin-5-yl | m = 1, n = 0, p = 1 | piperazine | B |
| 11 | 4-chloro-1,3-dimethyl-1H-pyrazolo[3,4-b]pyridin-5-yl | m = 1, n = 0, p = 1 | 3-methylpiperazine | C |
| 12 | 4-methoxy-1,3-dimethyl-1H-pyrazolo[3,4-b]pyridin-5-yl | m = 1, n = 0, p = 1 | 3-methylpiperazine | B |
| 13 | 4-(butylamino)-1-ethyl-1H-pyrazolo[3,4-b]pyridin-5-yl | m = 1, n = 0, p = 1 | (3R)-methylpiperazine | A |
| 14 | 4-(butylamino)-1-ethyl-1H-pyrazolo[3,4-b]pyridin-5-yl | m = 1, n = 0, p = 1 | piperazine | C |
| 15 | 3-cyano-1H-indol-5-yl | m = 1, n = 0, p = 1 | (3R)-methylpiperazine | A |
| 16 | 3-(ethoxycarbonyl)-1H-indol-5-yl | m = 1, n = 0, p = 1 | (3R)-methylpiperazine | B |

TABLE 3-continued

| Example # | Q | m,n,p,R⁸,R⁸' | T | EC$_{50}$ Range |
|---|---|---|---|---|
| 17 | 3-cyano-1H-indol-6-yl | m = 1, n = 0, p = 1 | (S)-3-methylpiperazin-1-yl | A |
| 18 | benzo[b]thiophen-3-yl | m = 1, n = 0, p = 1 | piperazin-1-yl | B |
| 19 | benzo[b]thiophen-2-yl | m = 1, n = 0, p = 1 | piperazin-1-yl | B |
| 20 | 1H-indazol-3-yl | m = 1, n = 0, p = 1 | (S)-3-methylpiperazin-1-yl | A |
| 21 | 4-fluoro-2,3-dihydro-1H-indol-3-yl | m = 1, n = 1, p = 1, R⁸, R⁸' = H | piperazin-1-yl | A |
| 22 | 1H-indol-4-yl | m = 1, n = 0, p = 1 | piperazin-1-yl | A |
| 23 | 1H-indol-7-yl | m = 1, n = 0, p = 1 | (R)-3-methylpiperazin-1-yl | B |
| 24 | 1H-indol-5-yl | m = 1, n = 1, p = 0, R⁸ = CN, R⁸' = H | (S)-3-methylpiperazin-1-yl | On test |

TABLE 3-continued
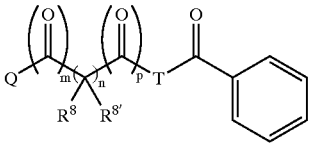
| Example # | Q | m,n,p,R⁸, R⁸' | T | EC₅₀ Range |
|---|---|---|---|---|
| 25 | 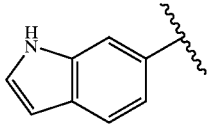 | m = 1, n = 1, p = 0, R⁸ = CN, R⁸' = H | 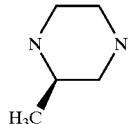 | On test |
| 26 | 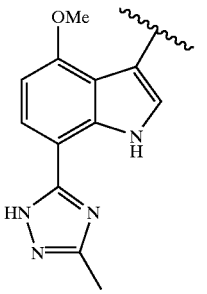 | m = 1, n = 0, p = 0 | 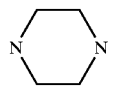 | B |
| 27 | 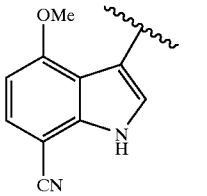 | m = 1, n = 0, p = 0 | 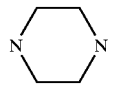 | D |
| 28 | 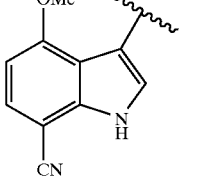 | m = 1, n = 0, p = 0 | 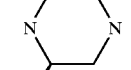 | D |
| 29 | 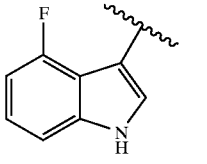 | m = 1, n = 0, p = 0 |  | A |
| 30 | 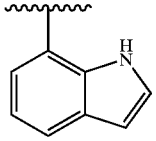 | m = 1, n = 1, p = 0, R⁸ = CN, R⁸' = H | 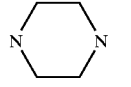 | D |

TABLE 3-continued

| Example # | Q | m,n,p,R⁸, R⁸' | T | EC$_{50}$ Range |
|---|---|---|---|---|
| 31 | [4-F-7-(CH₃NHC(O))-indol-3-yl] | m = 1, n = 1, p = 0, $R^8$ = H, $R^{8'}$ = H | piperazine | B |
| 32 | [4-F-7-(CH₃NHC(O))-indol-3-yl] | m = 1, n = 1, p = 0, $R^8$ = OH, $R^{8'}$ = H | piperazine | A |

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present invention, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present invention.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:

1. A compound of Formula I, including pharmaceutically acceptable salts thereof,

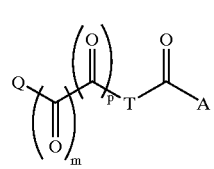

I wherein:

Q is

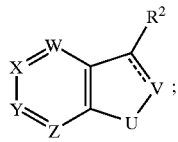

— represents a bond;

A is phenyl;

T is

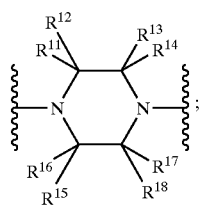

U is NR$^7$;
V is C(H)$_k$R$^1$ or N(R$^{7'}$)$_k$;
W is CR$^3$;
X is CR$^4$;
Y is CR$^5$;
Z is CR$^6$;
k is 0;
R$^1$, R$^2$, R$^3$, R$^4$, R$^5$, and R$^6$ are each independently selected from the group consisting of a bond, hydrogen, halogen, cyano, X'R$^{24}$, C$_{1-6}$alkyl, triazolyl, methyl-substituted triazolyl, C(O)NR$^{28}$R$^{29}$ and CO$_2$R$^{25}$;
R$^7$ and R$^{7'}$ are each independently selected from the group consisting of a bond and (CH$_2$)$_r$H, wherein r is 0–6; m and p are each 1;
R$^9$ is hydrogen or C$_{1-6}$alkyl;
R$^{11}$, R$^{12}$, R$^{13}$, R$^{14}$, R$^{15}$, R$^{16}$, R$^{17}$, and R$^{18}$ are each independently selected from hydrogen or C$_{1-3}$alkyl;
X' is selected from the group consisting of NR$^9$ and O;
R$^{24}$ is hydrogen or C$_{1-6}$alkyl;
R$^{25}$ is C$_{1-6}$alkyl;
R$^{28}$ and R$^{29}$ are independently selected from the group consisting of hydrogen, C$_{1-6}$alkyl;
provided when U is NR$^7$; V is C(H)$_k$R$^1$; W is CR$^3$; X is CR$^4$; Y is CR$^5$; Z is CR$^6$; then R$^2$ is not a bond; and
provided that at any given time only one of the members selected from the group consisting of R$^1$, R$^2$, R$^3$, R$^4$, R$^5$, R$^6$, R$^7$ and R$^{7'}$ is a bond, and further provided that said bond is the point of attachment to the adjacent carbon atom in the compound of Formula 1.

2. A compound of claim 1, including pharmaceutically acceptable salts thereof, wherein:

T is

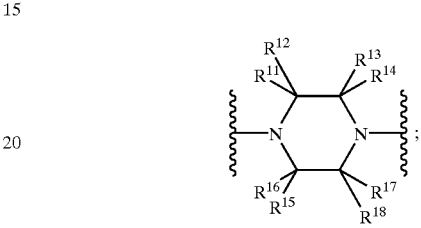

R$^{11}$, R$^{12}$, R$^{13}$, R$^{14}$, R$^{15}$, R$^{16}$, R$^{17}$, and R$^{18}$ are each independently hydrogen, methyl or ethyl.

3. A compound of claim 2, including pharmaceutically acceptable salts thereof, wherein:

U is —NR$^7$; and V is N.

4. A compound of claim 2 in which W, X, Y, and Z are each CH and R$^7$ is H.

5. A pharmaceutical composition which comprises an antiviral effective amount of a compound of Formula I, including pharmaceutically acceptable salts thereof, as claimed in any of claims 1, 2, 3, and 4 and one or more pharmaceutically acceptable carriers, excipients or diluents.

6. A method for treating a mammal infected with the HIV virus comprising administering to said mammal an antiviral effective amount of a compound of Formula I, including pharmaceutically accceptable salts thereof, as claimed in any of claims 1, 2, 3, and 4 and one or more pharmaceutically acceptable carriers, excipients or diluents.

* * * * *